United States Patent
Movsesian et al.

(10) Patent No.: US 9,994,830 B2
(45) Date of Patent: Jun. 12, 2018

(54) METHODS FOR MODULATING CYCLIC NUCLEOTIDE-MEDIATED SIGNALING IN CARDIAC MYOCYTES AND COMPOSITIONS

(71) Applicants: Matthew Movsesian, Salt Lake City, UT (US); Manuela Zaccolo, Oxford (GB)

(72) Inventors: Matthew Movsesian, Salt Lake City, UT (US); Manuela Zaccolo, Oxford (GB)

(73) Assignee: The United States of America as Represented by the Department of Veterans Affairs, Washington, DC (US)

( * ) Notice: Subject to any disclaimer, the term of this patent is extended or adjusted under 35 U.S.C. 154(b) by 203 days.

(21) Appl. No.: 14/800,657

(22) Filed: Jul. 15, 2015

(65) Prior Publication Data

US 2016/0083701 A1 Mar. 24, 2016

Related U.S. Application Data

(60) Provisional application No. 62/024,994, filed on Jul. 15, 2014.

(51) Int. Cl.
*C12N 9/16* (2006.01)
*C12Q 1/44* (2006.01)
*A61K 38/00* (2006.01)

(52) U.S. Cl.
CPC .............. *C12N 9/16* (2013.01); *C12Q 1/44* (2013.01); *A61K 38/00* (2013.01); *C12Y 301/04017* (2013.01); *G01N 2333/916* (2013.01); *G01N 2500/04* (2013.01); *G01N 2500/20* (2013.01)

(58) Field of Classification Search
None
See application file for complete search history.

(56) References Cited

U.S. PATENT DOCUMENTS 8,722,866 B2 5/2014 Movsesian

FOREIGN PATENT DOCUMENTS

EP 1607769 B1 5/2010

OTHER PUBLICATIONS

Ahmad F., et al., Regulation of Sarcoplasmic Reticulum Ca2_ ATPase 2(SERCA2) Activity by Phosphodiesterase 3A (PDE3A) in Human Myocardium. *The Journal of Biological Chemistry*, 290(11): 6763-6776, (2015)—Exhibit 3.
Beca S., et al., Phosphodiesterase type 3a regulates basal myocardial contractillty through interacting with sarcoplasmic reticulum calcium atpase type 2a signaling complexes in mouse heart. *Circulation research*. 112:289-297 (2013)—Exhibit 4.
Ding B., et al., A positive feedback loop of phosphodiesterase 3 (pda3) and inducible camp early repressor (icer) leads to cardiomyocyte apoptosis. *Proceedings of the National Academy of Sciences of the United States of America*. 102:14771-14776 (2005)—Exhibit 5.
Ding B., et al., Functional role of phosphodiesterase 3 in cardiomyocyte apoptosis; implication in heart failure. *Circulation*, 111:2469-2476 (2005)—Exhibit 6.
Hambleton R., et al., Isoforms of cyclic nucleotide phosphodiesterase pde3 and their contribution to camp hydolytic activity in sebcellular fractions of human myocardium. *J Biol Chem*. 280:39168-39174 (2005)—Exhibit 7.
Kenan Y., et al., Functions of the n-terminal region of cyclic nucleotide photphodiesterse 3 (pde 3) isoforms. *The Journal of biological chemistry*, 275:12331-12338 (2000)—Exhibit 8.
Leroy M.J., et al., Characterization of two recombinant pde3 (cgmp-inhibited cyclic nucleotide phosphodiesterase) isoforms, rcgip1 and hcgip2, expressed in nih 3006 murine fibroblasts and sf9 insect cells, *Biochemister*, 35:10194-10202 (1996)—Exhibit 9.
Meacci E., et al. Molecular cloning and expression of human myocardial cgmp-inhibited camp phosphodiesterase. *Proceedings of the National Academy of Sciences of the United States of America*. 89:3721-3725 (1992)—Exhibit 10.
Oikawa M., et al., Cyclic nucleotide phosphodiesterase 3a1 protects the heart against ischemia-reperfusion injury. *Journal of molecular and cellular cardiology*. 64:11-19 (2013)—Exhibit 11.
Shakur Y., et al., Membrane localization of cyclic nucleotide phosphodiesterase 3 (pde3). Two n-terminal domains are required for the efficient targeting to and association of, pd3 with endo plasmic reticulum. *The Journal of biological chemistry*. 275:38749-38761 (2000)—Exhibit 12.
Vandeput, F., et al., Selective regulation of cyclic nucleotise phosphodiesterase PDE3A isoforms. *Proc Natl Acad Sci U S A*. 110(49). 19778-19783 (2013)—Exhibit 13.
Wechsler J., et al., Isoforms of cyclic nucleotide phosphodiesterase pda3a in cardiac myocytes. *The Journal of biological chemistry*. 277:38072-38078 (2002)—Exhibit 14.

*Primary Examiner* — Suzanne M Noakes
(74) *Attorney, Agent, or Firm* — Adriano & Associates

(57) ABSTRACT

The invention provides a polypeptide possessing anti-hypertrophic activity in a cardiac myocyte, wherein the polypeptide is a mutant variant derived from wild-type PDE3A1 protein and wherein the wild-type PDE3A1 protein has the amino acid sequence given in SEQ ID NO:1 at amino acid position 146 to 1141.

12 Claims, 14 Drawing Sheets

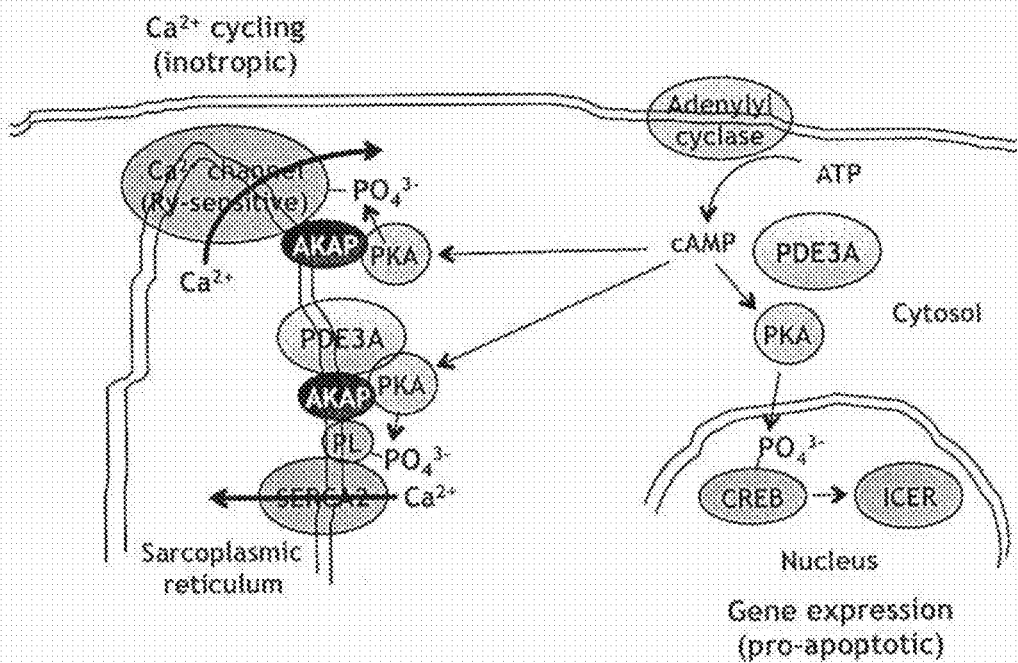

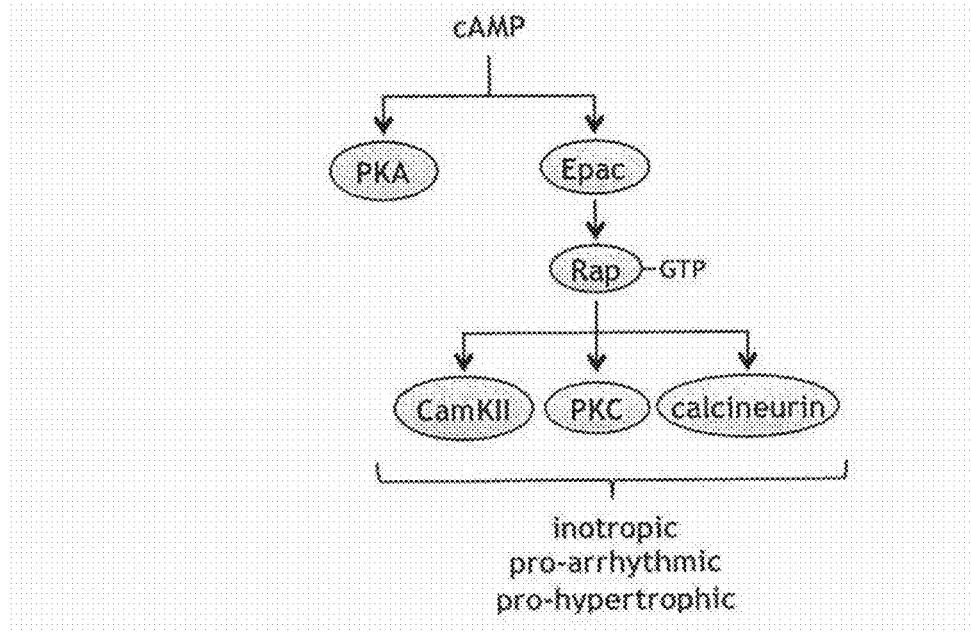

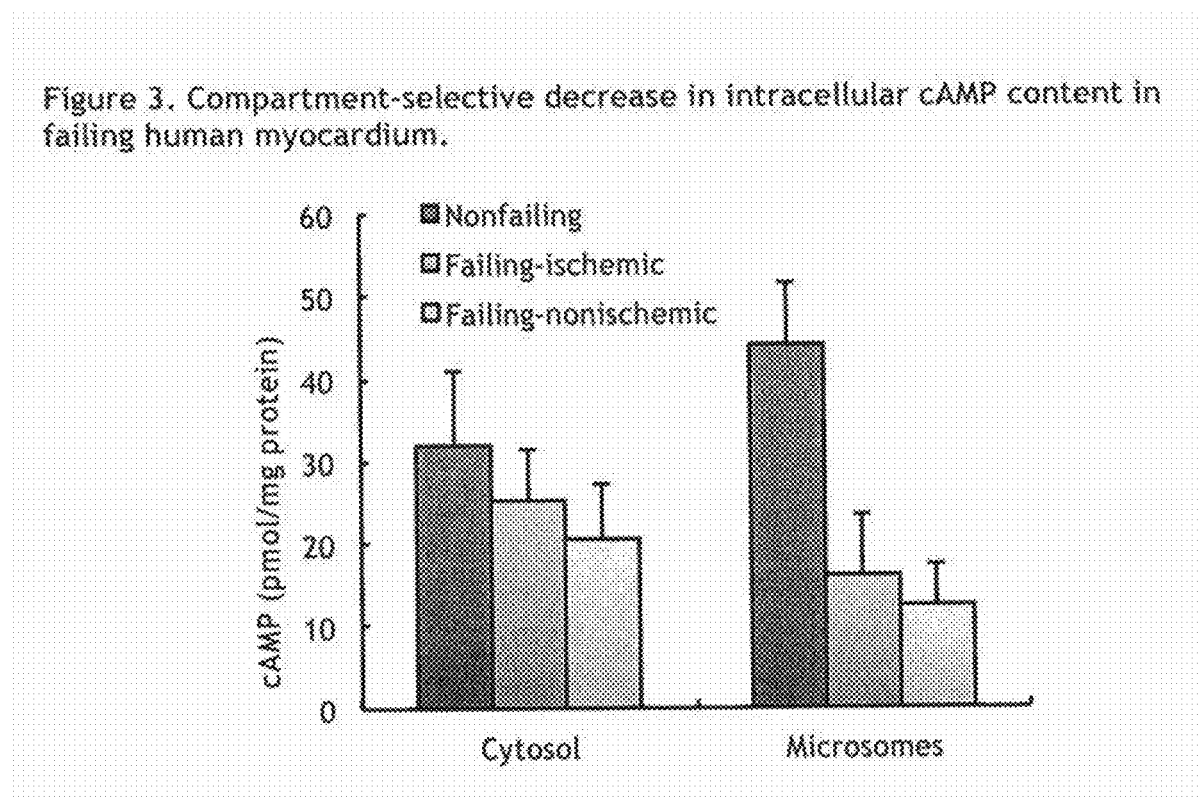
Figure 3. Compartment-selective decrease in intracellular cAMP content in failing human myocardium.

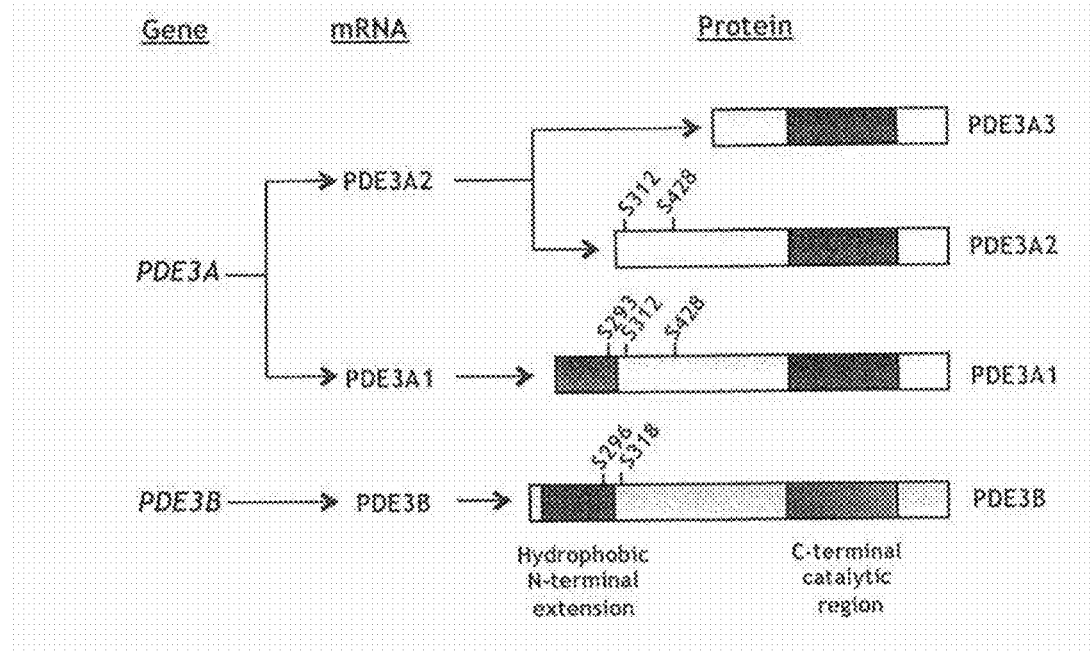

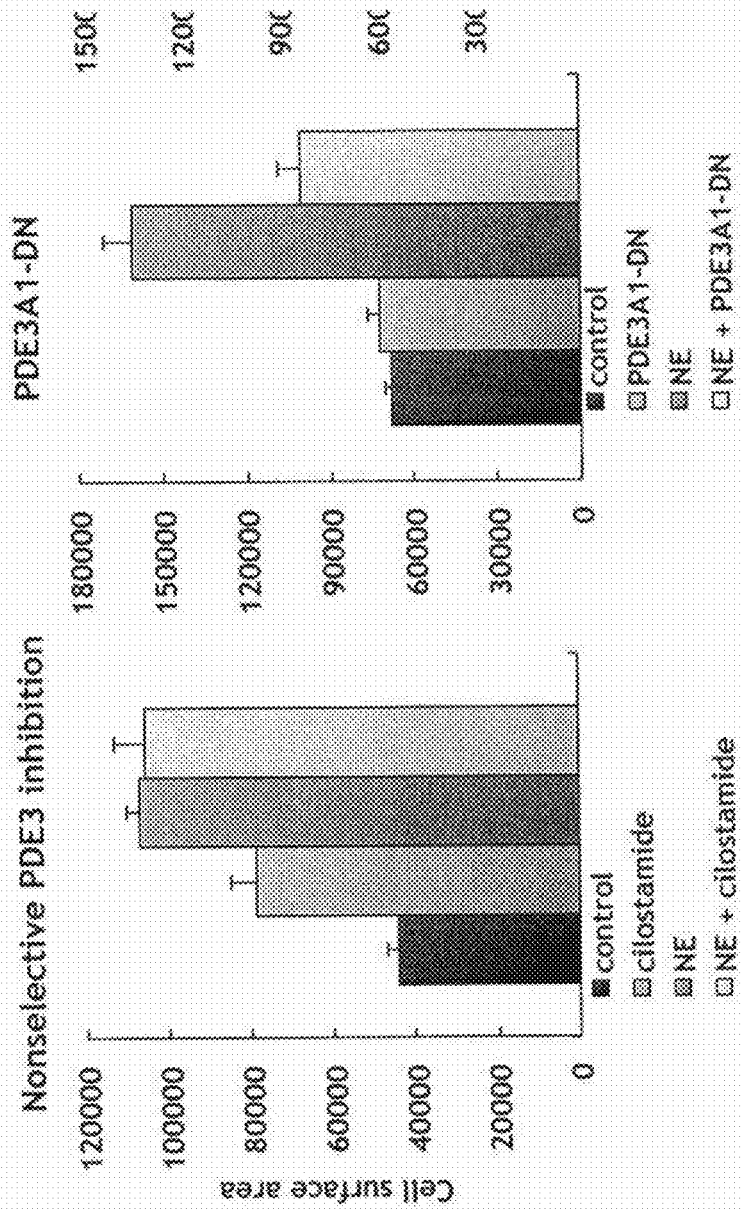

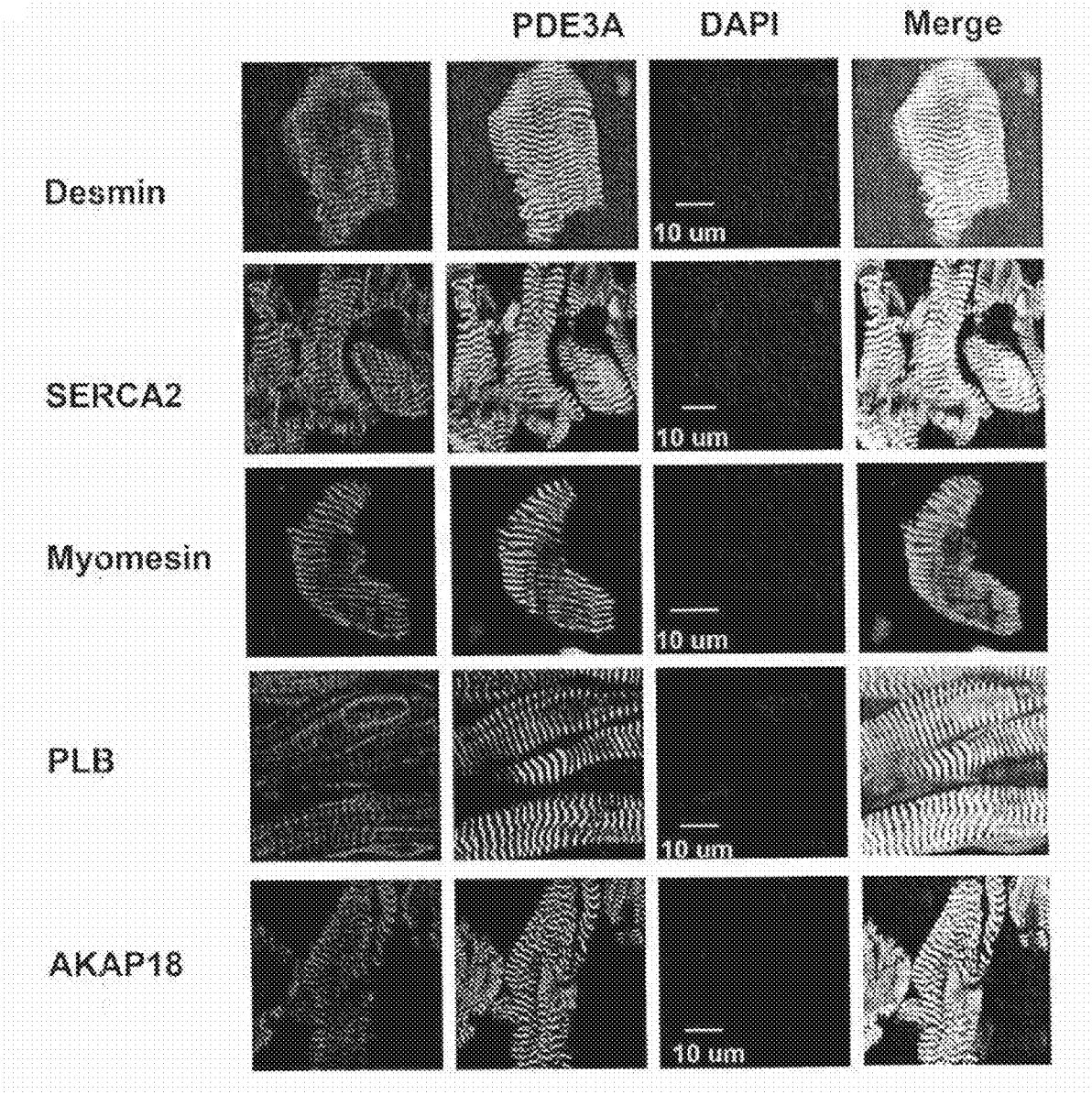

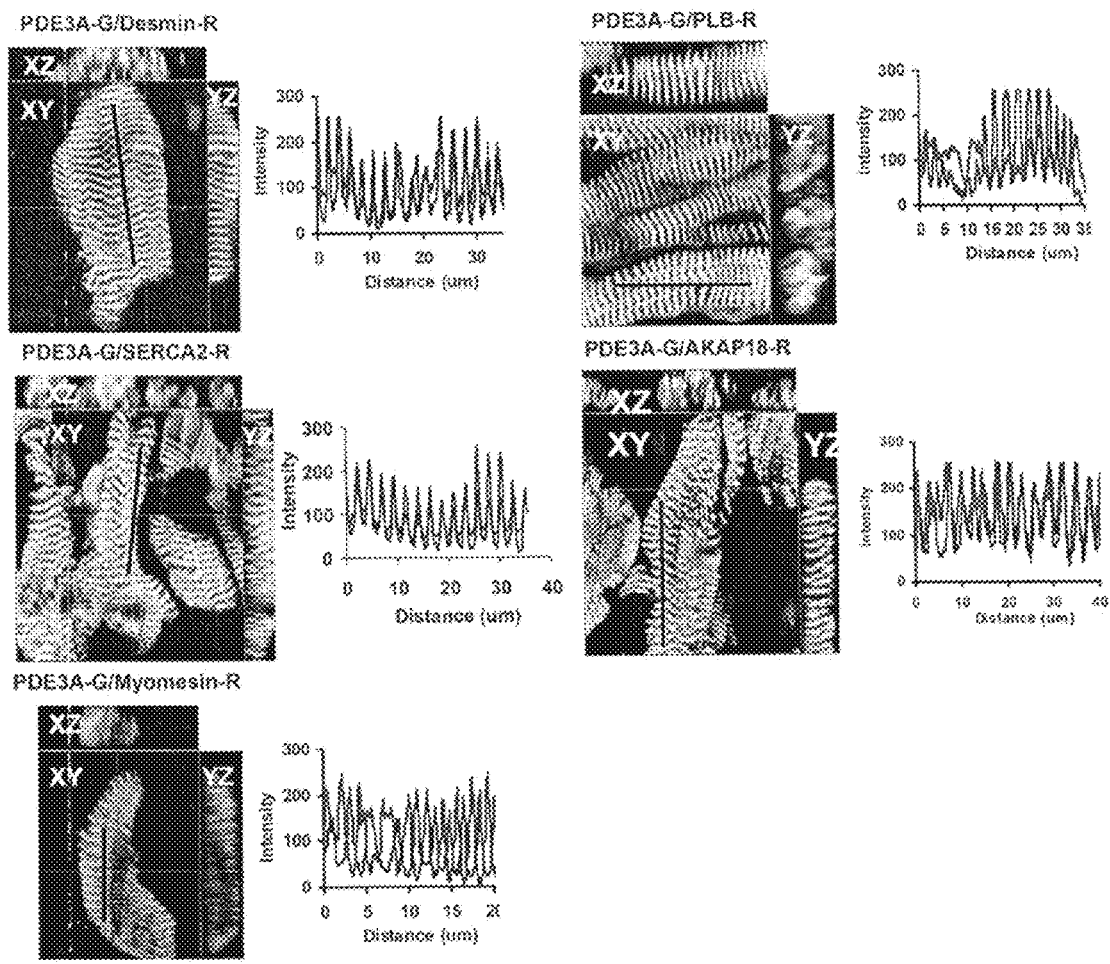
Figure 6B. PDE3A, SERCA2, PLB, AKAP18, co-localize in the Z-bands in normal human myocardium.

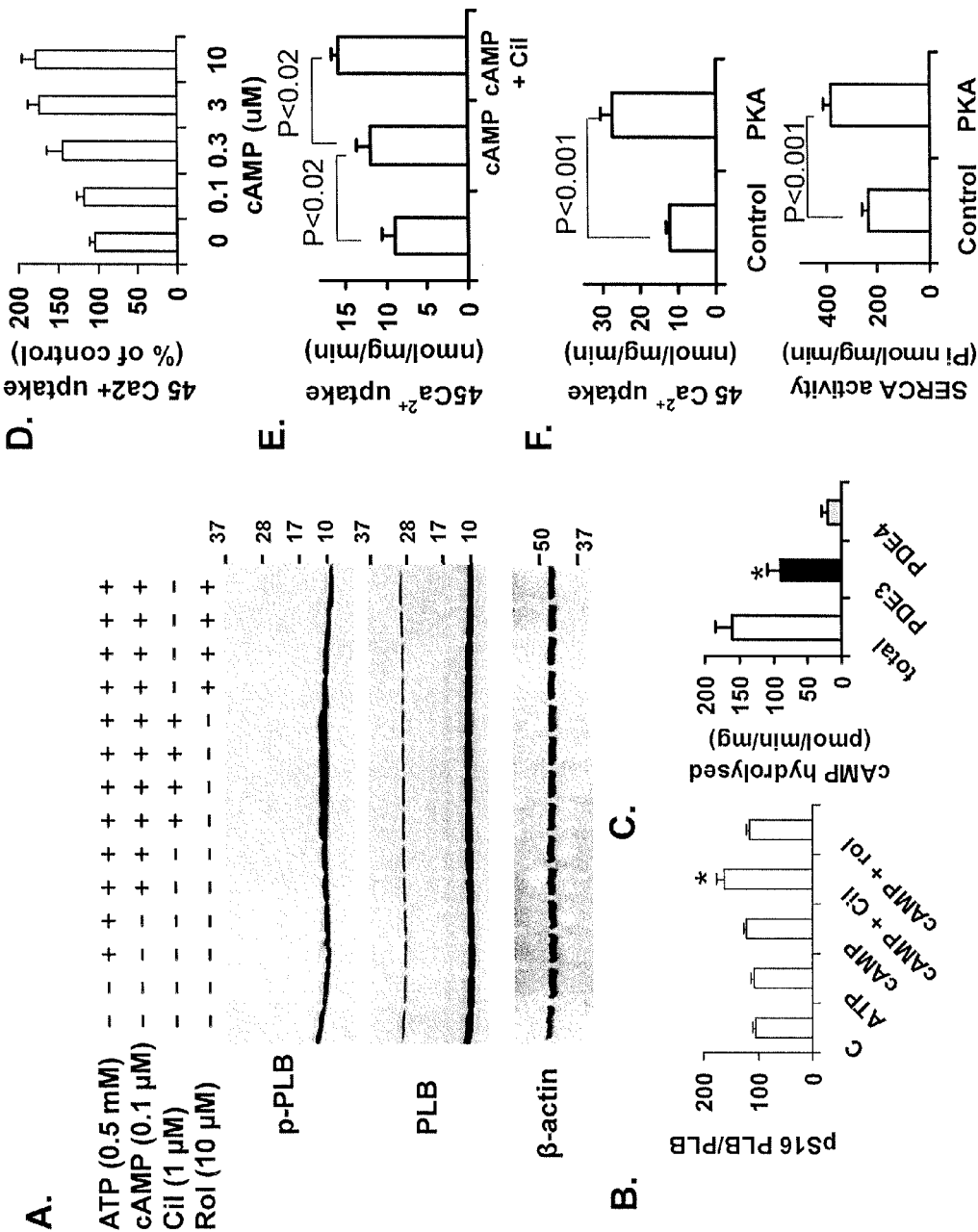
Figure 7A-F. cAMP, PKA, and PDE3-inhibition increase SERCA2 activity and Ca²⁺ uptake.

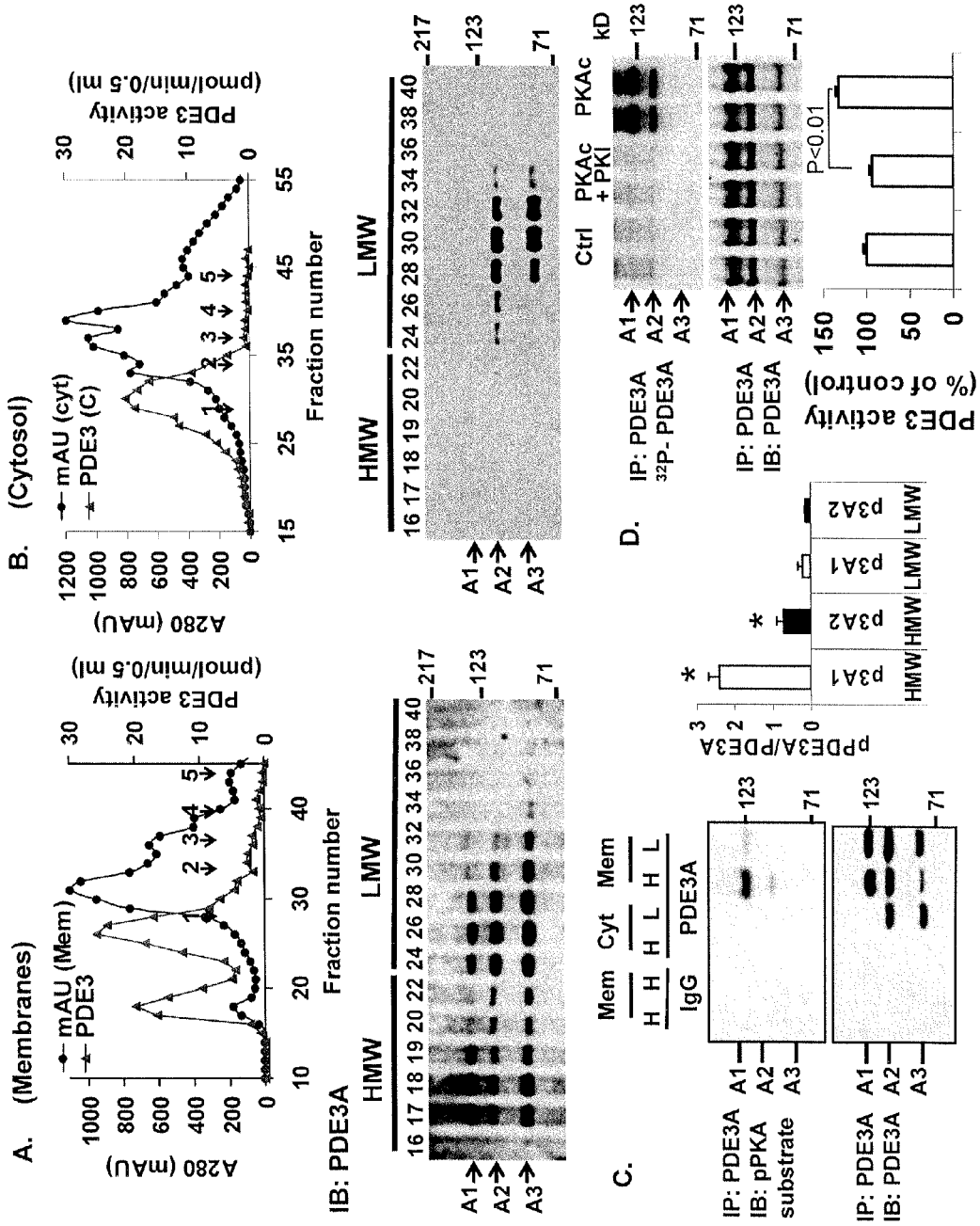
Figure 8A-D. Detection of PDE3A isoforms by Superose 6 (S6) gel-filtration chromatography of solubilized human myocardial membrane or cytosolic fractions.

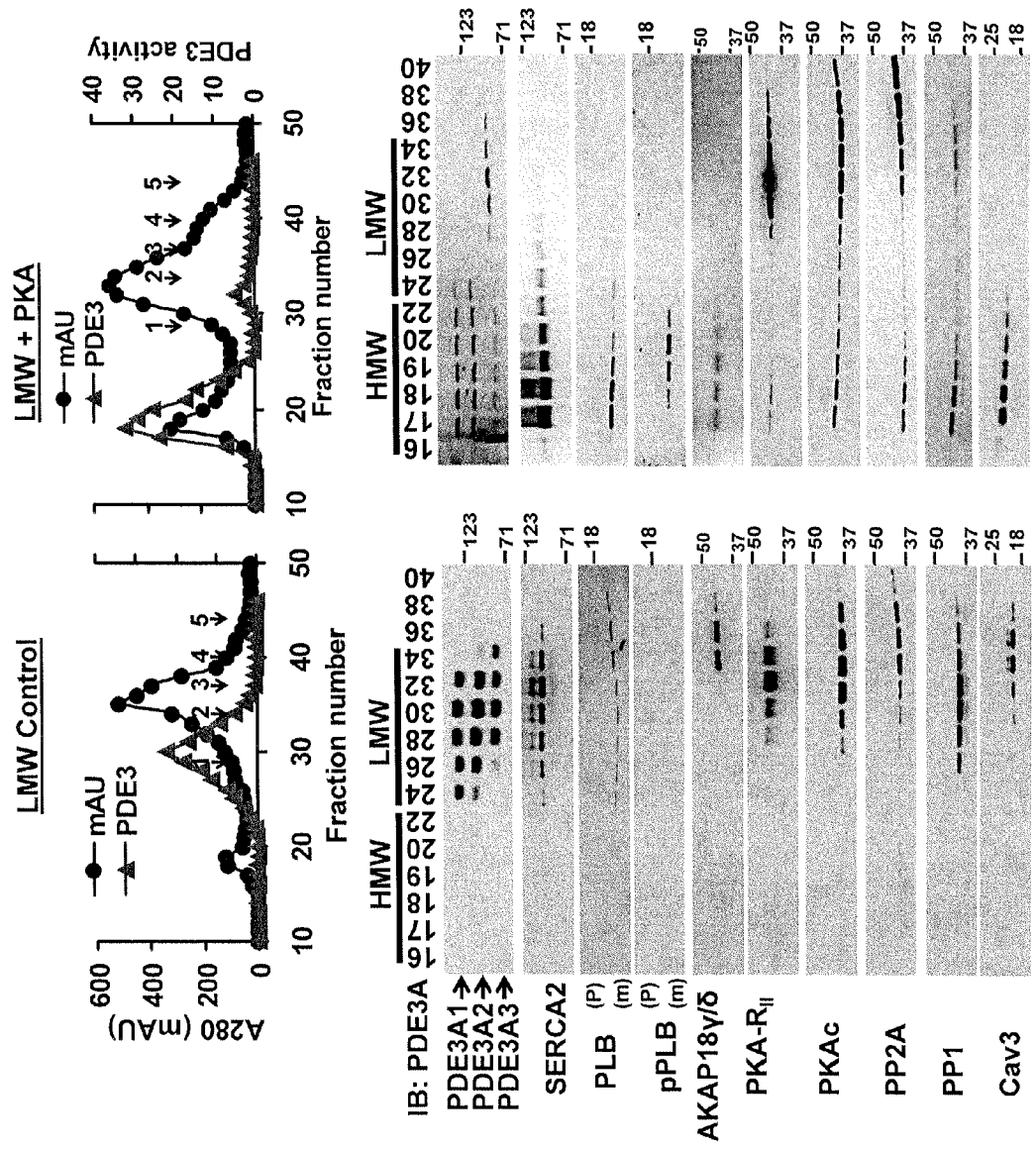
Figure 9. rPKAc increases interaction of PDE3A with signaling molecules in Superose 6 LMW-fractions of solubilized human myocardial membranes.

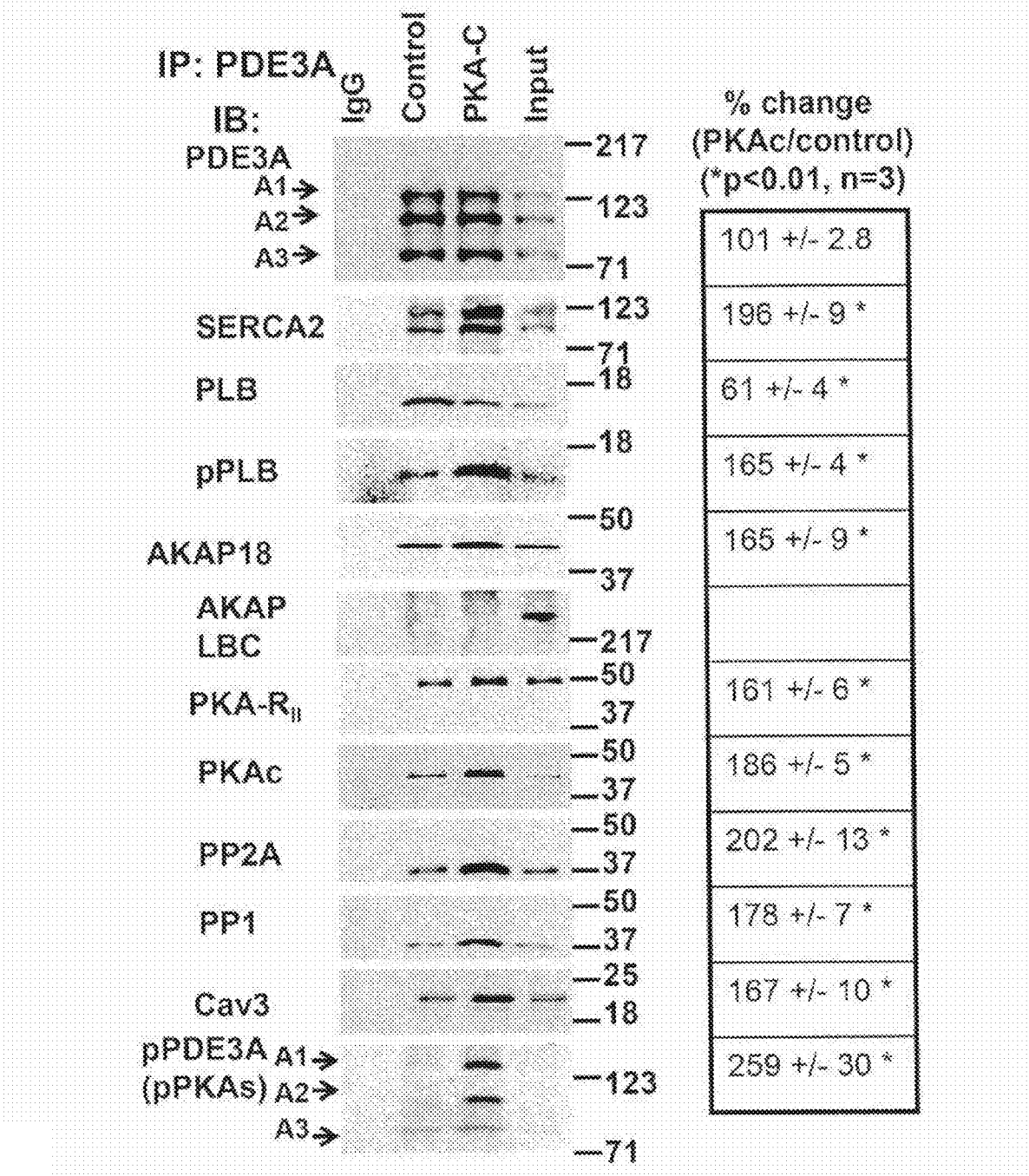
Figure 10. rPKAc promotes interactions of PDE3A with components of the SERCA2 regulatory signalosome.

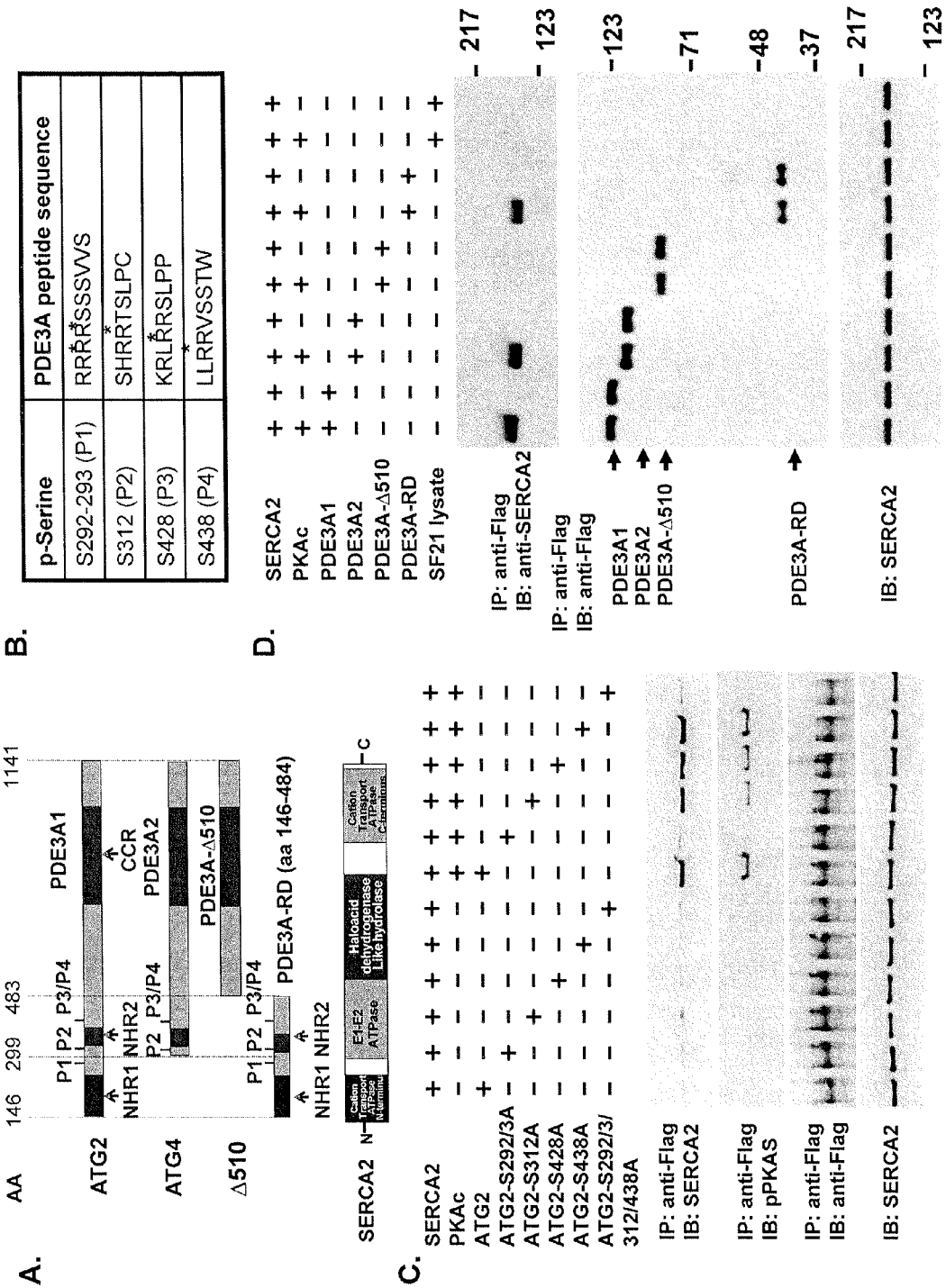
Figure 11A-D. rPKAc phosphorylates rhPDE3A and increases its interactions rSERCA2.

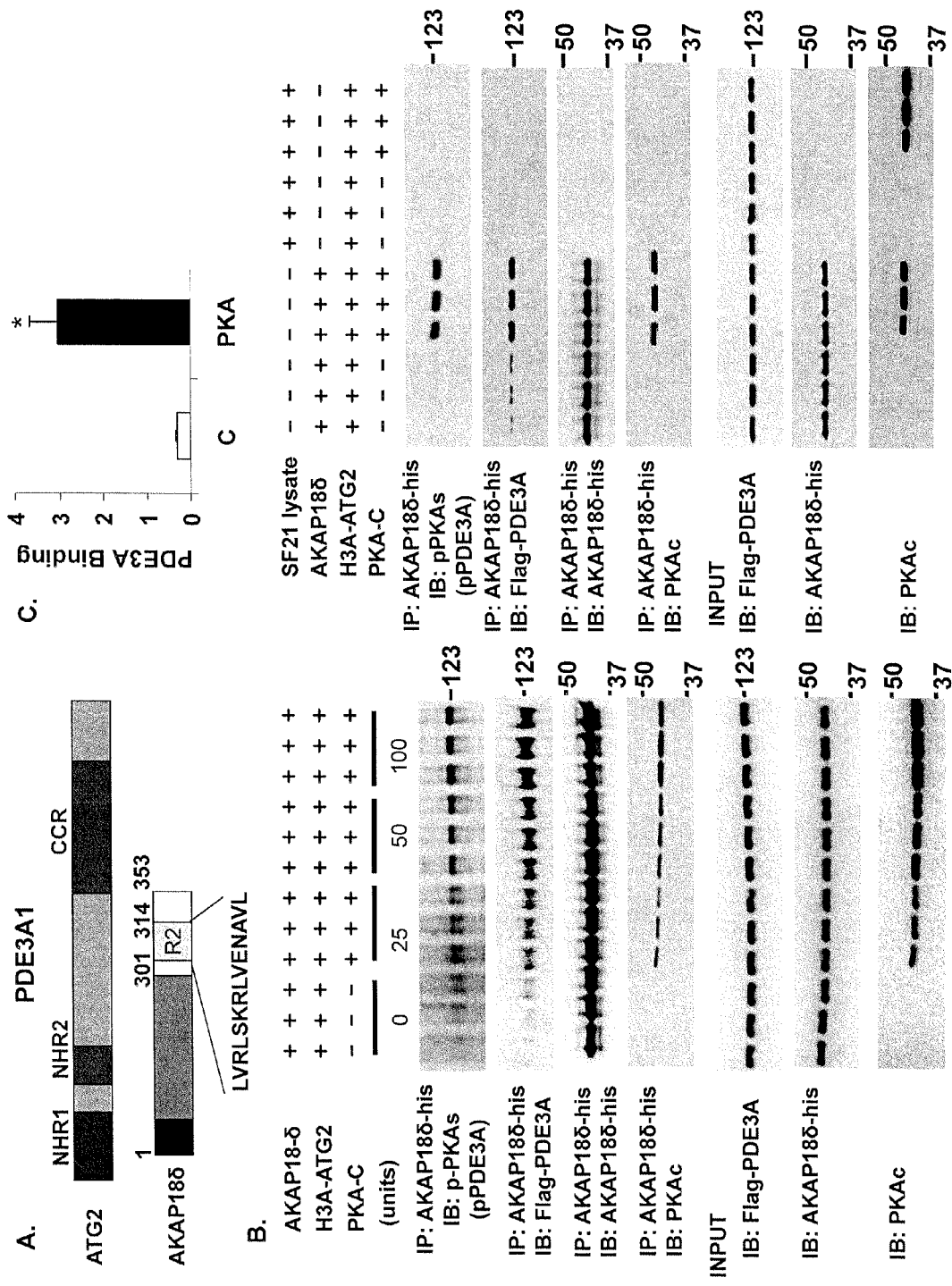
Figure 12A-C. rPKAc induced phosphorylation of rhPDE3A induces interaction with rat rAKAP18δ.

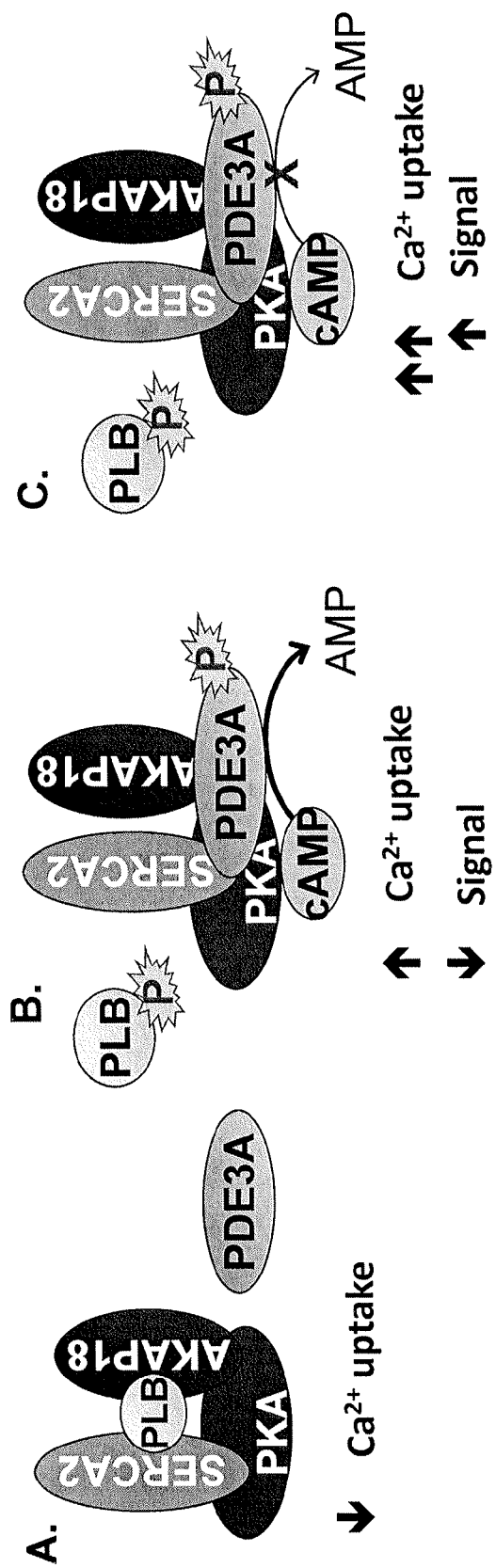
Figure 13A-C. Model of the regulation of SERCA2 activity by cAMP and the AKAP18 and PLB-containing signalosome.

SEQUENCE LISTING

```
<160> NUMBER OF SEQ ID NOS: 3

<210> SEQ ID NO 1
<211> LENGTH: 1141
<212> TYPE: PRT
<213> ORGANISM: Homo sapiens
```

```
<220> FEATURE:
<221> NAME/KEY: MISC_FEATURE
<222> LOCATION: (1)..(1141)
<223> OTHER INFORMATION: conceptual translation of the longest open
      reading frame (ORF) of the PDE3A gene
<220> FEATURE:
<221> NAME/KEY: MISC_FEATURE
<222> LOCATION: (146)..(1141)
<223> OTHER INFORMATION: PDE3A1 isoform sequence
<220> FEATURE:
<221> NAME/KEY: MISC_FEATURE
<222> LOCATION: (300)..(1141)
<223> OTHER INFORMATION: PDE3A2 isoform sequence
<220> FEATURE:
<221> NAME/KEY: MISC_FEATURE
<222> LOCATION: (484)..(1141)
<223> OTHER INFORMATION: PDE3A3 isoform sequence
<300> PUBLICATION INFORMATION:
<301> AUTHORS: Jeremy Wechsler, Young-Hun Choi, Judith Krall, Faiyaz
      Ahmad, Vincent C. Manganiello and Matthew A. Movsesian
<302> TITLE: Isoforms of Cyclic Nucleotide Phosphodiesterase PDE3A in
      Cardiac Myocytes
<303> JOURNAL: Journal of Biological Chemistry
<304> VOLUME: 277
<306> PAGES: 38072-38078
<307> DATE: 2002

<400> SEQUENCE: 1

Met Ala Val Pro Gly Asp Ala Ala Arg Val Arg Asp Lys Pro Val His
1               5                   10                  15

Ser Gly Val Ser Gln Ala Pro Thr Ala Gly Arg Asp Cys His His Arg
            20                  25                  30

Ala Asp Pro Ala Ser Pro Arg Asp Ser Gly Cys Arg Gly Cys Trp Gly
        35                  40                  45

Asp Leu Val Leu Gln Pro Leu Arg Ser Ser Arg Lys Leu Ser Ser Ala
    50                  55                  60

Leu Cys Ala Gly Ser Leu Ser Phe Leu Leu Ala Leu Leu Val Arg Leu
65                  70                  75                  80

Val Arg Gly Glu Val Gly Cys Asp Leu Glu Gln Cys Lys Glu Ala Ala
                85                  90                  95

Ala Ala Glu Glu Glu Glu Ala Ala Pro Gly Ala Glu Gly Gly Val Phe
            100                 105                 110

Pro Gly Pro Arg Gly Gly Ala Pro Gly Gly Ala Arg Leu Ser Pro
        115                 120                 125

Trp Leu Gln Pro Ser Ala Leu Leu Phe Ser Leu Leu Cys Ala Phe Phe
    130                 135                 140

Trp Met Gly Leu Tyr Leu Leu Arg Ala Gly Val Arg Leu Pro Leu Ala
145                 150                 155                 160

Val Ala Leu Leu Ala Ala Cys Cys Gly Gly Glu Ala Leu Val Gln Ile
                165                 170                 175

Gly Leu Gly Val Gly Glu Asp His Leu Leu Ser Leu Pro Ala Ala Gly
            180                 185                 190

Val Val Leu Ser Cys Leu Ala Ala Ala Thr Trp Leu Val Leu Arg Leu
        195                 200                 205

Arg Leu Gly Val Leu Met Ile Ala Leu Thr Ser Ala Val Arg Thr Val
    210                 215                 220

Ser Leu Ile Ser Leu Glu Arg Phe Lys Val Ala Trp Arg Pro Tyr Leu
225                 230                 235                 240

Ala Tyr Leu Ala Gly Val Leu Gly Ile Leu Leu Ala Arg Tyr Val Glu
                245                 250                 255

Gln Ile Leu Pro Gln Ser Ala Glu Ala Ala Pro Arg Glu His Leu Gly
            260                 265                 270
```

```
Ser Gln Leu Ile Ala Gly Thr Lys Glu Asp Ile Pro Val Phe Lys Arg
        275                 280                 285

Arg Arg Arg Ser Ser Val Val Ser Ala Glu Met Ser Gly Cys Ser
290                 295                 300

Ser Lys Ser His Arg Arg Thr Ser Leu Pro Cys Ile Pro Arg Glu Gln
305                 310                 315                 320

Leu Met Gly His Ser Glu Trp Asp His Lys Arg Gly Pro Arg Gly Ser
                325                 330                 335

Gln Ser Ser Gly Thr Ser Ile Thr Val Asp Ile Ala Val Met Gly Glu
            340                 345                 350

Ala His Gly Leu Ile Thr Asp Leu Leu Ala Asp Pro Ser Leu Pro Pro
                355                 360                 365

Asn Val Cys Thr Ser Leu Arg Ala Val Ser Asn Leu Leu Ser Thr Gln
    370                 375                 380

Leu Thr Phe Gln Ala Ile His Lys Pro Arg Val Asn Pro Val Thr Ser
385                 390                 395                 400

Leu Ser Glu Asn Tyr Thr Cys Ser Asp Ser Glu Ser Ser Glu Lys
                405                 410                 415

Asp Lys Leu Ala Ile Pro Lys Arg Leu Arg Arg Ser Leu Pro Pro Gly
            420                 425                 430

Leu Leu Arg Arg Val Ser Ser Thr Trp Thr Thr Thr Thr Ser Ala Thr
        435                 440                 445

Gly Leu Pro Thr Leu Glu Pro Ala Pro Val Arg Arg Asp Arg Ser Thr
    450                 455                 460

Ser Ile Lys Leu Gln Glu Ala Pro Ser Ser Pro Asp Ser Trp Asn
465                 470                 475                 480

Asn Pro Val Met Met Thr Leu Thr Lys Ser Arg Ser Phe Thr Ser Ser
                485                 490                 495

Tyr Ala Ile Ser Ala Ala Asn His Val Lys Ala Lys Gln Ser Arg
                500                 505                 510

Pro Gly Ala Leu Ala Lys Ile Ser Pro Leu Ser Ser Pro Cys Ser Ser
    515                 520                 525

Pro Leu Gln Gly Thr Pro Ala Ser Ser Leu Val Ser Lys Ile Ser Ala
        530                 535                 540

Val Gln Phe Pro Glu Ser Ala Asp Thr Thr Ala Lys Gln Ser Leu Gly
545                 550                 555                 560

Ser His Arg Ala Leu Thr Tyr Thr Gln Ser Ala Pro Asp Leu Ser Pro
                565                 570                 575

Gln Ile Leu Thr Pro Pro Val Ile Cys Ser Ser Cys Gly Arg Pro Tyr
                580                 585                 590

Ser Gln Gly Asn Pro Ala Asp Glu Pro Leu Glu Arg Ser Gly Val Ala
        595                 600                 605

Thr Arg Thr Pro Ser Arg Thr Asp Asp Thr Ala Gln Val Thr Ser Asp
    610                 615                 620

Tyr Glu Thr Asn Asn Asn Ser Asp Ser Ser Asp Ile Val Gln Asn Glu
625                 630                 635                 640

Asp Glu Thr Glu Cys Leu Arg Glu Pro Leu Arg Lys Ala Ser Ala Cys
                645                 650                 655

Ser Thr Tyr Ala Pro Glu Thr Met Met Phe Leu Asp Lys Pro Ile Leu
                660                 665                 670

Ala Pro Glu Pro Leu Val Met Asp Asn Leu Asp Ser Ile Met Glu Gln
    675                 680                 685
```

-continued

Leu Asn Thr Trp Asn Phe Pro Ile Phe Asp Leu Val Glu Asn Ile Gly
690                 695                 700

Arg Lys Cys Gly Arg Ile Leu Ser Gln Val Ser Tyr Arg Leu Phe Glu
705                 710                 715                 720

Asp Met Gly Leu Phe Glu Ala Phe Lys Ile Pro Ile Arg Glu Phe Met
            725                 730                 735

Asn Tyr Phe His Ala Leu Glu Ile Gly Tyr Arg Asp Ile Pro Tyr His
            740                 745                 750

Asn Arg Ile His Ala Thr Asp Val Leu His Ala Val Trp Tyr Leu Thr
            755                 760                 765

Thr Gln Pro Ile Pro Gly Leu Ser Thr Val Ile Asn Asp His Gly Ser
770                 775                 780

Thr Ser Asp Ser Asp Ser Asp Ser Gly Phe Thr His Gly His Met Gly
785                 790                 795                 800

Tyr Val Phe Ser Lys Thr Tyr Asn Val Thr Asp Asp Lys Tyr Gly Cys
            805                 810                 815

Leu Ser Gly Asn Ile Pro Ala Leu Glu Leu Met Ala Leu Tyr Val Ala
            820                 825                 830

Ala Ala Met His Asp Tyr Asp His Pro Gly Arg Thr Asn Ala Phe Leu
            835                 840                 845

Val Ala Thr Ser Ala Pro Gln Ala Val Leu Tyr Asn Asp Arg Ser Val
850                 855                 860

Leu Glu Asn His His Ala Ala Ala Trp Asn Leu Phe Met Ser Arg
865                 870                 875                 880

Pro Glu Tyr Asn Phe Leu Ile Asn Leu Asp His Val Glu Phe Lys His
            885                 890                 895

Phe Arg Phe Leu Val Ile Glu Ala Ile Leu Ala Thr Asp Leu Lys Lys
            900                 905                 910

His Phe Asp Phe Val Ala Lys Phe Asn Gly Lys Val Asn Asp Asp Val
            915                 920                 925

Gly Ile Asp Trp Thr Asn Glu Asn Asp Arg Leu Leu Val Cys Gln Met
930                 935                 940

Cys Ile Lys Leu Ala Asp Ile Asn Gly Pro Ala Lys Cys Lys Glu Leu
945                 950                 955                 960

His Leu Gln Trp Thr Asp Gly Ile Val Asn Glu Phe Tyr Glu Gln Gly
            965                 970                 975

Asp Glu Glu Ala Ser Leu Gly Leu Pro Ile Ser Pro Phe Met Asp Arg
            980                 985                 990

Ser Ala Pro Gln Leu Ala Asn Leu Gln Glu Ser Phe Ile Ser His Ile
            995                 1000                1005

Val Gly Pro Leu Cys Asn Ser Tyr Asp Ser Ala Gly Leu Met Pro
    1010                1015                1020

Gly Lys Trp Val Glu Asp Ser Asp Glu Ser Gly Asp Thr Asp Asp
    1025                1030                1035

Pro Glu Glu Glu Glu Glu Ala Pro Ala Pro Asn Glu Glu Glu
    1040                1045                1050

Thr Cys Glu Asn Asn Glu Ser Pro Lys Lys Lys Thr Phe Lys Arg
    1055                1060                1065

Arg Lys Ile Tyr Cys Gln Ile Thr Gln His Leu Leu Gln Asn His
    1070                1075                1080

Lys Met Trp Lys Lys Val Ile Glu Glu Glu Gln Arg Leu Ala Gly
    1085                1090                1095

Ile Glu Asn Gln Ser Leu Asp Gln Thr Pro Gln Ser His Ser Ser

```
               1100                1105                1110

Glu  Gln  Ile  Gln  Ala  Ile  Lys  Glu  Glu  Glu  Glu  Lys  Gly  Lys
         1115                1120                1125

Pro  Arg  Gly  Glu  Glu  Ile  Pro  Thr  Gln  Lys  Pro  Asp   Gln
    1130                1135                1140

<210> SEQ ID NO 2
<211> LENGTH: 1141
<212> TYPE: PRT
<213> ORGANISM: Homo sapiens
<220> FEATURE:
<221> NAME/KEY: MISC_FEATURE
<222> LOCATION: (1)..(1141)
<223> OTHER INFORMATION: conceptual translation of the longest ORF of
      the PDE3A gene with a mutation at amino acid position 1004 in
      which phenylalanine is changed to alanine; presence of alanine at
      amino acid 1004 inactivates phosphodiesterase activity

<400> SEQUENCE: 2

Met  Ala  Val  Pro  Gly  Asp  Ala  Ala  Arg  Val  Arg  Asp  Lys  Pro  Val  His
1                 5                   10                  15

Ser  Gly  Val  Ser  Gln  Ala  Pro  Thr  Ala  Gly  Arg  Asp  Cys  His  His  Arg
             20                  25                  30

Ala  Asp  Pro  Ala  Ser  Pro  Arg  Asp  Ser  Gly  Cys  Arg  Gly  Cys  Trp  Gly
         35                  40                  45

Asp  Leu  Val  Leu  Gln  Pro  Leu  Arg  Ser  Ser  Arg  Lys  Leu  Ser  Ser  Ala
 50                  55                  60

Leu  Cys  Ala  Gly  Ser  Leu  Ser  Phe  Leu  Leu  Ala  Leu  Leu  Val  Arg  Leu
 65                  70                  75                  80

Val  Arg  Gly  Glu  Val  Gly  Cys  Asp  Leu  Glu  Gln  Cys  Lys  Glu  Ala  Ala
             85                  90                  95

Ala  Ala  Glu  Glu  Glu  Ala  Ala  Pro  Gly  Ala  Glu  Gly  Gly  Val  Phe
         100                 105                 110

Pro  Gly  Pro  Arg  Gly  Gly  Ala  Pro  Gly  Gly  Gly  Ala  Arg  Leu  Ser  Pro
             115                 120                 125

Trp  Leu  Gln  Pro  Ser  Ala  Leu  Leu  Phe  Ser  Leu  Leu  Cys  Ala  Phe  Phe
         130                 135                 140

Trp  Met  Gly  Leu  Tyr  Leu  Leu  Arg  Ala  Gly  Val  Arg  Leu  Pro  Leu  Ala
145                 150                 155                 160

Val  Ala  Leu  Leu  Ala  Ala  Cys  Cys  Gly  Gly  Glu  Ala  Leu  Val  Gln  Ile
             165                 170                 175

Gly  Leu  Gly  Val  Gly  Glu  Asp  His  Leu  Leu  Ser  Leu  Pro  Ala  Ala  Gly
             180                 185                 190

Val  Val  Leu  Ser  Cys  Leu  Ala  Ala  Ala  Thr  Trp  Leu  Val  Leu  Arg  Leu
             195                 200                 205

Arg  Leu  Gly  Val  Leu  Met  Ile  Ala  Leu  Thr  Ser  Ala  Val  Arg  Thr  Val
         210                 215                 220

Ser  Leu  Ile  Ser  Leu  Glu  Arg  Phe  Lys  Val  Ala  Trp  Arg  Pro  Tyr  Leu
225                 230                 235                 240

Ala  Tyr  Leu  Ala  Gly  Val  Leu  Gly  Ile  Leu  Leu  Ala  Arg  Tyr  Val  Glu
             245                 250                 255

Gln  Ile  Leu  Pro  Gln  Ser  Ala  Glu  Ala  Ala  Pro  Arg  Glu  His  Leu  Gly
         260                 265                 270

Ser  Gln  Leu  Ile  Ala  Gly  Thr  Lys  Glu  Asp  Ile  Pro  Val  Phe  Lys  Arg
         275                 280                 285

Arg  Arg  Arg  Ser  Ser  Ser  Val  Val  Ser  Ala  Glu  Met  Ser  Gly  Cys  Ser
         290                 295                 300
```

-continued

```
Ser Lys Ser His Arg Arg Thr Ser Leu Pro Cys Ile Pro Arg Glu Gln
305                 310                 315                 320

Leu Met Gly His Ser Glu Trp Asp His Lys Arg Gly Pro Arg Gly Ser
            325                 330                 335

Gln Ser Ser Gly Thr Ser Ile Thr Val Asp Ile Ala Val Met Gly Glu
        340                 345                 350

Ala His Gly Leu Ile Thr Asp Leu Leu Ala Asp Pro Ser Leu Pro Pro
            355                 360                 365

Asn Val Cys Thr Ser Leu Arg Ala Val Ser Asn Leu Leu Ser Thr Gln
    370                 375                 380

Leu Thr Phe Gln Ala Ile His Lys Pro Arg Val Asn Pro Val Thr Ser
385                 390                 395                 400

Leu Ser Glu Asn Tyr Thr Cys Ser Asp Ser Glu Glu Ser Ser Glu Lys
                405                 410                 415

Asp Lys Leu Ala Ile Pro Lys Arg Leu Arg Arg Ser Leu Pro Pro Gly
            420                 425                 430

Leu Leu Arg Arg Val Ser Ser Thr Trp Thr Thr Thr Thr Ser Ala Thr
        435                 440                 445

Gly Leu Pro Thr Leu Glu Pro Ala Pro Val Arg Arg Asp Arg Ser Thr
450                 455                 460

Ser Ile Lys Leu Gln Glu Ala Pro Ser Ser Pro Asp Ser Trp Asn
465                 470                 475                 480

Asn Pro Val Met Met Thr Leu Thr Lys Ser Arg Ser Phe Thr Ser Ser
                485                 490                 495

Tyr Ala Ile Ser Ala Ala Asn His Val Lys Ala Lys Lys Gln Ser Arg
                500                 505                 510

Pro Gly Ala Leu Ala Lys Ile Ser Pro Leu Ser Ser Pro Cys Ser Ser
            515                 520                 525

Pro Leu Gln Gly Thr Pro Ala Ser Ser Leu Val Ser Lys Ile Ser Ala
        530                 535                 540

Val Gln Phe Pro Glu Ser Ala Asp Thr Thr Ala Lys Gln Ser Leu Gly
545                 550                 555                 560

Ser His Arg Ala Leu Thr Tyr Thr Gln Ser Ala Pro Asp Leu Ser Pro
                565                 570                 575

Gln Ile Leu Thr Pro Pro Val Ile Cys Ser Ser Cys Gly Arg Pro Tyr
            580                 585                 590

Ser Gln Gly Asn Pro Ala Asp Glu Pro Leu Glu Arg Ser Gly Val Ala
        595                 600                 605

Thr Arg Thr Pro Ser Arg Thr Asp Asp Thr Ala Gln Val Thr Ser Asp
610                 615                 620

Tyr Glu Thr Asn Asn Ser Asp Ser Ser Asp Ile Val Gln Asn Glu
625                 630                 635                 640

Asp Glu Thr Glu Cys Leu Arg Glu Pro Leu Arg Lys Ala Ser Ala Cys
                645                 650                 655

Ser Thr Tyr Ala Pro Glu Thr Met Met Phe Leu Asp Lys Pro Ile Leu
            660                 665                 670

Ala Pro Glu Pro Leu Val Met Asp Asn Leu Asp Ser Ile Met Glu Gln
        675                 680                 685

Leu Asn Thr Trp Asn Phe Pro Ile Phe Asp Leu Val Glu Asn Ile Gly
        690                 695                 700

Arg Lys Cys Gly Arg Ile Leu Ser Gln Val Ser Tyr Arg Leu Phe Glu
705                 710                 715                 720
```

-continued

Asp Met Gly Leu Phe Glu Ala Phe Lys Ile Pro Ile Arg Glu Phe Met
            725                 730                 735

Asn Tyr Phe His Ala Leu Glu Ile Gly Tyr Arg Asp Ile Pro Tyr His
        740                 745                 750

Asn Arg Ile His Ala Thr Asp Val Leu His Ala Val Trp Tyr Leu Thr
            755                 760                 765

Thr Gln Pro Ile Pro Gly Leu Ser Thr Val Ile Asn Asp His Gly Ser
        770                 775                 780

Thr Ser Asp Ser Asp Ser Ser Gly Phe Thr His Gly His Met Gly
785                 790                 795                 800

Tyr Val Phe Ser Lys Thr Tyr Asn Val Thr Asp Asp Lys Tyr Gly Cys
                805                 810                 815

Leu Ser Gly Asn Ile Pro Ala Leu Glu Leu Met Ala Leu Tyr Val Ala
            820                 825                 830

Ala Ala Met His Asp Tyr Asp His Pro Gly Arg Thr Asn Ala Phe Leu
        835                 840                 845

Val Ala Thr Ser Ala Pro Gln Ala Val Leu Tyr Asn Asp Arg Ser Val
    850                 855                 860

Leu Glu Asn His His Ala Ala Ala Trp Asn Leu Phe Met Ser Arg
865                 870                 875                 880

Pro Glu Tyr Asn Phe Leu Ile Asn Leu Asp His Val Glu Phe Lys His
                885                 890                 895

Phe Arg Phe Leu Val Ile Glu Ala Ile Leu Ala Thr Asp Leu Lys Lys
            900                 905                 910

His Phe Asp Phe Val Ala Lys Phe Asn Gly Lys Val Asn Asp Asp Val
        915                 920                 925

Gly Ile Asp Trp Thr Asn Glu Asn Asp Arg Leu Leu Val Cys Gln Met
    930                 935                 940

Cys Ile Lys Leu Ala Asp Ile Asn Gly Pro Ala Lys Cys Lys Glu Leu
945                 950                 955                 960

His Leu Gln Trp Thr Asp Gly Ile Val Asn Glu Phe Tyr Glu Gln Gly
                965                 970                 975

Asp Glu Glu Ala Ser Leu Gly Leu Pro Ile Ser Pro Phe Met Asp Arg
            980                 985                 990

Ser Ala Pro Gln Leu Ala Asn Leu Gln Glu Ser Ala Ile Ser His Ile
        995                 1000                1005

Val Gly Pro Leu Cys Asn Ser Tyr Asp Ser Ala Gly Leu Met Pro
        1010                1015                1020

Gly Lys Trp Val Glu Asp Ser Asp Glu Ser Gly Asp Thr Asp Asp
        1025                1030                1035

Pro Glu Glu Glu Glu Glu Ala Pro Ala Pro Asn Glu Glu Glu
        1040                1045                1050

Thr Cys Glu Asn Asn Glu Ser Pro Lys Lys Lys Thr Phe Lys Arg
        1055                1060                1065

Arg Lys Ile Tyr Cys Gln Ile Thr Gln His Leu Leu Gln Asn His
        1070                1075                1080

Lys Met Trp Lys Lys Val Ile Glu Glu Glu Gln Arg Leu Ala Gly
        1085                1090                1095

Ile Glu Asn Gln Ser Leu Asp Gln Thr Pro Gln Ser His Ser Ser
        1100                1105                1110

Glu Gln Ile Gln Ala Ile Lys Glu Glu Glu Glu Lys Gly Lys
        1115                1120                1125

Pro Arg Gly Glu Glu Ile Pro Thr Gln Lys Pro Asp Gln

```
<210> SEQ ID NO 3
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)

<400> SEQUENCE: 3

Gly Arg Thr Gly Arg Arg Asn Ser Ile
1               5
```

METHODS FOR MODULATING CYCLIC NUCLEOTIDE-MEDIATED SIGNALING IN CARDIAC MYOCYTES AND COMPOSITIONS

This patent application claims the benefit of the filing date of U.S. Ser. No. 62/024,994, filed Jul. 15, 2014, the contents of which are herein incorporated by reference in their entirety into the present patent application.

This invention was made with government support under Grant No. CARA-029-09F awarded by the United States Department of Veterans Affairs. The government has certain rights in the invention.

Throughout this application various publications are referenced. The disclosures of these publications in their entireties are hereby incorporated by reference into this application in order to more fully describe the state of the art to which this invention pertains.

BACKGROUND OF THE INVENTION

PDE3 and the Regulation of Myocardial Contractility

Cyclic nucleotide phosphodiesterases regulate intracellular signaling by hydrolyzing cAMP and/or cGMP. By blocking their hydrolysis, phosphodiesterase inhibitors potentiate cyclic nucleotide-mediated signaling. Eleven families of these enzymes have been described[1]. Two subfamilies, PDE3A and PDE3B, have been identified[2,3]. Myocardial contractility is regulated by PDE3A, and Pde3a ablation in mice increases the phosphorylation of two sarcoplasmic reticulum proteins involved in intracellular $Ca^{2+}$ cycling: phosphorylation of phospholamban (PL or PLB) which stimulates the activity of the $Ca^{2+}$-transporting ATPase of the sarcoplasmic reticulum (SERCA2), increasing $Ca^{2+}$ uptake during diastole, and phosphorylation of ryanodine-sensitive $Ca^{2+}$ channels which increases $Ca^{2+}$ release from the sarcoplasmic reticulum during systole[4-6] (FIG. 1). These changes in protein phosphorylation augment myocardial contractility by increasing the amplitude of intracellular $Ca^{2+}$ transients[6]. The role of PDE3A in regulating $Ca^{2+}$ uptake by the sarcoplasmic reticulum is likely to be linked to its integration into an intracellular signaling complex that includes SERCA2, AKAP18, phospholamban and PKA[6].

PDE3 Inhibition in Heart Failure

In dilated cardiomyopathy, decreases in myocardial β-adrenergic receptor density, together with increases in Gαi and β-adrenergic receptor kinase activity, attenuate the stimulation of adenylyl cyclase by catecholamines, leading to decreases in myocardial cAMP content and intracellular $Ca^{2+}$ transient amplitude[7-16]. PDE3 inhibitors are used to 'overcome' this reduction in intracellular cAMP content and increase cAMP-mediated signaling in failing myocardium. In the short term, PDE3 inhibitors raise cardiac output and lower left ventricular filling pressures[17-23]. With long-term administration, however, these benefits are outweighed by an increase in sudden cardiac death[24]. While our knowledge regarding the mechanisms is limited, they appear to be separate from those that augment contractility: an increase in SERCA2 activity, the consequence of phospholamban phosphorylation (FIG. 1), has anti-arrhythmic effects in animal models of ischemia/reperfusion and chronic heart failure[25,26]. Pro-apoptotic consequences of PDE3 inhibition, though, are likely to contribute to pathologic remodeling in dilated cardiomyopathy[27]. PDE3 inhibition in rats and Pde3a ablation in mice lead to increases in the phosphorylation of cAMP response element-binding protein (CREB) and consequent increases in the expression of inducible cAMP early repressors (ICER's), promoting apoptosis (FIG. 1)[6,28,29]. Conversely, PDE3A overexpression in mice reduces ICER, increases Bcl-2 expression and reduces apoptosis following ischemia/reperfusion injury (but reduces myocardial contractility)[30].

Alternative Path Ways for cAMP-Mediated Protein Phosphorylation

Until now, studies of the contractile and pro-apoptotic effects of PDE3 inhibition have focused principally on substrates of PKA, which is activated directly by cAMP. More recently, it has become clear that the effects of cAMP are also mediated by guanine-nucleotide-exchange proteins activated by cAMP (Epacs), which influence protein phosphorylation through diverse mechanisms (FIG. 2)[31,32]. In cardiac myocytes, Epac activation augments contractility through signaling pathways that increase the phosphorylation of ryanodine-sensitive $Ca^{2+}$ channels of the sarcoplasmic reticulum by $Ca^{2+}$/calmodulin-activated protein kinase II (CamKII)—which was seen in pde3a$^{-/-}$ mice[1]—and of sarcomeric proteins such as cardiac myosin-binding protein C and troponin I by CamKII and protein kinase C (PKC)[32-36]. Epac activation also has pro-hypertrophic actions that result, at least in part, from the activation of CamKII, as well as the protein phosphatase calcineurin[37,38]. These observations indicate that changes in intracellular cAMP are likely to affect the phosphorylation of a large number of proteins that may contribute to the beneficial and adverse effects of PDE3 inhibition. A recent study of responses to β-adrenergic receptor activation in mouse embryonic fibroblast cells showed both increases and decreases in protein phosphorylation[39], and, in our experiments, exposure of cultured cells to agents that stimulate cAMP-mediated signaling resulted in both increases and decreases in protein phosphorylation, covering both PKA and non-PKA sites. Interactions between PDE3B and Epac have been identified in vascular smooth muscle myocytes[40], and peptides that disrupt this interaction activate Epac and lead to the activation of phosphoinositide-3-kinase-γ (PI3Kγ), extracellular signal-related kinase (ERK) and protein kinase B (PKB, also known as Akt)[41], but the role of PDE3 in regulating Epac-mediated protein phosphorylation in cardiac myocytes remains unexplored. cAMP can also regulate L-type $Ca^{2+}$ channels directly[42], and Epac activation induces other responses in addition to protein phosphorylation[31].

Individual Phosphodiesterases Regulate cAMP-Mediated Signaling in Distinct Intracellular Compartments of Cardiac Myocytes In this context, it is noteworthy that cAMP content is regulated differentially in spatially and functionally distinct compartments of cardiac myocytes, a phenomenon referred to as the 'compartmentation' of cAMP-mediated signaling. It has long been known that exposure to β-adrenergic receptor agonists increases cAMP content in cytosolic and microsomal fractions of cardiac muscle and augments contractility, while exposure to prostaglandin E1 (PGE1) increases cAMP content only in cytosolic fractions, without inotropic effects[43,44]. This compartmentation of cAMP-mediated signaling is altered in a rat model of heart failure following a redistribution of β-adrenergic receptor subtypes within cell membranes[45], and is a feature of the pathophysiology of dilated cardiomyopathy in humans (both ischemic and nonischemic), where the reduction in cAMP content is much more pronounced in microsomes than in cytosolic fractions (FIG. 3)[15].

Over the past decade, the prominent involvement of phosphodiesterases in this compartmentation has become apparent. In rat cardiac myocytes, β-adrenergic receptor agonists induce increases in intracellular cAMP content that are highly localized[46]. Individual phosphodiesterases, which are targeted by protein-protein interactions to specific intracellular domains, have distinct roles. In rat heart, PDE4 has a greater role than PDE3 in regulating glucagon and catecholamine-mediated increases in intracellular cAMP content, while PDE3 has a greater role in regulating forskolin-induced increases[47,48]. PDE2 has a major role in regulating β-adrenergic receptor-mediated increases in intracellular cAMP content but only a small role in regulating forskolin-induced increases, and PDE2 and PDE3 regulate 'opposing' effects of cGMP on cAMP-mediated signaling in rat heart in functionally separate compartments[49,50].

These studies focused on phosphodiesterase families, but individual isoforms within a family have precise roles in specific intracellular microdomains. This has been examined extensively in the PDE4 family. PDE4D3 is present in multiprotein complexes regulating KCNQ1/KCNE1 $K^+$ channels and ryanodine-sensitive $Ca^{2+}$ channels[51,52]. The latter are hyperphosphorylated in Pde4d$^{-/-}$ mice, leading to abnormalities of sarcoplasmic-reticulum $Ca^{2+}$ release associated with arrhythmias and the development of dilated cardiomyopathy[52]. In contrast, experiments in Pde4d$^{-/-}$ and Pde4b$^{-/-}$ mice showed that the stimulation of L-type $Ca^{2+}$ currents by β-adrenergic receptor agonists is controlled specifically by PDE4B[53]. These unique roles for PDE4 variants derive principally from the differences in their intracellular localization, which in turn reflect the distinct protein-protein interactions through which they are recruited to intracellular signaling complexes with a range of proteins, including AKAP's, β-arrestins, Src, Lyn and Fyn[54,55].

Multiple Isoforms of PDE3 are Expressed in Human Myocardium

In human cardiac myocytes, the PDE3A gene gives rise, through a combination of transcription and translation from alternative sites, to several isoforms whose amino-acid sequences are identical save for the presence of different lengths of N-terminal sequence that are involved in intracellular localization, protein-protein interactions and allosteric regulation of catalytic activity, which resides in the C-terminus (FIG. 4)[56]. PDE3A1, a 136-kDa protein, has a unique N-terminal extension containing hydrophobic loops that insert into intracellular membranes[57,58], and three known sites of phosphorylation, S293, S312 and S428[59-61]. PDE3A2, a 118-kDa protein transcribed from a downstream site in exon 1, lacks the N-terminal extension and S293. PDE3A3, which is translated from a downstream site in the PDE3A2 mRNA, is a 94-kDa protein that lacks all of these phosphorylation sites. The PDE3B gene gives rise to a single 146-kDa protein, whose domain organization resembles that of PDE3A1. Its C-terminal catalytic region is highly homologous to that of PDE3A1, and it contains an N-terminal hydrophobic sequence and phosphorylation sites similar to two of the three sites identified in PDE3A1[62,63]. In view of their C-terminal sequence identity (for PDE3A1, PDE3A2 and PDE3A3) and homology (PDE3B), all four isoforms are similar with respect to their basal catalytic activity and sensitivity to existing PDE3 inhibitors[64].

The Potential Opportunity and its Clinical Impact

The American Heart Association estimates that 5.7 million Americans have heart failure. Each year, >550,000 new cases are diagnosed, among which ~50% involve impaired contractility. The annual hospitalization rate is >1 million, and annual mortality is >270,000[65,66]. An agent that could inhibit cardiac diseases such as hypertrophy and increase survival would represent a major advance, and its clinical impact would be immense. While the benefit might be greatest for patients with advanced heart failure who are poor candidates for ventricular assist devices, artificial hearts and heart transplantation—which includes the ever-increasing population of aging patients with comorbidities that are contraindications for surgery—a large proportion of patients with NYHA class 3 or 4 symptoms could be expected to benefit. Our discovery provides a novel approach to this enormously important clinical problem.

SUMMARY OF THE INVENTION

The invention provides for an isolated or purified peptide, polypeptide or peptidomimetic possessing anti-hypertrophic activity in a cardiac myocyte. In one embodiment, the polypeptide may be a mutant derived from wild-type PDE3A1 protein. The wild-type PDE3A1 protein may have the amino acid sequence given in SEQ ID NO:1 at amino acid position 146 to 1141.

The invention also provides a peptidomimetic possessing an anti-hypertrophic activity in a cardiac myocyte, wherein the peptidomimetic mimics a structure or part of a structure formed by a polypeptide derived from the amino terminus of wild-type PDE3A1 at amino acid position 146 to 668 in SEQ ID NO:1.

The invention further provides a peptidomimetic possessing an anti-hypertrophic activity in a cardiac myocyte, wherein the peptidomimetic mimics a structure or part of a structure formed by an amino-terminal polypeptide present in wild-type PDE3A1 but not in PDE3A3, corresponding to amino acid position 146 to 483 in SEQ ID NO:1.

Additionally, the invention provides a peptidomimetic possessing an anti-hypertrophic activity in a cardiac myocyte, wherein the peptidomimetic mimics a structure or part of a structure formed by an amino-terminal polypeptide present in wild-type PDE3A1 but not in PDE3A2, corresponding to amino acid position 146 to 299 in SEQ ID NO:1; or alternatively, the peptidomimetic mimics a structure or part of a structure formed by wild-type PDE3A1 from amino acid position 300 to 1141 in SEQ ID NO:1, in which the structure or part of the structure is different in PDE3A2; or alternatively, the peptidomimetic mimics a structure or part of a structure having greater accessibility for protein-protein interactions in wild-type PDE3A1 than in PDE3A2, corresponding to amino acid position 300 to 1141 in SEQ ID NO:1; or alternatively, the peptidomimetic mimics a structure or part of a structure of phospho-PDE3A1 at a serine residue unique to PDE3A1 protein or phosphorylated selectively or differentially in wild-type PDE3A1 and PDE3A2 proteins.

The invention also provides a polypeptide having the ability to avoid pro-hypertrophic effect of conventional PDE3 inhibition in a cardiac myocyte. In one embodiment, the polypeptide may be a mutant variant derived from wild-type PDE3A1 protein and wherein the wild-type PDE3A1 protein has the amino acid sequence given in SEQ ID NO:1 at amino acid position 146 to 1141.

The invention further provides nucleic acid molecules encoding a polypeptide possessing anti-hypertrophic activity in a cardiac myocyte. In one embodiment, the nucleic acid molecule is DNA (e.g., cDNA) or a hybrid thereof. Alternatively, the nucleic acid molecule is RNA or a hybrid thereof.

Additionally, the invention provides a vector, which comprises the nucleotide sequences of the invention. A host vector system is also provided. The host vector system comprises the vector of the invention in a suitable host cell.

Examples of suitable host cells include, but are not limited to, prokaryotic and eukaryotic cells.

The invention also provides a peptidomimetic to avoid or counter pro-hypertrophic effect of conventional PDE3 inhibition in a cardiac myocyte, wherein the peptidomimetic mimics a structure or part of a structure formed by a polypeptide derived from the amino terminus of wild-type PDE3A1 at amino-acid position 146 to 668 in SEQ ID NO: 1.

The invention further provides a peptidomimetic to avoid or counter pro-hypertrophic effect of conventional PDE3 inhibition in a cardiac myocyte, wherein the peptidomimetic mimics a structure or part of a structure formed by an amino-terminal polypeptide present in wild-type PDE3A1 but not in PDE3A3, corresponding to amino acid position 146 to 483 in SEQ ID NO:1.

The invention also provides a peptidomimetic to avoid or counter pro-hypertrophic effect of conventional PDE3 inhibition in a cardiac myocyte, wherein the peptidomimetic mimics a structure or part of a structure formed by an amino-terminal polypeptide present in wild-type PDE3A1 but not in PDE3A2, corresponding to amino acid position 146 to 299 in SEQ ID NO:1; or alternatively, the peptidomimetic mimics a structure or part of a structure formed by wild-type PDE3A1 from amino acid position 300 to 1141 in SEQ ID NO:1, in which the structure or part of the structure is different in PDE3A2; or alternatively, the peptidomimetic mimics a structure or part of a structure having greater accessibility for protein-protein interactions in wild-type PDE3A1 than in PDE3A2, corresponding to amino-acid position 300 to 1141 in SEQ ID NO: 1; or alternatively, the peptidomimetic mimics a structure or part of a structure of phospho-PDE3A1 at a serine residue unique to PDE3A1 protein or differentially phosphorylated between wild-type PDE3A1 and PDE3A2 proteins.

The invention also provides methods of preventing, inhibiting or reversing hypertrophy in a cardiac myocyte. The method comprises contacting the cell with a peptide, polypeptide or peptidomimetic of the invention.

The invention further provides methods of avoiding pro-hypertrophic effect of conventional PDE3 inhibition in a cardiac myocyte. The method comprises contacting the cell with a peptide, polypeptide or a peptidomimetic of the invention.

The invention also provides methods for preventing, inhibiting or reversing myocardial hypertrophy in a subject. The method comprises administering to the subject a peptide, peptidomimetic or small molecule that interacts with a PDE3-interacting protein that affects myocardial hypertrophy in an amount effective so as to prevent, inhibit or reverse myocardial hypertrophy, thereby preventing, inhibiting or reversing myocardial hypertrophy in a subject.

The invention also provides methods for obtaining a beneficial effect of PDE3 inhibition in a subject with reduced or no adverse effect, wherein the subject is treated with a PDE3 isoform-specific or isoform-selective inhibitor.

The invention further provides methods for increasing selectivity of PDE3 inhibition in a cardiac myocyte, wherein such method comprises contacting the cardiac myocyte with a peptide, peptidomimetic or small molecule that interacts with a PDE3-interacting protein selective for a PDE3 isoform, or alternatively, contacting, expressing in or introducing in the cardiac myocyte a catalytically compromised, reduced or inactive form of a PDE3 isoform or its derivative, so as to selectively inhibit the PDE3 isoform, thereby increasing selectivity of PDE3 inhibition in a cardiac myocyte.

The invention also provides methods for selectively inhibiting a PDE3 isoform. The method comprises introduction or expression of an altered or mutated version of the PDE3 isoform to be selectively inhibited in a cell and wherein the altered or mutated version of the PDE3 isoform has altered protein-protein interaction or has altered or mutated catalytic activity.

Additionally, the invention provides methods for selectively altering cAMP level within a cellular compartment. The method comprises introduction or expression of an altered or mutated version of a PDE3 isoform associated with the cellular compartment and wherein the altered or mutated version of the PDE3 isoform has altered protein-protein interaction or has altered or mutated catalytic activity.

The invention also provides methods for eliciting positive inotropic response in a subject without myocardial hypertrophy or for eliciting positive inotropic and myocardial anti-hypertrophic responses in a subject. The method comprises administering to the subject any one of agents of the invention. The agents may be an agent that selectively decreases PDE3A1 activity in a cardiac myocyte; a peptide, a peptidomimetic or small molecule that mimics PDE3A1 amino terminus; a peptide, peptidomimetic or small molecule that interacts with a PDE3A1-interacting protein that selectively affects cAMP level in the intracellular compartment associated with PDE3A1 so as to increase $Ca^{2+}$ uptake from cytosol to sarcoplasmic reticulum during diastole and increase $Ca^{2+}$ release from sarcoplasmic reticulum during systole; a gene therapy vector for the delivery and/or expression of a catalytically compromised, reduced or inactive PDE3A1 mutant gene so as to selectively increase cAMP locally in an intracellular compartment associated with endogenous PDE3A1 protein, thereby eliciting positive inotropic response in a subject without myocardial hypertrophy or for eliciting positive inotropic and myocardial anti-hypertrophic responses in a subject.

BRIEF DESCRIPTION OF THE FIGURES

FIG. 1. Inotropic and pro-apoptotic actions of cAMP regulated by PDE3A in cardiac myocytes. Phosphorylation of membrane-associated proteins stimulates $Ca^{2+}$ cycling by the sarcoplasmic reticulum, while phosphorylation of transcription factors stimulates ICER expression. (A-kinase anchoring proteins—'AKAPs'—localize PKA to multiprotein complexes.)

FIG. 2. Alternative pathways for cAMP-mediated signaling. Epac activation by cAMP leads to the activation of protein kinases and phosphatases implicated in inotropic, pro-arrhythmic and hypertrophic responses.

FIG. 3. Compartment-selective decrease in intracellular cAMP content in failing human myocardium.

FIG. 4. PDE3 isoforms in cardiac myocytes.

FIG. 5. Anti-hypertrophic actions of PDE3A1-selective targeting in neonatal rat ventricular myocytes. Conventional PDE3 inhibitors (e.g., cilostamide) promote myocyte hypertrophy (left). Transfection with a dominant-negative PDE3A1 construct does not promote hypertrophy, and blocks the hypertrophic responses to norepinephrine ('NE') (center). Transfection with a dominant-negative PDE3A2 construct does not have this effect (right).

FIG. 6 a-b. PDE3A, SERCA2, PLB, AKAP18, co-localize in the Z-bands in normal human myocardium. A. Cryostat sections of normal human left ventricle were permeabilized and incubated with rabbit anti-PDE3A-CT, anti-desmin, anti-SERCA2, anti-PLB, anti-AKAP18 and antimyomesin or the other indicated primary antibodies, followed by incubation with Alexa Fluor® 488- or 594-conjugated anti-mouse or anti-rabbit secondary antibodies. Signals were detected with a Zeiss LSM510 laser scanning confocal microscope. Green fluorescence staining for PDE3A (FIG. 6 A); DAPI staining of nuclei (blue); Red fluorescent staining for marker proteins: Desmin, PLB, SERCA2, AKAP18 and myomesin. Fourth panel: merged images of PDE3A, marker proteins, and DAPI. PDE3A exhibits a striated pattern and co-localizes with desmin, SERCA2, PLB and AKAP18. B. Merged images from stacks of 10-15 sections (with 1 µm intervals) reveal colocalization of PDE3A with desmin, SERCA2, PLB, AKAP18, but not with myomesin (labeling M-line Red). X-Y (center), above X-Z (top), and Y-Z (right) planes are at indicated positions. Representative images from 3 independent experiments are shown.

FIG. 7 a-f. cAMP, PKA, and PDE3-inhibition increase SERCA2 activity and $Ca^{2+}$ uptake. A. After incubation of SR fractions (20 µg) in the absence or presence of the indicated concentrations of ATP and/or cAMP, without or with cilostamide or rolipram, endogenous PLB, phosphorylated PLB, and ρ-actin were detected after SDS-PAGE and immunoblotting. Data are representative of three experiments. In these and other Western blots, PLB is predominantly monomeric, most likely due to the heating of samples, prior to electrophoresis, under reducing conditions (buffer containing β-mercatoethanol, DTT, and SDS). B. Bar graph summarizing pSer16PLB/PLB total ratios. *P<0.01 vs. control (n=3 independent experiments). C. PDE activity in human cardiac SR fractions, expressed as specific activity (pmol cAMP hydrolyzed/min/mg). Results are presented as mean+/−SEM (n=3 preparations). PDE3 activity was determined as the cilostamide-sensitive fraction, and PDE4 activity as the rolipram-sensitive fraction. PDE3 activity is significantly higher than PDE4 activity (*P<0.001). D. After incubation of SR fractions without or with the indicated concentrations of cAMP (0-10 µM), $^{45}Ca^{2+}$ uptake was measured in the presence of 0.5 µM free $Ca^{2+}$. Results are presented as % increase due to cAMP, with basal $Ca^{2+}$ uptake (9.4+/−0.8 nmol/mg/min, n=3) taken as 100%. E. After incubation of SR fractions with or without cAMP (3 µM) in the presence or absence of cilostamide (1 µM), $^{45}Ca^{2+}$ uptake was assayed as described above. Results are presented as mean+/−SE (n=3). F. $Ca^{2+}$ uptake (Upper panel) and SERCA activity (Lower panel) were assayed in the presence or absence of rPKAc. Results are presented as nmol ($Ca^{2+}$ or $P_i$)/min/mg (mean+/−SE) (n=3).

FIG. 8 a-d. Detection of PDE3A isoforms by Superose 6 (S6) gel-filtration chromatography of solubilized human myocardial membrane or cytosolic fractions. Solubilized myocardial membranes (A) and cytosolic fractions (B) were prepared (3 mg protein, 1 ml) and subjected to chromatography on S6 columns. Upper Panels: Portions (10 µl) of fractions (0.5 ml) were assayed for PDE3 activity (▲) (pmol cAMP hydrolysed/min/0.5 ml) and protein content [AU (absorption units) 280 nm](●). Molecular mass standard peaks are indicated: 1, thyroglobulin (670 kDa); 2, γ-globulin (158 kDa); 3, ovalbumin (44 kDa); 4, myoglobin (17 kDa); 5, vitamin B12 (1.35 kDa). Bottom panels: Portions (20 µl) of indicated fractions were subjected to SDS/PAGE and immunoblotted with anti-PDE3A antibodies as indicated. One representative experiment is shown (n=3). (C) Pooled HMW and LMW peaks (Lower panels of FIGS. 7A and 7B) were subjected to immunoprecipitation with anti-PDE3A antibody, and immunoblotted with anti-phospho-PKA-substrate (Upper panel) and anti-PDE3A (Lower panel) antibodies. Bar graph (Right panel) summarizing pPDE3A1/PDE3A1 (p3A1/3A1) and pPDE3A2/PDE3A2 (p3A2/3A2) ratios in HMW and LMW peaks; 10-fold increase in phosphorylation of PDE3A1 and ~5 fold increase in phosphorylation of PDE3A2 in HMW peaks compared to LMW peaks (*p<0.01). Results are representative of 3 individual experiments. (D) PDE3A was immunoprecipitated from solubilized myocardial membranes and incubated, as indicated, with or without 250 units of rPKAc in the presence of 200 µM ATP and 5 mM $MgCl_2$ in phosphorylation buffer, supplemented with (Upper panel) or without (Lower panel) [γ-$^{32}$P] ATP, as described in methods. rPKAc plus 10 uM PKI-tide (PKAc inhibitor) was also used as a control. Upper panel: The reaction products were subjected to SDS-PAGE and, after phosphoimager scanning of the wet gels, for detection of $^{32}$P-PDE3A. Middle panel: PDE3A isoforms were identified by Western blotting. Lower panel: PDE3 activity was assayed in PDE3A immunoprecipitates incubated with or without rPKAc and PKI in the absence of [γ-$^{32}$P] ATP. Results are expressed as pmol cAMP hydrolyzed/min. Shown are representative data from 3 independent experiments.

FIG. 9. rPKAc increases interaction of PDE3A with signaling molecules in Superose 6 LMW-fractions of solubilized human myocardial membranes. Solubilized myocardial membranes (3 mg protein, 1 ml) were subjected to chromatography on S6 columns as described in FIG. 7A and fractionated into LMW and HMW fractions. LMW fractions were pooled from two different experiments (FIG. 7A), and concentrated via centriprep YM-3 (centrifugal filter unit with Ultracel-3 membrane, >3 Kd: nominal molecular weight limit). Upper Panels: Pooled and concentrated S6 membrane LMW fractions were split, incubated without or with rPKAc in phosphorylation buffer with 200 µM ATP and 5 mM $MgCl_2$ for 1 h at 30° C., and re-chromatographed on S6-column. Portions (10 µl) of fractions (0.5 ml) were assayed for PDE3 activity (▲) (pmol cAMP hydrolysed/min/0.5 ml) and protein content [AU (absorption units) 280 nm](●). Molecular mass standards: 1. thyroglobulin (670 kDa); 2. γ-globulin (158 kDa); 3. ovalbumin (44 kDa); 4. myoglobin (17 kDa); 5. vitamin B12 (1.35 kDa). Bottom panels: Portions (20 µl) of indicated fractions were subjected to SDS/PAGE and immunoblotted with antibodies as indicated. Representative results from one of two independent experiments are shown.

FIG. 10. rPKAc promotes interactions of PDE3A with components of the SERCA2 regulatory signalosome. Solubilized myocardial membranes were prepared (3 mg protein, 1 ml) and subjected to chromatography on S6 columns as in FIG. 7A. Membrane LMW fractions were pooled from two different experiments (FIG. 7A), and concentrated via centriprep YM-3 (Centriprep centrifugal filter unit with Ultracel-3 membrane). Pooled, concentrated fractions were split and incubated without or with rPKAc in phosphorylation buffer with 200 µM ATP and 5 mM $MgCl_2$ for 1 h at 30° C. The fractions were incubated with anti-PDE3A-CT (10 µg) or non-immune IgG (10 µg) (overnight, 4° C.), and immunoprecipitated using Protein-G sepharose. Protein G-sepharose-bound proteins were eluted by boiling in 200 µl of Laemmli's sample buffer. Samples (15 µl) were subjected to SDS/PAGE and immunoblotted with specific antibodies as shown. Input membrane proteins (10 g) were also loaded on the gels as positive controls. Representative results from three independent experiments are shown. Similar amounts of PDE3A were immunoprecipitated in the control group and in reactions incubated with rPKAc. Band intensities of immunoprecipitated PDE3A and its interacting signaling molecules were analyzed using LAS3000 analyzer and presented as binding percentage ratios of signaling molecules (rPKAc/control). For PDE3A, band intensities of pPDEA1/pPDE3A2/pPDE3A3 in PKAc/control percentage ratios were calculated. *P<0.01 vs control (n=3 independent experiments).

FIG. 11 a-d. rPKAc phosphorylates rhPDE3A and increases its interactions rSERCA2. A. Schemes representing PDE3A1 [NHR1: trans-membrane domain (obligatory membrane insertion domain); NHR2: membrane association domain; CCR: conserved C-terminal catalytic region; P1-4: predicted PKA phosphorylation sites; rhPDE3A and truncated mutants (PDE3A2, PDE3A-A510, PDE3A-RD), and rSERCA2 (1042 amino acids, 3-77 cation transporter N-terminal; 93-341, E1-E2 ATPase; 345-724, haloacid dehydrogenase like hydrolase; 819-991, cation transporter ATPase C-terminus). B. Putative PKA phosphorylation sites of PDE3A designated with asterisks. C-D. Purified rSERCA2 (150 ng) (Abnova) and 50 units of Flag-tagged rhPDE3A1 truncated mutants [rhPDE3A2, rhPDE3A-A510, and similarly expressed rhPDE3A-RD (aa 146-484)](FIG. 11D) or mutants lacking the PKA putative phosphorylation site mutants of rhPDE3A1 [Ser292/293A (M1), S312A (M2), S428A (M3), S438A (M4), S292A/293A/312A/438A (M5)] (FIG. 11C) were incubated with or without 50 units of rPKAc at 30° C. for 30 min and 5 mM $MgCl_2$ in phosphorylation buffer. Proteins were immunoprecipitated with anti-Flag antibodies and immunoblotted with anti-SERCA2 (upper panel), or anti-Flag (middle panel). Lower panel: input control (SERCA2). Shown are representative blots from three independent experiments. (RD: regulatory domain; AA: amino acid).

FIG. 12 a-c. rPKAc induced phosphorylation of rhPDE3A induces interaction with rat rAKAP18δ. (A). Schemes representing PDE3A1 [NHR1: trans-membrane domain (obligatory membrane insertion domain); NHR2: membrane association domain; CCR: conserved C-terminal catalytic region]; rAKAP18δ with RII binding site from amino acid (aa) 301-314 and a unique N-terminus from aa 1-26. B-C. His tagged rAKAP18δ (100 ng) and 50 units of Flag-tagged rhPDE3A1 were incubated with different concentrations of rPKAc (B), or without or with 50 units of rPKAc and 200 µM ATP at 30° C. in phosphorylation buffer (C). Immunoprecipitated proteins and input were immunoblotted with anti-Flag and anti-AKAP18-his antibodies as indicated. Similar amounts of AKAP18δ were immunoprecipitated in the control groups and in reactions incubated with rPKAc. (C) Bar graph summarizing binding of PDE3A with AKAP18δ in the absence (control) and presence of rPKAc. Ratios of rhPDE3A bound to rAKAP18δ were calculated without (Control, C) or with rPKAc; ~9-fold increase in binding of rhPDE3A with AKAP18δ in the presence of rPKAc (*p<0.001). Shown are representative blots from three independent experiments.

FIG. 13 a-c. Model of the regulation of SERCA2 activity by cAMP and the AKAP18 and PLB-containing signalosome. A. Components of the AKAP18/SERCA2/PLB complex are shown. B. In the absence of cAMP, SERCA2 is inhibited by its interaction with PLB. Activation of PKA by cAMP results in the phosphorylation of PLB and PDE3A. The former dissociates from SERCA2, increasing SERCA2's activity, but the integration of phosphorylated PDE3A into the complex limits this effect by increasing hydrolysis of cAMP. PP1 and PP2A in the complex would be expected to catalyze the dephosphorylation of PDE3A, PLB and other PKA substrates, and return the SERCA2 complex to its basal state. C. PDE3 inhibition potentiates the effect of cAMP on SERCA2.

DETAILED DESCRIPTION OF THE INVENTION

In its various aspects, the present invention provides peptides, polypeptides, protein, and/or peptidomimetics that are specific or selective inhibitors of wild-type or endogenous PDE3A1, antibodies that specifically recognize and bind them, nucleic acid molecules that encode them, recombinant DNA molecules, transformed host cells, generation methods, assays, methods, and compositions.

Compositions of the Invention

Conventional PDE3 inhibitors increase cardiac contractility, but adversely affect survival, through mechanisms that remain uncertain. Our invention involves e.g., selectively targeting PDE3 isoforms through mechanisms other than catalytic site inhibition that are likely to involve interfering with the protein-protein interactions of these isoforms so as to avoid the adverse consequences of conventional PDE3 inhibitors and to provide additional beneficial actions such as blocking pathologic hypertrophic responses.

In an embodiment of the invention, we generated catalytically-inactive forms of PDE3A1 and PDE3A2 as 'dominant negatives' to affect hypertrophic responses to beta-adrenergic receptor stimulation in neonatal rat ventricular myocytes. Like catalytic-site inhibition with cilostamide, expression of the PDE3A2 dominant negative promotes hypertrophy in these cells, and has no opposing effect on hypertrophic responses to norepinephrine. In contrast, expression of the PDE3A1 dominant negative has no pro-hypertrophic effect, and actually blocks the hypertrophic responses to norepinephrine. This latter finding indicates that selectively targeting PDE3 isoforms through mechanisms other than catalytic-site inhibition (these other mechanisms are likely to involve interfering with the protein-protein interactions of these isoforms) can avoid the adverse consequences of conventional PDE3 inhibitors, and can have additional beneficial actions such as blocking pathologic hypertrophic responses.

The invention provides for an isolated or purified peptide, polypeptide or peptidomimetic possessing anti-hypertrophic activity in a cardiac myocyte by specifically or selectively inhibiting wild-type or endogenous PDE3A1. In one embodiment, the polypeptide may be a mutant derived from wild-type PDE3A1 protein. The wild-type PDE3A1 protein may have the amino acid sequence given in SEQ ID NO:1. In one embodiment, the wild-type PDE3A1 protein has the amino acid sequence given in SEQ ID NO:1 at about amino acid position 146 to 1141.

As used herein, the term "isolated" or "purified" in reference to a peptide, polypeptide or peptidomimetic of the invention does not require absolute purity and is substantially free of impurities, e.g., interfering materials that inhibit the function of a peptide, polypeptide or peptidomimetic of the invention.

In one embodiment, the composition comprises isolated polypeptide or an equivalent, derivative or analog thereof having 7 or more amino acid sequences of PDE3A1, wherein the composition is substantially free of polypeptide or an equivalent, derivative or analog thereof of non-PDE3A1.

In one embodiment, the composition comprises isolated polypeptide or an equivalent, derivative or analog thereof having 10 or more amino acid sequences of PDE3A1, wherein the composition is substantially free of polypeptide or an equivalent, derivative or analog thereof of non-PDE3A1.

In one embodiment, the composition comprises isolated polypeptide or an equivalent, derivative or analog thereof having 20 or more amino acid sequences of PDE3A1, wherein the composition is substantially free of polypeptide or an equivalent, derivative or analog thereof of non-PDE3A1.

In one embodiment, the mutant derived from wild-type PDE3A1 protein may be a catalytically compromised mutant of PDE3A1 protein. In another embodiment, the catalytically compromised mutant of PDE3A1 protein may be a catalytically inactive mutant of PDE3A1 protein or a catalytically reduced mutant of PDE3A1 protein which may be a result of a mutation affecting tyrosine-751 (Y751), histidine-836 (H836), histidine-840 (H840), glutamic acid-866 (E866), aspartic acid-950 (D950), or phenylalanine-1004 (F1004). In a preferred embodiment, the catalytically inactive mutant of PDE3A1 protein has a mutation at phenylalanine-1004 (F1004).

In one embodiment, the mutation may be an amino acid change to an alanine. In another embodiment, the mutation may be an amino acid change to any amino acid other than an alanine. The amino acid change may be glycine, serine, threonine, cysteine, valine, leucine, isoleucine, methionine, proline, tyrosine, tryptophan, phenylalanine, aspartic acid, glutamic acid, asparagine, glutamine, histidine, lysine or arginine, and not an amino acid present in the wild-type PDE3A1 at a position to be mutated.

In a preferred embodiment, the catalytically inactive mutant of PDE3A1 protein has a mutation at phenylalanine-1004 to an alanine (F1004A) with the amino acid sequence given in SEQ ID NO:2. In one embodiment, the catalytically inactive mutant of PDE3A1 protein has the amino-acid sequence given in SEQ ID NO:2 at about amino acid position 146 to 1141.

In another embodiment, the mutant derived from wild-type PDE3A1 protein may be a deletion mutant of PDE3A1 protein. In another embodiment, the deletion mutant of PDE3A1 protein lacks an intact C-terminal catalytic region. In a further embodiment, the deletion mutant of PDE3A1 protein may comprise an amino-terminal sequence without the C-terminal catalytic region.

In a further embodiment, the polypeptides of the invention may further comprising a mutation or multiple mutations in which amino acid corresponding to serine-292, serine-293 and/or serine-294 as provided in SEQ ID NO:1 are substituted with aspartic acid, glutamic acid or combination of aspartic acid and glutamic acid. In yet a further embodiment of the polypeptides of the invention, the mutation of serine-292, serine-293 and/or serine-294 permits association with SERCA2 protein.

In yet another embodiment, the C-terminal catalytic region may be given in SEQ ID NO: 1 at about amino acid position 669 to 1108. In another embodiment, the amino-terminal sequence may comprise ten or more amino acids having a sequence identical or homologous to a sequence at about amino acid position 146 to 668 in SEQ ID NO:1. In another embodiment, the amino-terminal sequence may comprise ten or more amino acids having a sequence identical or homologous to a sequence in the N-terminal amino-acid sequence present in PDE3A1 but not in PDE3A3, corresponding to about amino acid position 146 to 483 in SEQ ID NO:1. In yet another embodiment, the amino-terminal sequence may comprise ten or more amino acids having a sequence identical or homologous to a sequence in the N-terminal amino-acid sequence present in PDE3A1 but not in PDE3A2, corresponding to about amino acid position 146 to 299 in SEQ ID NO:1. In one embodiment, the source of PDE3A homologs is mammalian organisms.

In an embodiment, the polypeptide comprises a sequence of amino acids present in both PDE3A1 and PDE3A2 isoforms but having a different conformation in the two isoforms. In one embodiment, the different conformation is a difference in the secondary structure for a sequence of amino acid present in both PDE3A1 and PDE3A2 isoforms. In another embodiment, the different conformation is a difference in the tertiary structure for a sequence of amino acid present in both PDE3A1 and PDE3A2 isoforms.

In another embodiment, the polypeptide may comprise a sequence of amino acids present in both PDE3A1 and PDE3A2 isoforms but having differential accessibility for protein-protein interaction in the two isoforms. The sequence of amino acids present in both PDE3A1 and PDE3A2 isoforms may have greater accessibility for protein-protein interactions in the PDE3A1 isoform than in the PDE3A2 isoform.

In yet another embodiment, the polypeptide may comprise a sequence of amino acids comprising a serine amino acid which is differentially phosphorylated between PDE3A1 and PDE3A2 isoforms. Phosphorylation of the serine amino acid in PDE3A1 isoform may influence protein-protein interactions. In one embodiment, the serine amino acid that is unique to PDE3A1 which may be phosphorylated is serine-292, serine-293 and/or serine-294. The phosphorylation of the serine amino acid in PDE3A1 isoform may influence protein-protein interaction such as the association of PDE3A1 protein with SERCA2 protein.

Human homologues of PDE3A, naturally occurring allelic variants of PDE3A and genomic PDE3A sequences may share a high degree of homology to the mouse PDE3A sequences herein described. In general, such nucleic acid molecules will hybridize to the human PDE3A sequence under stringent conditions. Such sequences will typically contain at least 70% homology, preferably at least 80%, most preferably at least 90% homology to the mouse PDE3A sequence.

In an embodiment, PDE3A1 and PDE3A2 isoforms may have a common amino-acid sequence corresponding to about amino acid position 300 to 1141 in SEQ ID NO:1.

In another embodiment, the serine amino acid may be any serine in the polypeptide corresponding to about amino acid position 300 to 1141 in SEQ ID NO:1.

In an embodiment, the mutant variant derived from wild-type PDE3A1 protein may be a fusion or chimeric protein with a compromised, reduced or inactive catalytic activity. The compromised, reduced or inactive catalytic activity may be a phosphodiesterase activity. The phosphodiesterase activity is hydrolysis of cAMP and/or cGMP to 5'-AMP and/or 5'GMP, respectively.

The invention also provides a peptidomimetic possessing an anti-hypertrophic activity in a cardiac myocyte. The peptidomimetic mimics a structure or part of a structure formed by a polypeptide derived from the amino terminus of wild-type PDE3A1 at about amino-acid position 146 to 668 in SEQ ID NO: 1. In one embodiment, the peptidomimetic mimics a structure or part of a structure formed by an amino-terminal polypeptide present in wild-type PDE3A1 but not in PDE3A3, corresponding to about amino acid position 146 to 483 in SEQ ID NO: 1. In another embodiment, the peptidomimetic mimics a structure or part of a structure formed by an amino-terminal polypeptide present in wild-type PDE3A1 but not in PDE3A2, corresponding to about amino acid position 146 to 299 in SEQ ID NO: 1. Alternatively, the peptidomimetic mimics a structure or part of a structure formed by wild-type PDE3A1 from e.g., about amino acid position 300 to 1141 in SEQ ID NO: 1, in which the structure or part of the structure is different in PDE3A2. The structure or part of the structure of interest is one in which an amino acid sequence present in both wild-type PDE3A1 and PDE3A2 isoforms forms different structures depending on whether the amino acid sequence is present within the context of a PDE3A1 isoform or a PDE3A2 isoform; the peptidomimetic will mimic the structure in PDE3A1 isoform associated with this stretch of amino acid sequence. In one embodiment, the structure of part of the structure is a secondary structure. In a related embodiment, the structure of part of the structure is a tertiary structure. Alternatively, the peptidomimetic mimics a structure or part of a structure having greater accessibility for protein-protein interaction in wild-type PDE3A1 than in PDE3A2, corresponding to about amino-acid position 300 to 1141 in SEQ ID NO:1. Alternatively, the peptidomimetic mimics a structure or part of a structure of phospho-PDE3A1 at a serine residue unique to PDE3A1 protein or phosphorylated selectively or differentially in wild-type PDE3A1 and PDE3A2 proteins.

The invention also provides a polypeptide having the ability to avoid pro-hypertrophic effect of conventional PDE3 inhibition in a cardiac myocyte. In one embodiment, the polypeptide may be a mutant variant derived from wild-type PDE3A1 protein. The wild-type PDE3A1 protein has the amino acid sequence given in SEQ ID NO:1 at about amino acid position 146 to 1141.

Inhibition of PDE3 activity can refer to either inhibition of catalytic activity or protein-protein interactions, including protein-protein interactions that lead to post-translational modification, such as phosphorylation. Conventional PDE3 inhibitors target the phosphodiesterase activity of the catalytic domain of two or more PDE3 family members (PDE3A1, PDE3A2, PDE3A3 and PDE31B). As such, conventional PDE3 inhibition does not result in the inhibition of a single PDE3 isoform but rather affects more than one isoforms if not all PDE3 family members. Conventional PDE3 inhibition is associated with cardiac myocyte hypertrophy. In contrast to conventional PDE inhibitors, isoform-specific or isoform-selective inhibitor of the invention targets specific PDE3 isoform (such as PDE3A1 isoform) to inhibit protein-protein interaction of the native PDE3 isoform targeted and as shown in subject's invention produce beneficial effect, such as anti-hypertrophy in cardiac myocyte.

In one embodiment, the polypeptide of the invention is isolated or purified polypeptide.

In one embodiment, the mutant variant derived from wild-type PDE3A1 protein may be a catalytically compromised mutant of PDE3A1 protein. The catalytically compromised mutant of PDE3A1 protein may be a catalytically inactive mutant of PDE3A1 protein or a catalytically reduced mutant of PDE3A1 protein. In another embodiment, the catalytically compromised, reduced or inactive mutant of PDE3A1 protein may be a result of a mutation affecting tyrosine-751 (Y751), histidine-836 (H836), histidine-840 (H840), glutamic acid-866 (E866), aspartic acid-950 (D950) or phenylalanine-1004 (F1004). In a preferred embodiment, the catalytically inactive mutant of PDE3A1 protein may be a mutation at phenylalanine-1004 (F1004).

In one embodiment, the mutant variant derived from wild-type PDE3A1 protein or mutant PDE3A1 protein of the invention is an isolated or purified protein.

The invention further provides nucleic acid molecules encoding a polypeptide possessing anti-hypertrophic activity in a cardiac myocyte. In one embodiment, the nucleic acid molecule is DNA (e.g., cDNA) or a hybrid thereof. Alternatively, the nucleic acid molecule is RNA or a hybrid thereof.

Additionally, the invention provides a vector, which comprises the nucleotide sequences of the invention. A host vector system is also provided. The host vector system comprises the vector of the invention transfected or introduced in a suitable host cell. Examples of suitable host cells include, but are not limited to, prokaryotic and eukaryotic cells.

The invention also provides a peptidomimetic to avoid or counter pro-hypertrophic effects of conventional PDE3 inhibition (i.e., inhibition of the catalytic activity of PDE3) in a cardiac myocyte. The peptidomimetic mimics a structure or part of a structure formed by a polypeptide derived from the amino terminus of wild-type PDE3A1 at about amino acid position 146 to 668 in SEQ ID NO:1. In one embodiment, the peptidomimetic mimics a structure or part of a structure formed by an amino-terminal polypeptide present in wild-type PDE3A1 but not in PDE3A3, corresponding to about amino acid position 146 to 483 in SEQ ID NO:1. In another embodiment, the peptidomimetic mimics a structure or part of a structure formed by an amino-terminal polypeptide present in wild-type PDE3A1 but not in PDE3A2, corresponding to about amino acid position 146 to 299 in SEQ ID NO: 1. Alternatively, the peptidomimetic mimics a structure or part of a structure formed by wild-type PDE3A1 from about amino acid position 300 to 1141 in SEQ ID NO:1, in which the structure or part of the structure is different in PDE3A2. The structure or part of the structure of interest is one in which an amino acid sequence present in both wild-type PDE3A1 and PDE3A2 isoforms forms different structures depending on whether the amino acid sequence is present within the context of a PDE3A1 isoform or a PDE3A2 isoform; the peptidomimetic will mimic the structure in PDE3A1 isoform associated with this stretch of amino acid sequence.

Alternatively, the peptidomimetic mimics a structure or part of a structure having greater accessibility for protein-protein interactions in wild-type PDE3A1 than in PDE3A2, corresponding to about amino acid position 300 to 1141 in SEQ ID NO:1. Alternatively, the peptidomimetic mimics a structure or part of a structure of phospho-PDE3A1 at a serine residue unique to PDE3A1 protein or differentially phosphorylated between wild-type PDE3A1 and PDE3A2 proteins.

In one embodiment, the peptidomimetic of the invention is isolated or purified peptidomimetic.

Nucleic Acid Molecules that Encode Peptides and/or Polypeptides that Specifically or Selectively Inhibit Pde3A1

Another aspect of the invention provides nucleic acid molecules encoding the peptides or polypeptides that specifically or selectively inhibit PDE3A1 of the invention, preferably in isolated form, including DNA, RNA, DNA/RNA hybrid, and related molecules, nucleic acid molecules complementary to the PDE3A1 coding sequence or a part thereof, and those which hybridize to the nucleic acids encoding peptides and/or polypeptides that specifically or selectively inhibit PDE3A1. Specifically contemplated are genomic DNA, cDNAs, ribozymes, and antisense molecules, as well as nucleic acids based on an alternative backbone or including alternative bases, whether derived from natural sources or synthesized.

For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the herein described PDE3A1 amino acid sequences.

Embodiments of the nucleic acid molecules of the invention include primers, which allow the specific amplification of nucleic acid molecules of the invention or of any specific parts thereof, and probes that selectively or specifically hybridize to nucleic acid molecules of the invention or to any part thereof. The nucleic acid probes can be labeled with a detectable marker. Examples of a detectable marker include, but are not limited to, a radioisotope, a fluorescent compound metal chelator or an enzyme. Technologies for generating DNA and RNA probes are well known.

As used herein, a nucleic acid molecule is said to be "isolated" when the nucleic acid molecule is substantially separated from contaminant nucleic acid molecules that encode polypeptides other than those that encode peptides or polypeptides that specifically or selectively inhibit PDE3A1.

The peptide, polypeptide or peptidomimetic of the invention may be formulated in a pharmaceutical composition further comprising a pharmaceutically acceptable carrier.

The phrase "pharmaceutically acceptable carrier" refers to any carrier known to those skilled in the art to be suitable for the particular mode of administration. In addition, the peptide, polypeptide or peptidomimetic of the invention may be formulated as the sole pharmaceutically active ingredient in the composition or may be combined with other active ingredients.

Compositions herein comprise one or more peptide, polypeptide or peptidomimetic of the invention. The peptide, polypeptide or peptidomimetic are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the peptide, polypeptide or peptidomimetic described above are formulated into pharmaceutical compositions using techniques and procedures well known in the art (see, e.g., Ansel Introduction to Pharmaceutical Dosage Forms, Fourth Edition 1985, 126).

In one embodiment, the compositions may be formulated for single dosage administration. To formulate a composition, the peptide, polypeptide or peptidomimetic is dissolved, suspended, dispersed or otherwise mixed in a selected carrier at an effective concentration in an amount such that the treated condition may be relieved, prevented, or one or more symptoms are ameliorated.

The active compound (e.g., peptide, polypeptide or peptidomimetic of the invention) is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems known in the art, and then extrapolated therefrom for dosages for subjects such as humans.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions may be provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.005%-100% (wt %) active ingredient, in one embodiment 0.1-95% (wt %), in another embodiment 75-85% (wt %).

Combination Therapy

In another embodiment, the compositions may be administered in combination, or sequentially, with another therapeutic agent. Such other therapeutic agents include those known for treatment, prevention, or amelioration of one or more symptoms of diseases and disorders described herein.

Methods of the Invention

The invention also provides methods for preventing, inhibiting or reversing hypertrophy in a cardiac myocyte. The method comprises contacting the cell with a peptide, polypeptide or peptidomimetic of the invention, in an amount effective so as to prevent, inhibit or reverse myocardial hypertrophy.

The invention further provides methods for avoiding pro-hypertrophic effect of conventional PDE3 inhibition in a cardiac myocyte. The method comprises contacting the cell with a peptide, polypeptide or peptidomimetic of the invention, in an amount to avoid pro-hypertrophic effect of conventional PDE3 inhibition in a cardiac myocyte.

The invention also provides methods for preventing, inhibiting or reversing myocardial hypertrophy in a subject. The method comprises administering to the subject a peptide, peptidomimetic or small molecule that interacts with a PDE3-interacting protein that affects myocardial hypertrophy in an amount effective so as to prevent, inhibit or reverse myocardial hypertrophy.

In one embodiment, the invention provides methods for preventing, inhibiting or reversing myocardial hypertrophy. The method comprises administering the vector of the invention in a cardiac myocyte, said vector being genetically modified by insertion of at least one therapeutic gene into said vector to produce functional molecules in a sufficient amount to prevent, inhibit or reverse myocardial hypertrophy in the cell.

In one embodiment, the invention provides methods for avoiding pro-hypertrophic effect of conventional PDE3 inhibition in a subject. The method comprises administering to the subject a peptide, polypeptide or peptidomimetic of the invention, in an amount to avoid pro-hypertrophic effect of conventional PDE3 inhibition in the subject.

In another embodiment, the invention provides methods for avoiding pro-hypertrophic effect of conventional PDE3 inhibition in a cardiac myocyte. The method comprises administering the vector of the invention into the cell, said vector being genetically modified by insertion of at least one therapeutic gene into said vector to produce functional molecules in a sufficient amount to avoid pro-hypertrophic effect of conventional PDE3 inhibition in a cardiac myocyte.

In one embodiment, the invention provides methods for preventing, inhibiting or treating a cardiac disease such as heart failure, advanced heart failure, NYHA class 3 or 4 symptoms, hypertension, coronary artery disease, cardiomyopathy, pulmonary hypertension, cardiac hypertrophy, hypotension, shock, valvular heart disease, rheumatic heart disease, congenital heart disease, myocarditis, pericardial disease or arrhythmia. The method comprises administering to the subject a peptide, peptidomimetic or small molecule that interacts with a PDE3-interacting protein that affects cardiac disease in an amount effective so as to prevent, inhibit or reverse cardiac disease.

The invention also provides methods for obtaining beneficial effect of PDE3 inhibition in a subject with reduced or no adverse effect. The subject may be treated with a PDE3 isoform-specific or isoform-selective inhibitor.

Examples of beneficial effect may be increased cardiac output, augmented myocardial contractility, lower left ventricular filling pressure, inhibition or reversal of hypertrophic response of cardiac myocytes to norepinephrine or other G protein-coupled receptor agonists, increased intracellular $Ca^{2+}$ cycling in cardiac myocytes, increased $Ca^{2+}$ uptake from cytosol to sarcoplasmic reticulum during diastole and increased $Ca^{2+}$ release from sarcoplasmic reticulum during systole, decreased pro-apoptotic signaling, increased intracellular cAMP level in a cellular compartment associated with increased cardiac output and/or anti-hypertrophic response, or alteration in phosphorylation of proteins leading to increased cardiac output and/or anti-hypertrophic response.

Examples of adverse effect may be sudden cardiac death, increased pro-apoptotic signaling, cardiac myocyte hypertrophy and cardiac hypertrophy.

In one embodiment, the PDE3 isoform-specific or isoform-selective inhibitor may be a PDE3A1-specific or PDE3A1-selective inhibitor. In another embodiment, the PDE3A1-specific or PDE3A1-selective inhibitor may be a catalytically compromised, reduced or inactive PDE3A1 or its derivative.

In one embodiment, the subject may be a subject with a cardiac disease such as heart failure, advanced heart failure, NYHA class 3 or 4 symptoms, hypertension, coronary artery disease, cardiomyopathy, pulmonary hypertension, cardiac hypertrophy, hypotension, shock, valvular heart disease, rheumatic heart disease, congenital heart disease, myocarditis, pericardial disease or arrhythmia.

The invention further provides methods for increasing selectivity of PDE3 inhibition in a cardiac myocyte. The method comprises contacting the cardiac myocyte with a peptide, peptidomimetic or small molecule that interacts with a PDE3-interacting protein at an interaction site selective for a PDE3 isoform. Alternatively, the method may comprise contacting, expressing in or introducing in the cardiac myocyte a catalytically compromised, reduced or inactive form of a PDE3 isoform or its derivative, so as to selectively inhibit the PDE3 isoform.

The invention also provides methods for selectively inhibiting a PDE3 isoform. The method comprises introduction or expression of an altered or mutated version of the PDE3 isoform to be selectively inhibited in a cell. In one embodiment, the altered or mutated version of the PDE3 isoform has altered protein-protein interaction or has altered or mutated catalytic activity. In another embodiment, the altered or mutated catalytic activity may arise due to reduced binding affinity for its substrate (cAMP (or 3',5'-cAMP or 3',5'-cyclic adenosine monophosphate) and/or cGMP (or 3'5'-cGMP or 3',5'-cyclic guanosine monophosphate)), reduced hydrolysis of its substrate, and/or increased affinity for its products (5'-AMP (or 5'-adenosine monophosphate) and/or 5'-GMP (or 5'-guanosine monophosphate)).

Additionally, the invention provides methods for selectively altering cAMP level within a cellular compartment. The method comprises introduction or expression of an altered or mutated version of a PDE3 isoform associated with the cellular compartment. The altered or mutated version of the PDE3 isoform has altered protein-protein interaction or has altered or mutated catalytic activity.

In one embodiment, the PDE3 isoform may be PDE3A1, PDE3A2, PDE3A3 or PDE3B.

In accordance with the practice of this invention, a subject may be a mammal such as a human, equine, porcine, bovine, murine, canine, feline, or primate subject. Other mammals are also included in this invention.

The invention also provides methods for eliciting positive inotropic response in a subject without myocardial hypertrophy or for eliciting positive inotropic and myocardial anti-hypertrophic responses in a subject. The method comprises administering to the subject an agent or any of the agents. The agent may be an agent that selectively decreases PDE3A1 activity in a cardiac myocyte; a peptide, a peptidomimetic or small molecule that mimics PDE3A1 amino terminus; a peptide, peptidomimetic or small molecule that interacts with a PDE3A1-interacting protein that selectively affects cAMP level in the intracellular compartment associated with PDE3A1 so as to increase $Ca^{2+}$ uptake from cytosol to sarcoplasmic reticulum during diastole and increase $Ca^{2+}$ release from sarcoplasmic reticulum during systole; a gene therapy vector for the delivery and/or expression of a catalytically compromised, reduced or inactive PDE3A1 mutant gene so as to selectively increase cAMP locally in an intracellular compartment associated with endogenous PDE3A1 protein.

The modes of administration encompassed by the methods of the invention include but are not limited to gene therapy, intravenous, intramuscular, intraperitoneal, oral, inhalation and subcutaneous methods, as well as implantable pump, continuous infusion, liposomes, suppositories, topical contact, vesicles, capsules, biodegradable polymers, hydrogels, controlled release patch and injection.

Isoform-specific inactivation of PDE3A1 activity may be achieved by targeting the nucleic acid sequence present in PDE3A1 mRNA but absent in PDE3A2 and PDE3A3 mRNAs. Such sequences can be used to prepare anti-sense or RNAi molecules to downregulate PDE3A1 expression without affecting the expression of PDE3A2 or PDE3A3. Alternatively, the 5' region of the PDE3A gene unique to PDE3A1 may be "knocked out" using procedures known to those skilled in the art of transgenic animal preparation, so as to preferentially decrease PDE3A1 activity without affecting or significantly affecting the activity of the other PDE3A isoforms. Transgenic animals or cell lines with knocked out PDE3A1 gene (without knocking out PDE3A2 or PDE3A3 expression), anti-sense PDE3A1 gene, or siRNA targeting PDE3A1 isoform transgene may be prepared.

Transgenic non-human mammals or genetically modified mammalian cells may be prepared that express sequences derived from the amino-terminal sequence of PDE3A1 protein either as a truncated protein or as a fusion protein using standing recombinant DNA methods and molecular biology techniques. Expression of sequences from the amino-terminal half of PDE3A1 protein in cardiac cells should protect these cells from hypertrophic inducing agents, such as norepinephrine and non-isoform-selective PDE3A inhibitors.

Once generated, the PDE3A1 homologue-deficient animal or cell line or PDE3A1 amino-terminal polypeptide expressing animal or cell line can be used to (1) identify biological and pathological processes mediated by the PDE3A1 protein, (2) identify proteins and other genes that interact with the PDE3A1 proteins, (3) identify agents that can be exogenously supplied to overcome a PDE3A1 protein deficiency, (4) serve as an appropriate screen for identifying mutations within the PDE3A1 gene that increase or decrease activity, (5) serve as a screen for agents that modulate cardiac hypertrophy.

The invention further provides methods for identifying an agent of interest that mimics a site of interaction of PDE3A1 protein with SERCA2 protein. In one embodiment, the method comprises (a) contacting the agent with a PDE3A1-SERCA2 complex, wherein the PDE3A1 protein of the complex comprises phosphorylated-serine-292, phosphorylated-serine-293 and/or phosphorylated serine-294, or alternatively, singly, doubly or triply mutated serine-292, serine-293 and/or serine-294 to aspartic acid or to glutamic acid; (b) determining whether the agent competes with PDE3A1 of the PDE3A1-SERCA2 complex of (a) for SERCA2 protein wherein the agent that forms an agent-SERCA2 complex displacing PDE3A1 from PDE3A1-SERCA2 complex of (a) is the agent of interest that mimics a site of interaction of PDE3A1 protein with SERCA2 protein thereby identifying the agent of interest that mimics a site of interaction of PDE3A1 protein with SERCA2 protein.

The invention additionally provides methods for identifying an agent of interest that mimics a site of interaction of SERCA2 protein with PDE3A1 protein. In an embodiment of the invention, the method comprises (a) contacting the agent with a PDE3A1-SERCA2 complex, wherein the PDE3A1 protein of the complex comprises phosphorylated-serine-292, phosphorylated-serine-293 and/or phosphorylated serine-294, or alternatively, singly, doubly or triply mutated serine-292, serine-293 and/or serine-294 to aspartic acid or to glutamic acid; (b) determining whether the agent competes with SERCA2 of the PDE3A1-SERCA2 complex of (a) for PDE3A1 protein wherein the agent that forms an agent-PDE3A1 complex displacing SERCA2 from the PDE3A1-SERCA2 complex of (a) is the agent of interest that mimics a site of interaction of SERCA2 protein with PDE3A1 protein thereby identifying the agent of interest that mimics the site of interaction of SERCA2 protein with PDE3A1 protein.

In accordance with the practice of the invention, the agent of interest, SERCA2 protein or PDE3A protein may be labeled with a detectable marker. Examples of suitable detectable markers include, but are not limited to, a radioactive label, a colorimetric marker, a fluorophore, an antigen, an epitope or a product of an enzymatic reaction.

Methods for identifying an agent of interest that disrupts the interaction of PDE3A1 protein with SERCA2 protein are also provided. In one embodiment, the method comprises (a) contacting a labeled PDE3A1 protein or fragment thereof comprising singly, doubly or triply phosphorylated serine-292, serine-293 and/or serine-294, or alternatively, singly or doubly or triply mutated serine-292, serine-293 and/or serine-294 to aspartic acid or to glutamic acid with SERCA2 protein, so as to permit formation of a PDE3A1-SERCA2 complex; (b) contacting the PDE3A1-SERCA2 complex of (a) with one or more agents of interest that may compete with the interaction of PDE3A1 or fragment thereof and SERCA2 protein; (c) detecting the labeled PDE3A1 protein in the PDE3A1-SERCA2 complex of (b) or the labeled PDE3A1 protein released from the PDE3A1-SERCA2 complex of (b); (d) determining the amount (i) of labeled PDE3A1 protein or fragment thereof remaining or released from the PDE3A1-SERCA2 complex of (c) and comparing that amount (i) with an amount (ii) from an agent that does not compete with PDE3A1-SERCA2 complex formation, the amount (i) being less label bound to the SERCA2 protein or more label free from the SERCA2 protein being indicative that the agent of interest competes with the complex formation of PDE3A1 protein and SERCA2 protein thereby identifying the agent of interest that disrupts the interaction of PDE3A1 protein with SERCA2 protein and/or SERCA2 complex.

Additionally, methods for identifying an agent of interest that inhibits the interaction of a PDE3A1 protein with a SERCA2 protein are provided. In one embodiment, the method comprises (a) contacting one or more agents of interest with the SERCA2 protein so as to obtain an agent of interest-SERCA2 complex; (b) contacting the complex of (a) with a labeled PDE3A1 protein or fragment thereof comprising singly or doubly phosphorylated serine-292, serine-293, or alternatively, singly or doubly mutated serine-292, serine-293 to aspartic acid so as to form a PDE3A1-SERCA2 complex; (c) detecting the label of PDE3A1 protein or fragment thereof so complexed with the SERCA2 protein of (b) or free from the SERCA2 protein of (b); and (d) quantitatively determining the amount (i) of labeled PDE3A1 protein or fragment thereof remaining or released from the PDE3A1-SERCA2 complex of (c), and comparing that amount (i) with an amount (ii) from an agent that does not compete with PDE3A1-SERCA2 complex formation, the amount (i) being less label bound to the SERCA2 protein or more label free from the SERCA2 protein being indicative that the agent of interest competes with the complex formation of PDE3A1 protein and SERCA2 protein thereby identifying the agent of interest that inhibits the interaction of a PDE3A1 protein with a SERCA2 protein.

In another embodiment, the method comprises (a) contacting one or more agents of interest with a labeled SERCA2 protein so as to obtain an agent of interest-SERCA2 complex; (b) contacting the complex of (a) with a PDE3A1 protein or fragment thereof comprising singly, doubly or triply phosphorylated serine-292, serine-293 and/or serine-294, or alternatively, singly, doubly or triply mutated serine-292, serine-293 and/or serine-294 to aspartic acid or to glutamic acid; (c) detecting the label of SERCA2 protein bound to the PDE3A1 protein or fragment thereof of (b) or free from the PDE3A1 protein or fragment thereof of (b); and (d) quantitatively determining the amount (i) of labeled SERCA2 protein bound or free from the PDE3A1 protein or fragment thereof of (c), and comparing that amount (i) with an amount (ii) from an agent that does not compete with PDE3A1-SERCA2 complex formation, the amount (i) being less label bound to the SERCA2 protein or more label free from the SERCA2 protein being indicative that the agent of interest competes with the complex formation of PDE3A1 protein and SERCA2 protein thereby identifying the agent of interest that inhibits the interaction of PDE3A1 protein with SERCA2 protein.

In yet another embodiment, the method comprises (a) contacting one or more agents of interest with PDE3A1 protein or fragment thereof so as to obtain an agent of interest-PDE3A1 or fragment thereof complex, wherein PDE3A1 or fragment thereof comprises a singly, doubly or triply phosphorylated serine-292, serine-293 and/or serine-294, or alternatively, singly, doubly or triply mutated serine-292, serine-293 and/or serine-294 to aspartic acid or to glutamic acid; (b) contacting the complex of (a) with a labeled SERCA2 protein; (c) detecting the label of the SERCA2 protein bound to the pde3a1 protein or fragment thereof or free from the PDE3A1 protein or fragment thereof; and (d) quantitatively determining the amount (i) of labeled SERCA2 protein bound or free from the PDE3A1 protein or fragment thereof, and comparing that amount (i) with an amount (ii) from an agent that does not compete with PDE3A1-SERCA2 complex formation, the amount (i) being less label bound to the SERCA2 protein or more label free from the SERCA2 protein being indicative that the agent of interest competes with the complex formation of PDE3A1 protein and SERCA2 protein thereby identifying the agent of interest that inhibits the interaction of PDE3A1 protein with SERCA2 protein.

Further provided are methods for identifying an agent of interest that competes with the interaction of a PDE3A1 protein and a SERCA2 protein. In one embodiment, the method comprises: (a) contacting (i) an agent of interest, (ii) SERCA2 protein, and (iii) a labeled PDE3A1 protein or fragment thereof comprising singly or doubly phosphorylated serine-292, serine-293 and/or serine-294, or alternatively, singly or doubly mutated serine-292, serine-293 and/or serine-294 to aspartic acid or to glutamic acid; (b) detecting the label of PDE3A1 protein or fragment thereof so complexed with the SERCA2 protein or free from the SERCA2 protein; and (c) quantitatively determining the amount (i) of labeled PDE3A1 protein or fragment thereof bound or free from the SERCA2 protein, and comparing that amount (i) with an amount (ii) from an agent that does not compete with PDE3A1-SERCA2 complex formation, the amount (i) being less label bound to the SERCA2 protein or more label free from the SERCA2 protein being indicative that the agent of interest competes with the complex formation of PDE3A1 protein and SERCA2 protein thereby identifying the agent of interest that competes with the interaction of PDE3A1 protein and SERCA2 protein and/or SERCA2 complex.

In another embodiment, the method comprises (a) contacting (i) an agent of interest, (ii) a labeled SERCA2, and (iii) a PDE3A1 protein or fragment thereof comprising singly, doubly or triply phosphorylated serine-292, serine-293 and/or serine-294, or alternatively, singly, doubly or triply mutated serine-292, serine-293 and/or serine-294 to aspartic acid or to glutamic acid; (b) detecting the label of SERCA2 protein bound to the PDE3A1 protein or fragment thereof of (a) or free from the PDE3A1 protein or fragment thereof of (a); and (c) quantitatively determining the amount (i) labeled SERCA2 protein bound or free from the PDE3A1 protein or fragment thereof and comparing that amount (i) with an amount (ii) from an agent that does not compete with PDE3A1-SERCA2 complex formation, the amount (i) being less label bound to the SERCA2 protein or more label free from the SERCA2 protein being indicative that the agent of interest competes with the complex formation of PDE3A1 protein and SERCA2 protein thereby identifying the agent of interest that competes with the interaction of PDE3A1 protein and SERCA2 protein.

Also provided are methods for identifying an agent of interest that disrupts the interaction of PDE3A1 protein with SERCA2 protein. In one embodiment, the method comprises (a) contacting a PDE3A1 protein or fragment thereof comprising singly or doubly phosphorylated serine-292, serine-293 and/or serine-294, or alternatively, singly or doubly mutated serine-292, serine-293 and/or serine-294 to aspartic acid or to glutamic acid with a labeled SERCA2 protein, so as to produce a PDE3A1-SERCA2 complex; (b) contacting the PDE3A1-SERCA2 complex of (a) with one or more agents of interest that may compete with the interaction of PDE3A1 protein or fragment thereof and SERCA2 protein; (c) detecting the labeled SERCA2 protein in the PDE3A1-SERCA2 complex of (b) or the labeled SERCA2 protein released from the PDE3A1-SERCA2 complex of (b); (d) determining the amount (i) of the labeled SERCA2 protein remaining or released from the PDE3A1-SERCA2 complex of (c), and comparing that amount (i) with an amount (ii) from an agent that does not compete with PDE3A1-SERCA2 complex formation, the amount (i) being less label bound to the SERCA2 protein or more label free from the SERCA2 protein being indicative that the agent of interest competes with the complex formation of PDE3A1 protein and SERCA2 protein thereby identifying the agent of interest that disrupts the interaction of PDE3A1 protein with SERCA2 protein.

In accordance with the practice of the invention, the SERCA2 protein may be free or bound to other protein(s) or agent(s). In accordance with the practice of the invention, the PDE3A1 protein may be singly, doubly or triply phosphorylated at serine-292, serine-293, and/or serine-294. In some embodiments, the serine may be mutated to aspartic acid or glutamic acid.

Further, in accordance with the practice of the invention, the label may be a radioactive label, a colorimetric marker, a fluorophore, an antigen, an epitope or a product of an enzymatic reaction Further still, in accordance with the practice of the invention, the agent of interest may be a peptide, peptidomimetic or small molecule.

Yet further still the PDE3A1 protein or fragment thereof may be a polypeptide corresponding to amino acid position 146 to 1141 of SEQ ID NO:1 or fragment thereof. In another embodiment, the PDE3A1 protein or fragment thereof is a polypeptide corresponding to amino acid position 146 to 484 of SEQ ID NO:1. the PDE3A1 protein or fragment thereof comprises an amino acid sequence corresponding to amino acid position 288 to 297 of SEQ ID NO:1. In one embodiment of the invention, the PDE3A1 protein or fragment thereof is a recombinant protein. In yet a further embodiment, the PDE3A1 protein or fragment thereof is a polypeptide phosphorylated at amino acid corresponding to serine-292, serine-293 and/or serine-294 as provided in SEQ ID NO: 1. In a further embodiment, the PDE3A1 protein or fragment thereof is a polypeptide in which amino acid corresponding to serine-292, serine-293 and/or serine-294 as provided in SEQ ID NO:1 is/are substituted with aspartic acid.

In accordance with the practice of the invention, the screening methods may be performed in a high throughput format. In another embodiment, the screening method may be performed as a high content screen.

Lastly, in screens involving the amino-terminal sequence of the PDE3A1 protein, such screens may be performed in yeast cells, including screens (for example two-hybrid screens) to identify proteins that interact with the amino-terminal half of the PDE3A1 protein, or screens to identify small molecules or macromolecules (including peptides and peptidomimetics) that compete, interfere, disrupt or inhibit interaction between the amino-terminal half of PDE3A1 protein and a known interacting protein.

The invention provides methods for producing a peptide, polypeptide or protein of the invention comprising introducing the host vector system of the invention so as to produce the protein in the host (e.g., bacteria, baculovirus or yeast cells) and to recover the protein so produced.

The peptide or polypeptide of the invention described herein may be employed in accordance with the present invention by expression of such peptide or polypeptide of the invention in vivo, which is often referred to as gene therapy.

There are two major approaches to getting the nucleic acid (optionally contained in a vector) into the patient's cells: in vivo and ex vivo. For in vivo delivery the nucleic acid may be injected directly into the patient, usually at the sites where the peptide or polypeptide of the invention is required, i.e., the site of synthesis of the peptide, polypeptide or peptidomimetic of the invention, if known (such as, left ventricular region of a heart), and the site (e.g., wound) where biological activity of the peptide or polypeptide of the invention is needed. For ex vivo treatment, the patient's cells may be removed, the nucleic acid is introduced into these isolated cells, and the modified cells are administered to the patient either directly or, for example, encapsulated within porous membranes that are implanted into the patient. There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus, adenovirus or adeno-associated virus (AAV).

The currently preferred in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, 3' UTR sequence to enhance translation (such as WPRE) or post-translational modification of messenger. In addition, a viral vector such as a retroviral vector includes or may include a nucleic acid molecule that acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector may include a signal sequence for secretion of a polypeptide from a host cell in which it is placed. Preferably, the signal sequence for this purpose is a mammalian signal sequence. If secretion is not desired, such signal sequence is not included in the sequences used for the translation of the desired recombinant protein. Optionally, the vector construct may also include a signal that directs polyadenylation, as well as one or more restriction sites and a translation termination sequence. By way of example, such vectors will typically include a 5' LTR, a tRNA binding site, a packaging signal, an origin of second-strand DNA synthesis, and a 3' LTR or a portion thereof. Other vehicles can be used that are non-viral, such as cationic lipids, polylysine, and dendrimers.

Kits

According to another aspect of the invention, kits are provided. Kits according to the invention include package(s) comprising compositions of the invention.

The phrase "package" means any vessel containing compounds or compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in combination therapies as described herein. In certain embodiments, the package(s) is a container for intravenous administration. In still other embodiments compositions are provided in a polymeric matrix or in the form of a liposome.

The following examples are intended to illustrate the present invention, not to limit the scope of the invention in any way.

EXAMPLES

Example 1

Selective Targeting of PDE3A1 Blocks Hypertrophic Responses to Isoproterenol In neonatal rat ventricular myocytes, conventional PDE3 inhibition promotes cellular hypertrophy, which may be associated with adverse consequences in heart failure. We questioned what effect PDE3A1-selective inhibition would have. Faced with the absence of any known agent that selectively inhibits the catalytic activity of PDE3A1, we generated an RFP-tagged PDE3A1 construct with an F1004A substitution in the C-terminus that yields a catalytically inactive protein. The F1004A substitution is a change in the amino acid sequence of PDE3A1 at amino acid position 1004 from a phenylalanine to an alanine. We transfected neonatal rat ventricular myocytes with this dominant-negative construct to competitively block the protein-protein interactions that localize PDE3A1 to specific intracellular microdomains. In contrast to conventional PDE3 inhibition (e.g., cilostamide treatment in FIG. 5), expression of PDE3A1-F1004A (also called "PDE3A1-DN") did not induce cellular hypertrophy, and most surprisingly expression of PDE3A1-F1004A in fact blocked the hypertrophic response to norepinephrine (FIG. 5). This anti-hypertrophic effect was not seen when cells were transfected with PDE3A2-F1004A dominant negative mutant (also called "PDE3A2-DN"), a catalytically inactive mutant of PDE3A2 isoform with a change in the amino acid sequence of PDE3A2 at amino acid 1004 from a phenylalanine to an alanine (FIG. 5). These findings suggest that while nonselective PDE3 inhibition raises intracellular cAMP in a manner that promotes hypertrophic responses, PDE3A1 regulates a compartmentalized pool of cAMP that is not involved in these responses and actually attenuates them. To our knowledge, this is the first direct evidence that conventional PDE3 inhibition and isoform-selective targeting have different effects in cardiac myocytes, and that some of the adverse consequences of nonselective PDE3 inhibition may be averted by isoform-selective targeting involving protein-protein interactions.

The distinctions between PDE3 isoforms identified in our studies with respect to intracellular localization, regulation and protein-protein interactions suggest that they are likely to have unique roles in cAMP-mediated signaling in cardiac myocytes. PDE3A1, being localized to the sarcoplasmic reticulum, may preferentially regulate the phosphorylation of a limited, membrane-associated subset of the PDE3A phosphoproteome involved in intracellular $Ca^{2+}$ cycling, with less of a role in regulating the phosphorylation of cytosolic or mitochondrial proteins that may contribute to pro-apoptotic and other unwanted responses. Our observation that a dominant-negative PDE3A1 construct has anti-hypertrophic effects in neonatal myocytes, in contrast to the pro-hypertrophic effects of nonselective catalytic-site inhibition or pro-hypertrophic effects of expressing a dominant negative PDE3A2 construct, is further reason to suspect that selective targeting of the PDE3A1 isoform may avoid the adverse consequences of existing PDE3 inhibitors.[42,43]

Example 2

Introduction

A major limitation in the treatment of heart failure has been the failure of existing inotropic agents to improve survival. Inhibitors of PDE3, a cyclic nucleotide phosphodiesterase expressed in cardiac myocytes, augment contractility by raising intracellular cAMP content and increasing the phosphorylation of sarcoplasmic reticulum proteins involved in $Ca^{2+}$ cycling. Their long-term use, however, leads to an increase in mortality that is likely to result from their pro-apoptotic and pro-hypertrophic actions. Finding a way to obtain the benefits of PDE3 inhibition without these adverse consequences would constitute a major therapeutic advance.

Discovery, Target or Product

Several isoforms of PDE3, localized by protein-protein interactions to specific intracellular signaling domains, are expressed in human heart. While conventional PDE3 inhibitors, which have no selectivity for individual isoforms, promote cardiac myocyte hypertrophy, we recently discovered that selective targeting of the sarcoplasmic reticulum-associated isoform PDE3A1 by transfection with a catalytically inactive dominant-negative ('DN') construct has pronounced anti-hypertrophic effects. These effects are not seen when cardiac myocytes are transfected with a catalytically inactive form of PDE3A2, which is distributed diffusely within the cells. These findings suggest that an agent capable of selectively targeting PDE3A1—through its unique protein-interacting domains rather than its conserved catalytic site—may lead to a highly localized increase in sarcoplasmic reticulum-associated cAMP content, producing the inotropic benefits of PDE3 inhibition without the accompanying adverse effects.

REFERENCES

1. Francis S H, Blount M A, Corbin J D. Mammalian cyclic nucleotide phosphodiesterases: Molecular mechanisms and physiological functions. *Physiological reviews*. 2011; 91:651-690
2. Taira M, Hockman S C, Calvo J C, Belfrage P, Manganiello V C. Molecular cloning of the rat adipocyte hormone-sensitive cyclic gmp-inhibited cyclic nucleotide phosphodiesterase. *J Biol Chem.* 1993; 268:18573-18579
3. Meacci E, Taira M, Moos M, Jr., Smith C J, Movsesian M A, Degerman E, Belfrage P, Manganiello V. Molecular cloning and expression of human myocardial cgmp-inhibited camp phosphodiesterase. *Proceedings of the National Academy of Sciences of the United States of America.* 1992; 89:3721-3725
4. Simmerman H K, Jones L R. Phospholamban: Protein structure, mechanism of action, and role in cardiac function. *Physiol Rev.* 1998; 78:921-947
5. Takasago T, Imagawa T, Shigekawa M. Phosphorylation of the cardiac ryanodine receptor by camp-dependent protein kinase. *J Biochem (Tokyo).* 1989; 106:872-877
6. Beca S, Ahmad F, Shen W, Liu J, Makary S, Polidovitch N, Sun J, Hockman S, Chung Y W, Movsesian M, Murphy E, Manganiello V, Backx P H. Phosphodiesterase type 3a regulates basal myocardial contractility through interacting with sarcoplasmic reticulum calcium atpase type 2a 7. Bristow M R, Ginsburg R, Minobe W, Cubicciotti R S, Sageman W S, Lurie K, Billingham M E, Harrison D C, Stinson E B. Decreased catecholamine sensitivity and beta-adrenergic-receptor density in failing human hearts. *N Engl J Med.* 1982; 307:205-211
8. Bristow M R, Ginsburg R, Umans V, Fowler M, Minobe W, Rasmussen R, Zera P, Menlove R, Shah P, Jamieson S, et al. Beta 1- and beta 2-adrenergic-receptor subpopulations in nonfailing and failing human ventricular myocardium: Coupling of both receptor subtypes to muscle contraction and selective beta 1-receptor down-regulation in heart failure. *Circ Res.* 1986; 59:297-309
9. Ungerer M, Parruti G, Bohm M, Puzicha M, DeBlasi A, Erdmann E, Lohse M J. Expression of beta-arrestins and beta-adrenergic receptor kinases in the failing human heart. *Circ Res.* 1994; 74:206-213
10. Ungerer M, Bohm M, Elce J S, Erdmann E, Lohse M J. Altered expression of beta-adrenergic receptor kinase and beta 1-adrenergic receptors in the failing human heart. *Circulation.* 1993; 87:454-463
11. Neumann J, Schmitz W, Scholz H, von Meyerinck L, Doring V, Kalmar P. Increase in myocardial gi-proteins in heart failure. *Lancet.* 1988; 2:936-937
12. Feldman A M, Cates A E, Veazey W B, Hershberger R E, Bristow M R, Baughman K L, Baumgartner W A, Van Dop C. Increase of the 40,000-mol wt pertussis toxin substrate (g protein) in the failing human heart. *J Clin Invest.* 1988; 82:189-197
13. Feldman M D, Copelas L, Gwathmey J K, Phillips P, Warren S E, Schoen F J, Grossman W, Morgan J P. Deficient production of cyclic amp: Pharmacologic evidence of an important cause of contractile dysfunction in patients with end-stage heart failure. *Circulation.* 1987; 75:331-339
14. Danielsen W, v der Leyen H, Meyer W, Neumann J, Schmitz W, Scholz H, Starbatty J, Stein B, Doring V, Kalmar P. Basal and isoprenaline-stimulated camp content in failing versus nonfailing human cardiac preparations. *Journal of cardiovascular pharmacology.* 1989; 14:171-173
15. Bohm M, Reiger B, Schwinger R H, Erdmann E. Camp concentrations, camp dependent protein kinase activity, and phospholamban in non-failing and failing myocardium. *Cardiovasc Res.* 1994; 28:1713-1719
16. Beuckelmann D J, Nabauer M, Erdmann E. Intracellular calcium handling in isolated ventricular myocytes from patients with terminal heart failure. *Circulation.* 1992; 85:1046-1055
17. Baim D S, McDowell A V, Cherniles J, Monrad E S, Parker J A, Edelson J, Braunwald E, Grossman W. Evaluation of a new bipyridine inotropic agent—milrinone—in patients with severe congestive heart failure. *N Engl J Med.* 1983; 309:748-756
18. Benotti J R, Grossman W, Braunwald E, Davolos D D, Alousi A A. Hemodynamic assessment of amrinone. A new inotropic agent. *N Engl J Med.* 1978; 299:1373-1377
19. Jaski B E, Fifer M A, Wright R F, Braunwald E, Colucci W S. Positive inotropic and vasodilator actions of milrinone in patients with severe congestive heart failure. Dose-response relationships and comparison to nitroprusside. *J Clin Invest.* 1985; 75:643-649
20. Sinoway L S, Maskin C S, Chadwick B, Forman R, Sonnenblick E H, Le Jemtel T H. Long-term therapy with a new cardiotonic agent, win 47203: Drug-dependent improvement in cardiac performance and progression of the underlying disease. *J Am Coll Cardiol.* 1983; 2:327-331
21. Maskin C S, Sinoway L, Chadwick B, Sonnenblick E H, Le Jemtel T H. Sustained hemodynamic and clinical effects of a new cardiotonic agent, win 47203, in patients with severe congestive heart failure. *Circulation.* 1983; 67:1065-1070
22. Anderson J L. Hemodynamic and clinical benefits with intravenous milrinone in severe chronic heart failure: Results of a multicenter study in the united states. *American heart journal.* 1991; 121:1956-1964
23. Monrad E S, McKay R G, Baim D S, Colucci W S, Fifer M A, Heller G V, Royal H D, Grossman W. Improvement in indexes of diastolic performance in patients with congestive heart failure treated with milrinone. *Circulation.* 1984; 70:1030-1037
24. Amsallem E, Kasparian C, Haddour G, Boissel J P, Nony P. Phosphodiesterase iii inhibitors for heart failure. *Cochrane database of systematic reviews (Online).* 2005: CD002230
25. del Monte F, Lebeche D, Guerrero J L, Tsuji T, Doye A A, Gwathmey J K, Hajjar R J. Abrogation of ventricular arrhythmias in a model of ischemia and reperfusion by targeting myocardial calcium cycling. *Proceedings of the National Academy of Sciences of the United States of America.* 2004; 101:5622-5627
26. Lyon A R, Bannister M L, Collins T, Pearce E, Sepehripour A H, Dubb S S, Garcia E, O'Gara P, Liang L, Kohlbrenner E, Hajjar R J, Peters N S, Poole-Wilson P A, Macleod K T, Harding S E. SERCA2a gene transfer decreases sarcoplasmic reticulum calcium leak and reduces ventricular arrhythmias in a model of chronic heart failure. *Circulation. Arrhythmia and electrophysiology.* 2011; 4:362-372
27. Dorn G W, 2nd. Apoptotic and non-apoptotic programmed cardiomyocyte death in ventricular remodelling. *Cardiovasc Res.* 2009; 81:465-473
28. Ding B, Abe J, Wei H, Xu H, Che W, Aizawa T, Liu W, Molina C A, Sadoshima J, Blaxall B C, Berk B C, Yan C. A positive feedback loop of phosphodiesterase 3 (pde3) and inducible camp early repressor (icer) leads to cardiomyocyte apoptosis. *Proceedings of the National Academy of Sciences of the United States of America.* 2005; 102: 14771-14776
29. Ding B, Abe J, Wei H, Huang Q, Walsh R A, Molina C A, Zhao A, Sadoshima J, Blaxall B C, Berk B C, Yan C. Functional role of phosphodiesterase 3 in cardiomyocyte apoptosis: Implication in heart failure. *Circulation.* 2005; 111:2469-2476
30. Oikawa M, Wu M, Lim S, Knight W E, Miller C L, Cai Y, Lu Y, Blaxall B C, Takeishi Y, Abe J, Yan C. Cyclic nucleotide phosphodiesterase 3a1 protects the heart against ischemia-reperfusion injury. *Journal of molecular and cellular cardiology.* 2013; 64:11-19
31. Schmidt M, Dekker F J, Maarsingh H. Exchange protein directly activated by camp (epac): A multidomain camp mediator in the regulation of diverse biological functions. *Pharmacological reviews.* 2013; 65:670-709
32. Breckler M, Berthouze M, Laurent A C, Crozatier B, Morel E, Lezoualc'h F. Rap-linked camp signaling epac proteins: Compartmentation, functioning and disease implications. *Cellular signalling.* 2011; 23:1257-1266
33. Oestreich E A, Malik S, Goonasekera S A, Blaxall B C, Kelley G G, Dirksen R T, Smrcka A V. Epac and phospholipase cepsilon regulate ca2+ release in the heart by activation of protein kinase cepsilon and calcium-calmodulin kinase ii. *The Journal of biological chemistry.* 2009; 284:1514-1522
34. Oestreich E A, Wang H, Malik S, Kaproth-Joslin K A, Blaxall B C, Kelley G G, Dirksen R T, Smrcka A V. Epac-mediated activation of phospholipase c(epsilon) plays a critical role in beta-adrenergic receptor-dependent enhancement of ca2+ mobilization in cardiac myocytes. *The Journal of biological chemistry.* 2007; 282:5488-5495
35. Pereira L, Metrich M, Fernandez-Velasco M, Lucas A, Leroy J, Perrier R, Morel E, Fischmeister R, Richard S, Benitah J P, Lezoualc'h F, Gomez A M. The camp binding protein epac modulates ca2+ sparks by a ca2+/calmodulin kinase signalling pathway in rat cardiac myocytes. *The Journal of physiology.* 2007; 583:685-694
36. Cazorla O, Lucas A, Poirier F, Lacampagne A, Lezoualc'h F. The camp binding protein epac regulates cardiac myofilament function. *Proceedings of the National Academy of Sciences of the United States of America.* 2009; 106:14144-14149
37. Morel E, Marcantoni A, Gastineau M, Birkedal R, Rochais F, Garnier A, Lompre A M, Vandecasteele G, Lezoualc'h F. Camp-binding protein epac induces cardiomyocyte hypertrophy. *Circulation research.* 2005; 97:1296-1304
38. Pereira L, Ruiz-Hurtado G, Morel E, Laurent A C, Metrich M, Dominguez-Rodriguez A, Lauton-Santos S, Lucas A, Benitah J P, Bers D M, Lezoualc'h F, Gomez A M. Epac enhances excitation-transcription coupling in cardiac myocytes. *Journal of molecular and cellular cardiology.* 2012; 52:283-291
39. Chruscinski A J, Singh H, Chan S M, Utz P J. Broadscale phosphoprotein profiling of beta adrenergic receptor (beta-ar) signaling reveals novel phosphorylation and dephosphorylation events. *PloS one.* 2013; 8:e82164
40. Netherton S J, Sutton J A, Wilson L S, Carter R L, Maurice D H. Both protein kinase a and exchange protein activated by camp coordinate adhesion of human vascular endothelial cells. *Circulation research.* 2007; 101:768-776
41. Wilson L S, Baillie G S, Pritchard L M, Umana B, Terrin A, Zaccolo M, Houslay M D, Maurice D H. A phosphodiesterase 3b-based signaling complex integrates exchange protein activated by camp 1 and phosphatidylinositol 3-kinase signals in human arterial endothelial cells. *The Journal of biological chemistry.* 2011; 286:16285-16296
42. Roubille F, Tardif J C. New therapeutic targets in cardiology: Heart failure and arrhythmia: Hcn channels. *Circulation.* 2013; 127:1986-1996
43. Hayes J S, Brunton L L, Mayer S E. Selective activation of particulate camp-dependent protein kinase by isoproterenol and prostaglandin e1. *J Biol Chem.* 1980; 255:5113-5119
44. Buxton I L, Brunton L L. Compartments of cyclic amp and protein kinase in mammalian cardiomyocytes. *J Biol Chem.* 1983; 258:10233-10239
45. Nikolaev V O, Moshkov A, Lyon A R, Miragoli M, Novak P, Paur H, Lohse M J, Korchev Y E, Harding S E, Gorelik J. Beta2-adrenergic receptor redistribution in heart failure changes camp compartmentation. *Science.* 2010; 327:1653-1657
46. Zaccolo M, Pozzan T. Discrete microdomains with high concentration of camp in stimulated rat neonatal cardiac myocytes. *Science.* 2002; 295:1711-1715
47. Mongillo M, McSorley T, Evellin S, Sood A, Lissandron V, Terrin A, Huston E, Hannawacker A, Lohse M J, Pozzan T, Houslay M D, Zaccolo M. Fluorescence resonance energy transfer-based analysis of camp dynamics in live neonatal rat cardiac myocytes reveals distinct functions of compartmentalized phosphodiesterases. *Circulation research.* 2004; 95:67-75
48. Rochais F, Abi-Gerges A, Horner K, Lefebvre F, Cooper D M, Conti M, Fischmeister R, Vandecasteele G. A specific pattern of phosphodiesterases controls the camp signals generated by different gs-coupled receptors in adult rat ventricular myocytes. *Circ Res.* 2006; 98:1081-1088
49. Mongillo M, Tocchetti C G, Terrin A, Lissandron V, Cheung Y F, Dostmann W R, Pozzan T, Kass D A, Paolocci N, Housley M D, Zaccolo M. Compartmentalized phosphodiesterase-2 activity blunts beta-adrenergic cardiac inotropy via an no/cgmp-dependent pathway. *Circ Res.* 2006; 98:226-234
50. Stangherlin A, Gesellchen F, Zoccarato A, Terrin A, Fields L A, Berrera M, Surdo N C, Craig M A, Smith G, Hamilton G, Zaccolo M. Cgmp signals modulate camp levels in a compartment-specific manner to regulate catecholamine-dependent signaling in cardiac myocytes. *Circulation research.* 2011; 108:929-939
51. Terrenoire C, Housley M D, Baillie G S, Kass R S. The cardiac iks potassium channel macromolecular complex includes the phosphodiesterase pde4d3. *The Journal of biological chemistry.* 2009; 284:9140-9146
52. Lehnart S E, Wehrens X H, Reiken S, Warrier S, Belevych A E, Harvey R D, Richter W, Jin S L, Conti M, Marks A R. Phosphodiesterase 4d deficiency in the ryanodine-receptor complex promotes heart failure and arrhythmias. *Cell.* 2005; 123:25-35
53. Leroy J, Richter W, Mika D, Castro L R, Abi-Gerges A, Xie M, Scheitrum C, Lefebvre F, Schittl J, Mateo P, Westenbroek R, Catterall W A, Charpentier F, Conti M, Fischmeister R, Vandecasteele G. Phosphodiesterase 4b in the cardiac 1-type ca(2)(+) channel complex regulates ca(2)(+) current and protects against ventricular arrhythmias in mice. *The Journal of clinical investigation.* 2011; 121:2651-2661
54. Housley M D, Baillie G S, Maurice D H. Camp-specific phosphodiesterase-4 enzymes in the cardiovascular system: A molecular toolbox for generating compartmentalized camp signaling. *Circ Res.* 2007; 100:950-966
55. Housley M D. Underpinning compartmentalised camp signalling through targeted camp breakdown. *Trends Biochem Sci.* 2010; 35:91-100
56. Wechsler J, Choi Y H, Krall J, Ahmad F, Manganiello V C, Movsesian M A. Isoforms of cyclic nucleotide phosphodiesterase pde3a in cardiac myocytes. *The Journal of biological chemistry.* 2002; 277:38072-38078
57. Kenan Y, Murata T, Shakur Y, Degerman E, Manganiello V C. Functions of the n-terminal region of cyclic nucleotide phosphodiesterase 3 (pde 3) isoforms. *The Journal of biological chemistry.* 2000; 275:12331-12338
58. Shakur Y, Takeda K, Kenan Y, Yu Z X, Rena G, Brandt D, Housley M D, Degerman E, Ferrans V J, Manganiello V C. Membrane localization of cyclic nucleotide phosphodiesterase 3 (pde3). Two n-terminal domains are required for the efficient targeting to, and association of, pde3 with endoplasmic reticulum. *The Journal of biological chemistry.* 2000; 275:38749-38761
59. Han S J, Vaccari S, Nedachi T, Andersen C B, Kovacina K S, Roth R A, Conti M. Protein kinase b/akt phosphorylation of pde3a and its role in mammalian oocyte maturation. *The EMBO journal.* 2006; 25:5716-5725

60. Pozuelo Rubio M, Campbell D G, Morrice N A, Mackintosh C. Phosphodiesterase 3a binds to 14-3-3 proteins in response to pma-induced phosphorylation of ser428. *Biochem J*. 2005; 392:163-172
61. Hunter R W, Mackintosh C, Hers I. Protein kinase c-mediated phosphorylation and activation of pde3a regulate camp levels in human platelets. *The Journal of biological chemistry*. 2009; 284:12339-12348
62. Taira M, Hockman S C, Calvo J C, Taira M, Belfrage P, Manganiello V C. Molecular cloning of the rat adipocyte hormone-sensitive cyclic gmp-inhibited cyclic nucleotide phosphodiesterase. *The Journal of biological chemistry*. 1993; 268:18573-18579
63. Leroy M J, Degerman E, Taira M, Murata T, Wang L H, Movsesian M A, Meacci E, Manganiello V C. Characterization of two recombinant pde3 (cgmp-inhibited cyclic nucleotide phosphodiesterase) isoforms, rcgip1 and hcgip2, expressed in nih 3006 murine fibroblasts and sf9 insect cells. *Biochemistry*. 1996; 35:10194-10202
64. Hambleton R, Krall J, Tikishvili E, Honeggar M, Ahmad F, Manganiello V C, Movsesian M A. Isoforms of cyclic nucleotide phosphodiesterase pde3 and their contribution to camp hydrolytic activity in subcellular fractions of human myocardium. *J Biol Chem*. 2005; 280:39168-39174
65. Roger V L, Go A S, Lloyd-Jones D M, Adams R J, Berry J D, Brown T M, Carnethon M R, Dai S, de Simone G, Ford E S, Fox C S, Fullerton H J, Gillespie C, Greenlund K J, Hailpern S M, Heit J A, Ho P M, Howard V J, Kissela B M, Kittner S J, Lackland D T, Lichtman J H, Lisabeth L D, Makuc D M, Marcus G M, Marelli A, Matchar D B, McDermott M M, Meigs J B, Moy C S, Mozaffarian D, Mussolino M E, Nichol G, Paynter N P, Rosamond W D, Sorlie P D, Stafford R S, Turan T N, Turner M B, Wong N D, Wylie-Rosett J. Heart disease and stroke statistics—2011 update: A report from the american heart association. *Circulation*.
66. Roger V L. Epidemiology of heart failure. *Circulation research*. 2013; 113:646-659

Example 3

Materials and Methods

Use of human heart samples in these studies was approved by review committees at NHLBI, NIH, and the University of Utah.

Material

[γ-$^{32}$P]ATP (3000 Ci/mmol) was obtained from MP Biomedicals (Solon, Ohio, U.S.A.); SuperSignal® Westpico and Westfemto chemiluminescent reagents were from Pierce (Rockford, Ill., U.S.A.); Anti-prohibitin, CD31, PLB, p-PLB, AKAP-LBC, and AKAP18 antibodies were from Abcam (Cambridge, Mass.). Antibodies to caveolin-1, caveolin-3, PP2A, PKARII, PKARI, BiP and GM130 were purchased from BD Biosciences (San Diego, Calif.); anti-β1-AR, β2-AR, Gαl, GαS, adenylate cyclase V/VI, 14-3-3, PP1, and HSP90 antibodies were from Santa Cruz Biotechnology; SERCA2 antibody was from Affinity Bioreagents; β3-AR antibody was from Chemicon; CX-43 antibody was from Thermoscientific; Calnexin and phosphor-PKA substrate antibodies were from Cell Signaling; Desmin and SM-actin antibodies were obtained from Dako. Flag antibodies were from Sigma-Aldrich. Affinity purified rabbit polyclonal antibody to human PDE3A (accession no. AAA35912) was generated against peptide corresponding to amino acids 1127-1141 of SEQ ID NO: 1 (GKPRGEE-IPTQKPDQ) CT domain (C terminal domain). rPKAc and rSERCA2 were obtained from Calbiochem and Abnova, respectively. Other materials were obtained as indicated.

Methods

Preparation of Subcellular Fractions of Human Myocardium

Human myocardium was obtained from the left ventricular free wall of explanted hearts from patients with idiopathic dilated cardiomyopathy undergoing cardiac transplantation (University of Utah). Normal human heart samples were also obtained from Capital Biosciences, Inc (Rockville, Md.). Heart tissues were quickly washed in ice-cold PBS, chopped with scissors and homogenized (4 ml/g tissue) at 4° C. in buffer A (0.29 M sucrose, 10 mM MOPS, 2 mM EGTA, Roche protease inhibitor cocktail, pH 7.0) with a rotor-stator homogenizer (Omni International, Marietta, Ga., USA) at 30,000 rpm (60-80 seconds, on ice), followed by homogenization (on ice, 20 strokes in a glass Dounce homogenizer). Homogenates were centrifuged (11,000×g, 15 min) in a Beckman JA-20 rotor. Supernatants were further centrifuged (150,000×g, 1 h) in a Beckman 55.2 Ti rotor, yielding cytosolic fractions and pellets. Pellets were resuspended by hand homogenization (glass-glass) in two volumes (relative to starting material) of buffer A without EGTA. Following resedimentation (150,000×g, 1 h), the pellet, i.e., 'myocardial membrane fraction', was suspended in buffer A (without EGTA) using a dounce homogenizer and stored at −80° C. Each preparation was made from combined tissues from at least three different hearts. For some experiments, myocardial membranes were solubilized in buffer B (50 mM HEPES, 50 mM sucrose, 1 mM EDTA, 10 mM pyrophosphate, 5 mM NaF, 100 mM NaCl, 5 mM MgCl2, 0.1 µM okadaic acid, Roche protease inhibitor cocktail, pH 7.5). Myocardial membranes were solubilized by homogenization (using a Dounce homogenizer, 20 strokes) and incubation/rotation of homogenates with Nonidet P40 (v/v, 1% final)(Thermoscientific) for 1 h at 4° C. Solubilized membrane proteins (supernatants) were obtained by centrifugation [24000 rev/min for 30 min at 4° C., using a SW41 Ti rotor (Beckman)].

For isolation of SR vesicles, 11,000×g supernatants were centrifuged (45 min, 43,666×g) in a Beckman SW41 rotor, as described (15). The resultant pellet was resuspended in buffer containing 0.6 M KCL and 20 mM Tris (pH 6.8) and centrifuged for (45 min, 43,666×g). The final washed pellet containing SR fractions was suspended in buffer A and stored at −80° C.

cAMP PDE Assay

PDE3 activity, (that portion of total PDE activity inhibited by 1.0 µM cilostamide, a selective PDE3 inhibitor), was measured by modification of our published method (16), using 0.1 µM [$^3$H] cAMP (35000 cpm) as substrate. PDE activity is expressed as pmol cAMP hydrolyzed/min/mg.

Immunoprecipitation and Immunoblotting

Solubilized myocardial membranes were cleared by incubation for 1 h at 4° C. with 5 µg nonimmune IgG, and then with 50 µl Protein G-Magnetic beads (Thermoscientific) for 30 min, before placing the tube into a magnetic stand to collect the beads against the side of the tube. Cleared fractions were incubated overnight at 4° C. with specified antibodies or with non-immune IgG, followed by incubation with fresh Protein-G-Magnetic beads for 1 h before placing the tube into a magnetic stand to collect the beads. After washing (3×, Buffer B), Protein-G-Magnetic-beads-bound, immunoprecipitated, proteins were eluted by boiling in 200 µl Laemmli's SDS buffer, and samples (15 µl) were subjected to SDS-PAGE, electro-transferred to nitrocellulose membranes (Invitrogen), and immunoblotted sequentially with appropriate primary antibodies and HRP-labeled secondary antibody (Thermoscientific). Immunoreactive proteins were reacted with Supersignal® Westpico or Westfemto chemiluminescent reagents (Thermoscientific); signals were detected with Image reader LAS3000 (GE Healthcare).

Effect of cAMP and Recombinant PKA Catalytic Subunit (rPKAc) on $^{45}Ca^{2+}$ Uptake or SERCA Activity SR fractions (50~100 g) were incubated (30 min, 30° C.) without or with 250 units of rPKAc or indicated concentrations of cAMP in buffer containing 10 mM imidazole-HCl (pH 7.0), 0.1 μM okadaic acid, 10 mM MgCl2, 5 mM DTT, 0.5 mM ATP and 1× phosphatase inhibitor cocktail. The reaction mixture was centrifuged (100,000×g, 30 min, 40 C), and the resulting pellets were resuspended in 0.3 μM sucrose, 10 mM K-PIPES buffer containing 1× phosphatase inhibitor cocktail, pH 7.0, for $Ca^{2+}$ uptake and SERCA activity assays.

Measurement of $^{45}Ca^{2+}$ Uptake in SR Vesicles

Oxalate-dependent $Ca^{2+}$ uptake was quantified as described previously (17). Briefly, SR vesicles (50 μl, 10-20 μg protein), prepared as described above, were incubated at 37° C. for 0.5-3 min in 0.4 ml $Ca^{2+}$ uptake buffer, consisting of 50 mM imidazole-HCl, pH7.0, 100 mM KCl, 6 mM MgCl2, 10 mM $NaN_3$ (to inhibit mitochondrial Ca2+ uptake), 10 mM potassium oxalate; 20 μM ruthenium red (to inhibit SR Ca2+ release); 0.1 mM EGTA; $^{45}CaCl_2$ (10,000 dpm/nmol) (Perkin Elmer, Cat#NEZ013), and unlabeled $CaCl_2$ (0.1~1 μM free $Ca^{2+}$). Uptake was initiated by adding 50 mM ATP (50 μl) and terminated at indicated times by filtration through 0.45 μm Millipore filters. After washing four times with 4 ml buffer containing 140 mM KCl, 10 mM NaCl, 2 mM $MgCl_2$, 1 mM $CaCl_2$ and 50 mM imidazole-HCl, (pH 7.0), radioactivity retained on the filters was quantified by liquid scintillation counting. Free $[Ca^{2+}]$ was calculated using a program obtained at http://www.stanford.edu/~cpatton/webmaxc/webmaxcS.htm.

SERCA Activity Assay $Ca^{2+}$-ATPase activity in SR fractions was determined by measuring the amount of $P_i$ released after addition of ATP, using the malchite green ATPase method (18). Samples were assayed in the presence or absence of thapsigargin (10 μM), since SERCA2 activity was determined as that portion of total activity inhibited by thapsigargin. The assay mixture (total volume, 125 μl) contained 0.125 M KCl, 20 mM imidazole, pH 7.0, 0.1 mM EGTA, 0.103 mM $CaCl_2$, 1 μM ionomycin and 10 μg SR. To initiate the reaction, 25 μl of substrate ($Mg^{2+}$-ATP) was added to a final concentration of 0.25 mM. The mixture was incubated at room temperature for 0.5-3 min. The reaction was terminated by adding 25 μl of 250 g/L TCA, vortexed quickly, and centrifuged (8,000× g, 3 min). Supernatants (20 μl) were added to 96 well plates, followed by color reagent (100 μl/sample), which consisted of 54 mM ammonium molybdate and 0.73 mM Malachite green. After 1 min, Na-citrate (340 g/L, 10 μl) was added, with gentle shaking (room temperature for more than 20 min), after which plates were scanned at 650 nm. $P_i$ was calculated by converting OD650 to nanomoles by means of a standard curve.

cAMP-Dependent Phosphorylation of Endogenous PLB

Resuspended myocardial membranes (20 g protein) were phosphorylated in buffer containing 50 mM HEPES, 5 mM $MgCl_2$, 50 mM sucrose, 100 mM NaCl, 5 mM NaF, 10 mM $PP_i$, 1 mM EDTA, pH 7.6. After incubation (2 min, 30° C.) in the absence or presence of cilostamide (1 μM) or rolipram (10 μM), 0.5 mM ATP and 0.1 μM cAMP were added as indicated, and incubations (50 μl final volume) were continued for 30 min. Reactions were terminated by addition of SDS-containing buffer (25 μl). Samples were immediately boiled (5 min), and subjected to SDS PAGE. Phosphorylation of Ser-16 PLB and endogenous PLB, PKAc, and PDE3A proteins were identified by Western immunoblotting.

Immunohistochemistry

Frozen heart blocks were prepared from snap frozen normal human heart samples obtained from Capital Biosciences, Inc, and sections were made at a thickness of 10 m using a microtome at −25° C. Paraformaldehyde-fixed cryostat heart sections were washed in PBS (3×5 min), blocked and permeabilized in 10% donkey serum containing 0.05% Triton X-100 (6 h, 4° C.). Slides were incubated in blocking buffer with primary antibody overnight and washed with PBS (3×5 min) before incubating in blocking buffer for 2 h with secondary antibody (Alexa Fluor 488 or Alexa fluor 594; Molecular Probes). PDE3A antibody against human PDE3A aa1127-1141 of SEQ ID NO: 1 (GKPRGEEIPTQK-PDQ; CT, C-terminus) was used. As controls, slides were incubated with nonimmune IgG or with primary antibodies incubated with blocking (immunizing) peptides, prior to staining with secondary antibody. For peptide blocking/competition experiments, approximately 20 g anti-PDE3A-CT antibody was combined with 100 g of blocking peptide in a small volume (500 μl) of PBS and incubated (2 h, room temperature or overnight, 4° C.). After blocking with the immunizing peptides, antibody/peptide mixtures were diluted into blocking buffer and used for staining of samples.

Slides were viewed with a Zeiss LSM510 laser scanning confocal microscope.

Gel Filtration Chromatography on Superose 6 Columns

Solubilized myocardial membranes (1.0 ml, 3 mg total protein), prepared as described above, were applied to a Superose 6 HR 10/30 column (ÄKTA FPLC System, GE healthcare) that was equilibrated and eluted with buffer C (buffer B without sucrose, containing 150 mM NaCl and 1% NP-40) (FIG. 7). Chromatography of solubilized myocardial membranes (3 mg) on Superose 6 HR was repeated 2 times and LMW fractions (#24-34) were pooled and concentrated via centriprep. The concentrated fractions were split, and, after treatment without or with rPKAc, were used for re-chromatography on S6 columns (FIG. 8). For immunoprecipitation studies, LMW fractions from two similar experiments were also pooled, concentrated, split, and, after treatment without or with rPKAc, used to study co-immunoprecipitation of PDE3A with components of the SERCA2/AKAP18 signalosome (FIG. 9). Cytosolic fractions (1.0 ml, 3 mg total protein), prepared as described above, were also applied to Superose 6 which was equilibrated and eluted with buffer D (buffer C, without NP40) (FIG. 7). Portions of the fractions (0.5 ml) were used for assay of PDE3 activity or SDS PAGE/Western blotting (using affinity-purified rabbit anti-PDE3A and other indicated antibodies). In some experiments, portions of eluted HMW and LMW peaks from solubilized membrane and cytosol fractions were pooled, concentrated, and immunoprecipitation was carried out with anti-PDE3A-CT antibody and Protein-G-Magnetic beads as described above, followed by immunoblotting with anti-phospho-PKA-substrate and anti-PDE3A antibodies.

In Vitro Phosphorylation of PDE3A

PDE3A immunoprecipitated from solubilized myocardial membranes (500 μg) was incubated for 1 h at 30° C. in the absence or presence of 250 units rPKAc [One unit is defined as the amount of enzyme required to transfer 1 pmol phosphate to PKA peptide (GRTGRRNSI; SEQ ID NO: 3) per min at 30° C.] or rPKAc plus 10 µM PKI (PKA inhibitor) in phosphorylation buffer (50 mM HEPES, pH 7.5, 5 mM MgCl$_2$, 100 mM NaCl, 1 mM EDTA, 10 mM PP$_i$, 5 mM NaF, 0.1 µM okadaic acid) without or with 200 µM ATP or 200 µM ATP supplemented with [γ$^{32}$P] ATP (10 µCi per reaction; 3000 Ci/mmol stock). Reaction mixtures were boiled in sample buffer and subjected to SDS-PAGE. Phosphorylation of PDE3A was detected by scanning the wet gels on a Phospho Imager (GE Healthcare). Proteins on wet gels were then electrophoretically transferred to nitrocellulose membranes, and PDE3A was identified by Western blotting using anti-PDE3A antibody.

Co-Immunoprecipitation of PDE3A with Components of SERCA2 Regulatory Signalosomes from Pooled LMW Fractions after Incubation with or without rPKAc Pooled LMW Superose 6 fractions from solubilized myocardial membranes were prepared as described above and incubated without (control) or with rPKAc in buffer containing 200 µM ATP for 1 h at 30° C. At the completion of these reactions, fractions were cleared, and incubated overnight with nonimmune IgG (10 µg) or anti-PDE3A-CT antibody (10 g) before incubation (1 h) with Protein-G-magnetic beads. Protein-G-Magnetic-beads-bound, immunoprecipitated proteins were washed, eluted, and samples (15 µl) were immunoblotted with indicated antibodies as described above. Total membrane protein (10 µg, input) were loaded on gels as controls.

Co-Immunoprecipitation of Flag-Tagged Recombinant Human PDE3A (rhPDE3A) Variants and rSERCA2 after Incubation with or without rPKAc Flag-tagged rhPDE3A1 and its phosphorylation site mutants [rhPDE3A1-S292A/293A (M1), rhPDE3A1-S312A (M2), rhPDE3A1-S428A (M3), rhPDE3A1-S438A (M4), rhPDE3A1-S292A/293A/312A/438A (M5) open reading frame [accession #NP_000912] was synthesized by Genscript, Inc (Piscataway, N.J.), subcloned into pAcSG2 baculoviral expression vector. Flag-tagged rhPDE3A variants and phosphorylation site mutants were expressed in SF21 cells [(10-20)×106 SF21 cells/75-cm2 flask] as described (19,20). SF21 cells were harvested, sedimented (10 min, 1000×g, 4° C.), washed twice with ice-cold PBS, resuspended, homogenized (in a Dounce homogenizer) in buffer B and sonicated vector, and expressed in SF21 cells (19). A comparison of the translated sequences of human AKAP18γ (AC NP_057461 and AK300587; 348 aa residues) and rat AKAP18δ (3) (AC QJP77; 352 aa residues) indicate that eight of the first twelve aa residues of human AKAP18γ and rat AKAP18δ are identical, and that the proteins are homologous (~74% aa identity). SF21 cell extracts, which contained his-tagged-rAKAP18δ, were prepared as described above. Flag-tagged rhPDE3A1 (usually 50 arbitrary (u) units) was incubated (30 min, 30° C.) with rAKAP18δ (200 µl, containing 50 ng of recombinant protein), with or without different concentrations of rPKAc (final volume, 300 µl) in buffer B containing 2 mM DTT and 200 µM ATP. Reactions were stopped by dilution of reaction mixtures to 1.0 ml with buffer B containing 1 mg/ml SF21 cell lysates, and cleared as described above (cf 'Immunoprecipitation and immunoblotting' subsection). His-tagged rAKAP18δ was immunoprecipitated with anti-his Mab Mag-beads (Genscript). Anti-his Mab Mag beads-bound immunoprecipitates were washed, collected, and anti-his Mab Mag-beads-bound proteins were eluted by boiling in Laemmli's SDS buffer (100 µl) and samples (15 µl) of immunoprecipitated proteins as well as of reaction mixtures ('input proteins') were immunoblotted with indicated antibodies as described above.

LC-MS/MS Analysis of PDE3A Immunoprecipitates

PDE3A immunoprecipitates were separated by 4-20% SDS-PAGE; proteins were stained with Coomassie SimplyBlue™ SafeStain (Invitrogen, Cat#LC6060) for 1 hour at RT, followed by destaining (overnight, RT) in pure water. Sequential gel slices were cut out according to molecular weight. Gel slices were diced into small cube pieces (1-2 mm$^2$) and placed in 1.5 ml tubes. Gel pieces were destained by 25 mM NH$_4$HCO$_3$/50% acentonitrile (3×10 min), and vortexed occasionally. Using gel-loading tips, supernatants were discarded. Gel pieces were dessicated by speed vac. After reduction in buffer (10 mM DTT, 25 mM NH$_4$HCO3; 56° C., 1 h) and alkylation (55 mM iodoacetamide, 25 mM NH$_4$HCO$_3$; 45 min, RT), gel pieces were dessicated by speed vac and digested with 10 ng/µl trypsin (Promega) (overnight, 37° C.).

Tryptic peptides were released from the gels upon vortexing and sonication. Released peptides were purified, concentrated, and desalted by reversed phase C18 ZipTip (Millipore). Peptide samples were stocked in 0.1% formic acid (FA) for LC-MS/MS analysis (LTQ Orbitrap Velos mass spectrometer, Thermofisher Scientific, San Jose, Calif.) using CID fragmentation. At least two peptides were obtained for each protein with MS/MS. Proteins were identified from the acquired spectra with the MASCOT database search function.

Results

PDE3A Co-Localizes with PLB, SERCA2 and AKAP18 in the Z-Bands of Human Cardiac Myocytes The intracellular distribution of PDE3A in human cardiac myocytes was examined by immunostaining with anti-PDE3A-CT antibodies (FIG. 6). Consistent with our previous studies (21,22), co-staining with anti-PDE3A and anti-desmin antibodies demonstrated that PDE3A is distributed in a striated pattern in the Z-lines of these cells (FIG. 6A, B), with little co-localization with myomesin (M-line marker protein) (FIG. 6B). PDE3A co-localized with PLB, SERCA2 and an AKAP18 variant that was detected by antibodies to human AKAP18 (Abcam: Ab 30987) (FIG. 6A, B).

PDE3 Inhibition Potentiates cAMP-Dependent Phosphorylation of PLB and its Stimulation of Ca$^{2+}$ Uptake in Human Myocardial Membranes The effects of PDE3 inhibition on PLB phosphorylation and Ca$^{2+}$ uptake were examined in microsomes prepared from human left ventricular myocardium. At 0.1 µM cAMP, phosphorylation of PLB at S16 by endogenous PKA was stimulated by the PDE3-selective inhibitor cilostamide (FIG. 7A, 7B). Since PDE4 has also been found to co-immunoprecipitate with PLB in subcellular preparations from human myocardium (23), we tested the effect of the PDE4-specific inhibitor rolipram on PLB phosphorylation, and found no effect (FIG. 7A, 7B). This result corresponds to the lower amount of rolipram-sensitive cAMP-hydroltyic activity relative to cilostamide-sensitive cAMP-hydrolytic activity in these preparations (FIG. 7C). cAMP increased ATP-dependent, oxalate-supported Ca$^{2+}$ uptake (FIG. 7D), and this effect was potentiated by cilostamide (FIG. 7E). Addition of rPKAc stimulated both Ca$^{2+}$ uptake and SERCA2 activity (FIG. 7F). These results indicate that PDE3 has a specific role in regulating phosphorylation of PLB by cAMP/PKA and the consequent stimulation of Ca$^{2+}$ uptake in human myocardium.

Phosphorylated PDE3A Isoforms Co-Elute with PLB, SERCA2 and AKAP18 in High-Molecular-Weight Peaks from Solubilized Human Myocardial Membranes In previous studies, we showed that the phosphorylation of rPDE3A isoforms in transfected HEK293 cells promotes their interactions with other proteins (14). To address whether phosphorylation might promote the integration of PDE3A into multiprotein SERCA2 complexes in cardiac myocytes, we analyzed cytosolic and NP40-solubilized membrane proteins from human left ventricular myocardium by Superose (S6) gel-filtration chromatography (FIG. 8). As seen in FIG. 8A, PDE3 activity in solubilized myocardial membrane proteins was recovered in distinct HMW (~3000 kD) and LMW (~700 kD) peaks. Western blotting with anti-PDE3A antibodies indicated that the HMW and LMW peaks contained all three PDE3A isoforms. In contrast, upon S6 chromatography of cytosolic fractions, from which PDE3A1 is absent, PDE3A2 and PDE3A3 eluted in a single LMW peak (FIG. 8B). As seen in FIG. 8C, immunoprecipitation of PDE3A from pooled HMW or LMW peaks of solubilized membranes, followed by Western blotting with anti-phosphorylated PKA substrate antibodies, demonstrated that PDE3A1 was highly and selectively phosphorylated at PKA sites in HMW peaks. These results suggested that phosphorylation of endogenous PDE3A1 by PKA may be involved in its incorporation into HMW macromolecular complexes.

To confirm these findings, studies of phosphorylation of PDE3A by rPKAc were carried out in vitro using immunoprecipitated PDE3A from solubilized myocardial membranes. PDE3A was incubated with $\gamma^{32}$P-ATP in the presence or absence of rPKAc. Phosphorimaging of wet gels after SDS-PAGE and Western blotting demonstrated that both PDE3A1 and PDE3A2 could be markedly phosphorylated by rPKAc (FIG. 8D, upper panels), with little if any increase in the phosphorylation of PDE3A3 under these conditions. As seen in FIG. 8D (lower panel), phosphorylation by rPKAc was accompanied by a stimulation of PDE3A activity (35% compared to controls, p<0.01).

PDE3A Associates Phosphorylation-Dependently with PLB, SERCA2 and AKAP18

We examined the effects of phosphorylation by PKA on the interaction of PDE3A1 with PLB, SERCA2 and AKAP18 (FIGS. 9 and 10). Pooled and concentrated membrane LMW S6 fractions from two different experiments (analogous to fractions 24-34 in FIG. 8A) were divided and incubated in the absence or presence of rPKAc, and then re-chromatographed on S6-columns (FIG. 9) or immunoprecipitated with anti-PDE3A antibody (FIG. 10). PDE3 activity in control pooled membrane S6-column LMW fractions exhibited an apparent molecular mass of 700 kDa during re-chromatography on S6-columns (FIG. 9); after incubation with rPKAc, however, the apparent molecular mass of most of the eluted and PDE3A1 and PDE3A2 was ≥3000 kDa, while most of the PDE3A3, which was not phosphorylated or only weakly phosphorylated by rPKAc (FIG. 8), remained in the low-MW fraction (FIG. 9). This indicates that phosphorylation by rPKAc (cf FIG. 8D) induced the shift in elution of PDE3A1 and PDE3A2. Shifts from LMW to the HMW fractions were also observed for AKAP18, PLB, PKA-RII and PKA catalytic subunits as well as PP1 and Cav3. As seen in FIG. 10, incubation of pooled membrane LMW fractions with rPKAc increased the co-immunoprecipitation of PDE3A with AKAP18 (not AKAP LBC), SERCA2, PP2A, PP1 and cav3, but reduced the co-immunoprecipitation of PLB. These results suggest that phosphorylation of membrane-associated PDE3A promotes its integration into macromolecular complexes containing AKAP18, SERCA2 and other proteins involved in the cAMP-mediated regulation of $Ca^{2+}$ transients and myocardial contractility. The decreased association of PLB with these proteins following phosphorylation by PKA is consistent with the integration of PLB into this complex being dependent upon its interactions with SERCA2 and AKPA18, both of which are reduced by its phosphorylation by PKA at S16 (2,24).

Because PDE3A1 is the most highly PKA-phosphorylated isoform in human myocardium (FIG. 8), we studied its phosphorylation-dependent interactions with SERCA2 and AKAP18δ in more detail using recombinant forms of these proteins. The co-IP of both proteins with PDE3A1 was increased by phosphorylation of PDE3A1 by rPKAc (FIG. 11, FIG. 12)

To gain insight into molecular mechanisms contributing to the phosphorylation-dependent interaction of PDE3A1 and SERCA2, we generated PDE3A1 constructs with C- and N-terminal deletions and serine-to-alanine mutations at PKA sites in the PDE3A1 N-terminus. rSERCA2 also co-immunoprecipitated with rPDE3A-RD, a construct containing only the N-terminal portion of PDE3A1 (aa 146-484, including both its shared sequence with PDE3A2 and its unique N-terminal extension), but not with rhPDE3A-A510, a recombinant form from which the first 510 aa of the PDE3A open reading frame were deleted (FIG. 11). This indicated that interactions with SERCA2 involved the N-terminus of PDE3A1.

With at least four PKA consensus sites (R-R-X-S/T) in the rhPDE3A1 N-terminus, we inserted serine-to-alanine mutations in these sites: S292/293A (M1), S312A (M2), S428A (M3), S438A (M4), S292/S293/S312/S438 (M5). The M1 and M5 mutations markedly diminished PKA-stimulated interactions with SERCA2. PDE3A mutants M2 (S312A) and M3 (S428A) showed slightly decreased phosphorylation-dependent interactions with SERCA2, while the PDE3A M4 mutation (S438A) had no effect (FIG. 11). These data indicate that S292/S293 is the major PKA site regulating the interaction of PDE3A1 with SERCA2.

Discussion

PDEs have critical roles in the compartmentation of cAMP signaling (25-28). A number of studies involving many different PDEs have demonstrated that these enzymes are recruited to specific intracellular complexes through protein-protein interactions, and that, as a result of this localization, individual PDEs are able to regulate specific cAMP-mediated signaling pathways with great precision. Understanding the mechanisms by which PDEs are localized to multiprotein complexes and the consequences of this localization are especially important in cardiac muscle, where inhibitors of the PDE3 family of enzymes are used to increase contractility in patients with heart failure. In earlier work, we showed that inotropic responses to PDE3 inhibition in mice, which correlated with increases in intracellular Ca2+ transients, are attributable specifically to isoforms in the PDE3A subfamily, and that PDE3A1 is a component of a SERCA2-regulatory signalosome (1,2,22). In the experiments described here, we have confirmed that PDE3A1 is part of a similar SERCA2-, PLB- and AKAP18-containing complex localized to sarcomeric Z-bands in human cardiac myocytes. Our observation that PDE3-selective inhibition (but not PDE4 inhibition) increases the phosphorylation of PLB by endogenous PKA and stimulates Ca2+ uptake in SR-enriched vesicles prepared from this tissue is evidence for the physiologic and therapeutic importance of this association. Finally, we showed that the interactions of PDE3A1 with SERCA2 and AKAP18 are phosphorylation-dependent, and that the former interaction is mediated principally by the phosphorylation of PDE3A1 at S292/S293, a sequence in its unique N-terminal extension.

While both PDE3 and PDE4 have been found to co-IP with PLB in complexes from mouse and human myocardium(22,23,29), our studies show that PDE4-selective inhibition does not potentiate the PKA-mediated stimulation of PLB phosphorylation and SERCA2 activity, while PDE3-selective inhibition does. This most likely reflects the higher amount of PDE3 activity relative to PDE4 activity in SR preparations from human myocardium.

Previous studies of PDE3B showed a role for N-terminal phosphorylation in integrating the enzyme into multiprotein complexes in response to insulin or β3-adrenergic receptor agonists. N-terminal phosphorylation in response to PKA and PKC activation has also been shown to regulate the interactions of PDE3A isoforms with 14-3-3 and with other (as-yet-unidentified) proteins (14). The interactions with 14-3-3 were consequences of the phosphorylation of two sites in the N-terminal sequence common to both PDE3A1 and PDE3A2, S312 and S428; there was no evidence for the involvement of any other phosphorylation sites in regulating protein-protein interactions. Our new results showing that PDE3A interacts directly with both SERCA2 and AKAP18 in a phosphorylation-dependent manner, and that, in the case of SERCA2, this interaction is mediated by the phosphorylation of S292/S293, a site unique to PDE3A1 that was not known to have a role in regulating protein-protein interactions, add significantly to our understanding of the molecular mechanisms through which PDE3 is localized to intracellular signaling complexes that control intracellular $Ca^{2+}$ handling.

As noted earlier, the sequences of PDE3A1 and PDE3A2 are identical save for the presence in the former of a unique 154-amino-acid N-terminal extension. Understanding how this extension affects the function of PDE3A1 is therefore central to understanding the unique roles of the two isoforms. A growing body of evidence indicates that several molecular mechanisms are involved. The hydrophobic loops within this sequence restrict PDE3A1's distribution to cellular and intracellular membranes. Within these membranes, the protein-protein interactions of each isoform are clearly different: the 5-HT receptor, for example, binds to PDE3A1 but not to PDE3A2 (30). The N-terminal extension also affects the tertiary structure of the downstream sequence: its presence converts S428 from being a strong PKC site in PDE3A2 to a weaker one in PDE3A1. This contributes to the selective regulation of these isoforms by preferential phosphorylation of PDE3A1 at the protein-binding site S312 by PKA and preferential phosphorylation of PDE3A2 by PKC at the protein-binding site S428 (14). Since phosphorylation promotes the association of each isoform with different proteins, this is likely to be a factor in the two isoforms having distinct interactomes. In addition, phosphorylation by PKB of the S292/S293 site, which is found within the N-terminal extension unique to PDE3A1, stimulates cAMP-hydrolytic activity, providing another mechanism by which PDE3A1 can be selectively regulated (31).

Our results showing that the interaction of PDE3A1 with SERCA2a is dependent upon the phosphorylation of S292/S293 reveals a new and important mechanism through which its unique N-terminal extension regulates PDE3A1 function. The amino-acid sequence surrounding this site, aa 288-294 of SEQ ID NO: 1, is RRRRSSS, and all three serines can be phosphorylated in vitro under different conditions (31); hence it is likely this site can be phosphorylated by different kinases activated in response to different upstream signals. Phosphorylation at S292/S293 may promote direct interactions of PDE3A1-binding proteins such as SERCA2a with this site. Alternatively, phosphorylation at S292/S293 may influence the conformation of PDE3A1 allosterically to promote binding to a different protein-protein interface. In either case, our results open the possibility that an agent capable of binding to PDE3A1 in its S292/S293-phosphorylated conformation may be able to inhibit its phosphorylation-dependent protein-protein interactions, thereby selectively inhibiting the integration of PDE3A1 into specific complexes.

Our findings add to the understanding of the mechanisms whereby PDE3A, a component of a SERCA2-containing signalosome, regulates cAMP-mediated changes in contractility in cardiac myocytes. Phosphorylation of PLB on amino acid S16 causes its dissociation from SERCA2, relieving its inhibition of SERCA2 activity and increasing $Ca^{2+}$ transport into the SR (24,32,33). These actions increase the amplitude of intracellular $Ca^{2+}$ transients, which are attenuated in dilated cardiomyopathy (34). PKA-catalyzed phosphorylation of PLB at S16, induced by isoproterenol, forskolin or IBMX, correlated with increased cardiac relaxation (24,35). The interaction of PLB with AKAP18 is also reduced by phosphorylation of S16 (2). Phosphorylation of PDE3A1 at S292/S293, which leads to its recruitment into the SERCA2 regulatory signalosome and to an increase in its cAMP-hydrolytic activity, would tend to counteract this effect by reducing the concentration of cAMP in the proximity of this complex (FIG. 13). This combination of stimulation and inhibition of SERCA2 activity in response to PKA activation through separate mechanisms may permit a greater degree of 'fine tuning' of SR $Ca^{2+}$ handling in response to β-AR agonists. It may also explain the synergism observed when PDE3 inhibitors are used in combination with β-AR agonists as inotropic agents. Since PP2A and PP1 are thought to be the principal phosphatases responsible for dephosphorylation of PKA substrates and PLB (36), the presence of PP1 and PP2A in the complex would be expected to catalyze the dephosphorylation of PDE3A, PLB and other PKA substrates and return the SERCA2 complex to its basal state. Of note, AKAP18 associates with inhibitor I and thereby can control PP1 activity (37).

Our results have therapeutic implications. Selective inhibition of the PDE3A isoforms associated with SERCA2 might allow the inotropic benefits of stimulating $Ca^{2+}$ transport into the sarcoplasmic reticulum without the harmful effects of global inhibition of PDE3 activity (38). Currently available PDE3 inhibitors, however, have little selectivity for PDE3A versus PDE3B isoforms, whose catalytic domains are similar, and no selectivity for individual PDE3A isoforms, whose catalytic domains are identical (39). Blocking the integration of PDE3A1 into SERCA2-containing complexes, either by blocking its phosphorylation or by blocking the interactions of phosphorylated PDE3A1 with SERCA2 and/or other constituents of the complexes, may be a way of targeting PDE3 activity in a specific microdomain in cardiac myocytes to stimulate SR $Ca^{2+}$ uptake and produce inotropic actions without the adverse consequences that accompany diffuse increases in intracellular cAMP content.

REFERENCES

1. Sun, B., Li, H., Shakur, Y., Hensley, J., Hockman, S., Kambayashi, J., Manganiello, V. C., and Liu, Y. (2007)—Cell Signal. 19, 1765-1771

2. Lygren, B., Carlson, C. R., Santamaria, K., Lissandron, V., McSorley, T., Litzenberg, J., Lorenz, D., Wiesner, B., Rosenthal, W., Zaccolo, M., Tasken, K., and Klussmann, E. (2007)—*Embo Rep.* 8, 1061-1067
3. Henn, V., Edemir, B., Stefan, E., Wiesner, B., Lorenz, D., Theilig, F., Schmitt, R., Vossebein, L., Tamma, G., Beyermann, M., Krause, E., Herberg, F. W., Valenti, G., Bachmann, S., Rosenthal, W., and Klussmann, E. (2004) *J Biol. Chem.* 279, 26654-26665
4. Ahmad, F., Lindh, R., Tang, Y., Weston, M., Degerman, E., and Manganiello, V. C. (2007)—*Biochem J.* 404, 257-268
5. Ahmad, F., Lindh, R., Tang, Y., Ruishalme, I., Ost, A., Sahachartsiri, B., Stralfors, P., Degerman, E., and Manganiello, V. C. (2009)—*Biochem J.* 424, 399-410
6. Onuma, H., Osawa, H., Yamada, K., Ogura, T., Tanabe, F., Granner, D. K., and Makino, H. (2002)—*Diabetes.* 51, 3362-3367
7. Palmer, D., Jimmo, S. L., Raymond, D. R., Wilson, L. S., Carter, R. L., and Maurice, D. H. (2007)—*J Biol Chem.* 282, 9411-9419
8. Nilsson, R., Ahmad, F., Sward, K., Andersson, U., Weston, M., Manganiello, V., and Degerman, E. (2006)—*Cell Signal.* 18, 1713-1721
9. Rondinone, C. M., Carvalho, E., Rahn, T., Manganiello, V. C., Degerman, E., and Smith, U. P. (2000)—*J Biol Chem.* 275, 10093-10098
10. Perino, A., Ghigo, A., Ferrero, E., Morello, F., Santulli, G., Baillie, G. S., Damilano, F., Dunlop, A. J., Pawson, C., Walser, R., Levi, R., Altruda, F., Silengo, L., Langeberg, L. K., Neubauer, G., Heymans, S., Lembo, G., Wymann, M. P., Wetzker, R., Houslay, M. D., Iaccarino, G., Scott, J. D., and Hirsch, E. (2011)—*Mol Cell.* 42, 84-95
11. Wilson, L. S., Baillie, G. S., Pritchard, L. M., Umana, B., Terrin, A., Zaccolo, M., Houslay, M. D., and Maurice, D. H. (2011)—*J Biol Chem.* 286, 16285-96
12. Pozuelo, R. M., Campbell, D. G., Morrice, N. A., and Mackintosh, C. (2005)—*Biochem J.* 392, 163-172
13. Hunter, R. W., Mackintosh, C., and Hers, I. (2009) *J Biol Chem.* 284(18), 12339-12348
14. Vandeput, F., Szabo-Fresnais, N., Ahmad, F., Kho, C., Lee, A., Krall, J., Dunlop, A., Hazel, M. W., Wohlschlegel, J. A., Hajjar, R. J., Houslay, M. D., Manganiello, V. C., and Movsesian, M. A. (2013) *Proc Natl Acad Sci USA.* 110(49), 19778-19783
15. Babick, A. P., Cantor, E. J., Babick, J. T., Takeda, N., Dhalla, N. S., and Netticadan, T. (2004)—*Am J Physiol Cell Physiol.* 287, C1202-C1208
16. Manganiello, V. and Vaughan, M. (1973)—*J Biol Chem.* 248, 7164-7170
17. Mishra, S., Sabbah, H. N., Rastogi, S., Imai, M., and Gupta, R. C. (2005)—*Heart Vessels.* 20, 23-32
18. Kirchgesser, M. and Dahlmann, N. (1990)—*J Clin Chem Clin Biochem.* 28, 407-411
19. Wechsler, J., Choi, Y. H., Krall, J., Ahmrad, F., Manganiello, V. C., and Movsesian, M. A. (2002)—*J Biol Chem.* 277, 38072-38078
20. Shakur, Y., Takeda, K., Kenan, Y., Yu, Z. X., Rena, G., Brandt, D., Houslay, M. D., Degerman, E., Ferrans, V. J., and Manganiello, V. C. (2000) *J Biol Chem.* 275(49), 38749-38761
21. Vandeput, F., Wolda, S. L., Krall, J., Hambleton, R., Uher, L., McCaw, K. N., Radwanski, P. B., Florio, V., and Movsesian, M. A. (2007)—*J Biol Chem.* 282, 32749-32757
22. Beca, S., Ahmad, F., Shen, W., Liu, J., Makary, S., Polidovitch, N., Sun, J., Hockman, S., Chung, Y. W., Movsesian, M., Murphy, E., Manganiello, V., and Backx, P. H. (2013) *Circ. Res.* 112(2), 289-297
23. Richter, W., Xie, M., Scheitrum, C., Krall, J., Movsesian, M., and Conti M (2011)—*Basic Res Cardiol.* 106, 249-262
24. MacLennan, D. H. and Kranias, E. G. (2003)—*Nat Rev Mol Cell Biol.* 4, 566-577
25. Yan, C., Miller, C. L., and Abe, J. (2007)—*Circ Res.* 100, 489-501
26. Mongillo, M., McSorley, T., Evellin, S., Sood, A., Lissandron, V., Terrin, A., Huston, E., Hannawacker, A., Lohse, M. J., Pozzan, T., Houslay, M. D., and Zaccolo, M. (2004)—*Circ Res.* 95, 67-75
27. Houslay, M. D., Baillie, G. S., and Maurice, D. H. (2007)—*Circ. Res.* 100, 950-966
28. Zaccolo, M. (2009)—*Br J Pharmacol.* 158, 50-60
29. Maurice, D. H., Ke, H., Ahmad, F., Wang, Y., Chung, J., and Manganiello, V. C. (2014) *Nat Rev Drug Discov.* 13(4), 290-314
30. Weninger, S., Van, C. K., Cameron, R. T., Vandeput, F., Movsesian, M. A., Baillie, G. S., and Lefebvre, R. A. (2014) *Cell Signal.* 26(11), 2573-2582
31. Han, S. J., Vaccari, S., Nedachi, T., Andersen, C. B., Kovacina, K. S., Roth, R. A., and Conti, M. (2006) *EMBO J.* 25(24), 5716-5725
32. Simmerman, H. K. and Jones, L. R. (1998)—*Physiol Rev.* 78, 921-947
33. Sande, J. B., Sjaastad, 1., Hoen, I. B., Bokenes, J., Tonnessen, T., Holt, E., Lunde, P. K., and Christensen, G. (2002)—*Cardiovasc Res.* 53, 382-391
34. Kawase, Y. and Hajjar, R. J. (2008)—*Nat Clin Pract Cardiovasc Med.* 5, 554-565
35. Kuschel, M., Karczewski, P., Hempel, P., Schlegel, W. P., Krause, E. G., and Bartel, S. (1999)—*Am J Physiol.* 276 (5 Pt 2), H1625-33
36. Schwoerer, A. P., Neuber, C., Schmechel, A., Melnychenko, I., Mearini, G., Boknik, P., Kirchhefer, U., Schmitz, W., Ehmke, H., Eschenhagen, T., and El-Armouche, A. (2008)—*J Mol Cell Cardiol.* 45, 846-852
37. Singh, A., Redden, J. M., Kapiloff, M. S., and Dodge-Kafka, K. L. (2011) *Mol Pharmacol.* 79(3), 533-540
38. Movsesian, M. A. (2003)—*J Card Fail.* 9, 475-480
39. Hambleton, R., Krall, J., Tikishvili, E., Honeggar, M., Ahmad, F., Manganiello, V. C., and Movsesian, M. A. (2005)—*J Biol Chem.* 280, 39168-39174

What is claimed is:

1. A method of treating myocardial hypertrophy comprising introducing to a cardiac myocyte of cardiac muscle an isolated or purified polypeptide possessing anti-hypertrophic activity in the cardiac myocyte, in an amount effective so as to treat myocardial hypertrophy wherein the polypeptide is a catalytically inactive or functionally compromised mutant derived from wild-type PDE3A1 protein, wherein wild-type PDE3A1 protein is a cyclic nucleotide phosphodiesterase hydrolyzing cAMP and/or cGMP, and wherein the wild-type PDE3A1 protein has the amino-acid sequence given in SEQ ID NO:1 at amino acid position 146 to 1141.

2. The method of claim 1, wherein the catalytically inactive mutant of PDE3A1 protein has a mutation at phenylalanine-1004 (F1004).

3. The method of claim 2, wherein the mutation is an amino acid change from phenylalanine to alanine.

4. The method of claim 1, wherein the catalytically inactive mutant of PDE3A1 protein is a result of a mutation at tyrosine-751 (Y751), histidine-836 (H836), histidine-840 (H840), glutamic acid-866 (E866), aspartic acid-950 (D950), or phenylalanine-1004 (F1004).

5. The method of claim 1, wherein the mutant derived from wild-type PDE3A1 protein is a deletion mutant of PDE3A1 protein.

6. The method of claim 5, wherein the deletion mutant of PDE3A1 protein lacks an intact C-terminal catalytic region.

7. The method of claim 1, wherein the polypeptide comprises a sequence of amino acids in PDE3A that includes a serine amino acid that is differentially phosphorylated between PDE3A1 and PDE3A2 isoforms or a phosphorylated serine amino acid that is unique to PDE3A1.

8. The method of claim 5, further comprising a mutation(s) in which amino acid corresponding to serine-292, serine-293 and/or serine-294 as provided in SEQ ID NO:1 is/are substituted with aspartic acid, glutamic acid or combination of aspartic acid and glutamic acid.

9. The method of claim 4, wherein the mutation is an amino acid change to any amino acid other than an alanine.

10. The polypeptide of claim 9, wherein the amino acid change to any amino acid other than an alanine is selected from a group of amino acids consisting of glycine, serine, threonine, cysteine, valine, leucine, isoleucine, methionine, proline, tyrosine, tryptophan, phenylalanine, aspartic acid, glutamic acid, asparagine, glutamine, histidine, lysine or arginine, and wherein not selected from the group is amino acid present in the wild-type PDE3A1 at a position to be mutated.

11. The method of claim 1, wherein catalytically inactive or functionally compromised mutant derived from wild-type PDE3A1 protein has or comprises a mutation in the C-terminal catalytic region comprising the amino acid 669 to 1108 of SEQ ID NO: 1, or alternatively, comprises an amino-terminal sequence without the C-terminal catalytic region.

12. A method of inhibiting or reversing myocardial hypertrophy in cardiac muscle comprising introducing to a cardiac myocyte of cardiac muscle an isolated or purified polypeptide possessing anti-hypertrophic activity in the cardiac myocyte in an amount effective so as to inhibit or reverse myocardial hypertrophy, wherein the polypeptide is a catalytically inactive or compromised mutant derived from wild-type PDE3A1 protein, wherein wild-type PDE3A1 protein is a cyclic nucleotide phosphodiesterase hydrolyzing cAMP and/or cGMP, and wherein the wild-type PDE3A1 protein has the amino-acid sequence given in SEQ ID NO:1 at amino acid position 146 to 1141.

* * * * *